(12) United States Patent
Chhikara et al.

(10) Patent No.: US 10,086,170 B2
(45) Date of Patent: Oct. 2, 2018

(54) SELF-PRIMING SYSTEMS AND METHODS

(71) Applicant: ICU MEDICAL, INC., San Clemente, CA (US)

(72) Inventors: Bhupinder Chhikara, Draper, UT (US); Srinath Lingutla, Salt Lake City, UT (US); Brandon Eads, Taylorsville, UT (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 15/227,297

(22) Filed: Aug. 3, 2016

(65) Prior Publication Data

US 2017/0182293 A1    Jun. 29, 2017

Related U.S. Application Data

(63) Continuation of application No. PCT/US2015/014240, filed on Feb. 3, 2015.

(60) Provisional application No. 61/935,802, filed on Feb. 4, 2014.

(51) Int. Cl.
  *A61M 25/06* (2006.01)
  *A61M 39/24* (2006.01)
  *A61M 25/10* (2013.01)

(52) U.S. Cl.
  CPC .... *A61M 25/0606* (2013.01); *A61M 25/0693* (2013.01); *A61M 39/24* (2013.01); *A61M 2025/1077* (2013.01)

(58) Field of Classification Search
  CPC .......... A61M 25/0606; A61M 25/0693; A61M 39/24

USPC .............. 604/30, 31, 44, 164.01–164.09, 43; 600/565, 566
See application file for complete search history.

(56) References Cited

U.S. PATENT DOCUMENTS

| | | | |
|---|---|---|---|
| 2,868,200 A | | 1/1959 | Gewecke |
| 3,561,429 A | * | 2/1971 | Jewett ..................... A61B 10/04 600/565 |
| 3,729,031 A | | 4/1973 | Baldwin |
| 4,013,080 A | | 3/1977 | Froning |

(Continued)

FOREIGN PATENT DOCUMENTS

| | | |
|---|---|---|
| EP | 0 576 302 | 12/1993 |
| EP | 0 821 980 | 4/2003 |

(Continued)

OTHER PUBLICATIONS

International Search Report and Written Opinion, re PCT Application No. PCT/US2015/014240, dated May 15, 2015.

(Continued)

*Primary Examiner* — Manuel Mendez
(74) *Attorney, Agent, or Firm* — Knobbe Martens Olson & Bear, LLP

(57) ABSTRACT

Vascular access system embodiments can be configured to remove gas and a piercing member from a catheter assembly. In some embodiments, vascular access systems can remove gas and at least a portion of a piercing member concurrently or simultaneously. In some embodiments, vascular access systems can remove gas before removing at least a portion of a piercing member. In several embodiments, a vascular access system can include a first barrel configured to remove gas and a second barrel configured to retract a piercing member.

18 Claims, 59 Drawing Sheets

(56) References Cited

U.S. PATENT DOCUMENTS

| | | |
|---|---|---|
| 4,160,450 A | 7/1979 | Doherty |
| 4,316,461 A | 2/1982 | Marais et al. |
| 4,380,234 A | 4/1983 | Kamen |
| 4,397,641 A | 8/1983 | Jacobs |
| 4,424,833 A | 1/1984 | Spector et al. |
| 4,430,073 A | 2/1984 | Bemis et al. |
| 4,432,752 A | 2/1984 | Marlon |
| 4,435,173 A * | 3/1984 | Siposs ............... A61M 5/1456 128/DIG. 1 |
| 4,436,519 A | 3/1984 | O'Neill |
| 4,576,589 A | 3/1986 | Krause et al. |
| 4,591,356 A | 5/1986 | Christie |
| 4,605,011 A * | 8/1986 | Naslund ............ A61B 10/0283 600/565 |
| 4,681,567 A | 7/1987 | Masters et al. |
| 4,695,274 A | 9/1987 | Fox |
| 4,755,170 A | 7/1988 | Golden |
| 4,776,841 A | 10/1988 | Catalano |
| 4,798,594 A | 1/1989 | Hillstead |
| 4,799,494 A * | 1/1989 | Wang ................ A61B 10/0283 600/566 |
| 4,801,295 A | 1/1989 | Spencer |
| 4,834,271 A | 5/1989 | Litwin |
| 4,834,718 A | 5/1989 | McDonald |
| 4,846,796 A | 7/1989 | Carrell et al. |
| 4,890,626 A * | 1/1990 | Wang ................ A61B 10/0283 600/565 |
| 4,898,587 A | 2/1990 | Mera |
| 4,909,798 A | 3/1990 | Fleischhacker et al. |
| 4,935,010 A | 6/1990 | Cox et al. |
| 4,941,883 A | 7/1990 | Venturini |
| 4,944,725 A | 7/1990 | McDonald |
| 4,944,728 A | 7/1990 | Carrell et al. |
| 4,952,207 A | 8/1990 | Lemieux |
| 4,964,854 A | 10/1990 | Luther |
| 4,976,698 A | 12/1990 | Stokley |
| 5,000,740 A | 3/1991 | Ducharme et al. |
| 5,049,136 A | 9/1991 | Johnson |
| 5,084,023 A | 1/1992 | Lemieux |
| 5,084,026 A | 1/1992 | Shapiro |
| 5,085,648 A | 2/1992 | Purdy et al. |
| 5,092,845 A | 3/1992 | Chang |
| 5,098,048 A | 3/1992 | Chen |
| 5,116,324 A | 5/1992 | Brierley et al. |
| 5,129,884 A | 7/1992 | Dysarz |
| 5,135,504 A | 8/1992 | Mclees |
| 5,147,327 A | 9/1992 | Johnson |
| 5,147,333 A | 9/1992 | Raines |
| 5,147,375 A | 9/1992 | Sullivan et al. |
| 5,171,234 A | 12/1992 | Jepson et al. |
| 5,192,275 A | 3/1993 | Burns |
| 5,199,948 A | 4/1993 | McPhee |
| 5,201,717 A | 4/1993 | Wyatt et al. |
| 5,207,647 A | 5/1993 | Phelps |
| 5,211,634 A | 5/1993 | Vaillancourt |
| 5,215,525 A | 6/1993 | Sturman |
| 5,215,528 A | 6/1993 | Purdy et al. |
| 5,215,537 A | 6/1993 | Lynn et al. |
| 5,232,010 A | 8/1993 | Rozenblatt et al. |
| 5,238,010 A | 8/1993 | Grabenkort et al. |
| 5,254,097 A | 10/1993 | Schock et al. |
| 5,269,771 A | 12/1993 | Thomas et al. |
| 5,295,970 A | 3/1994 | Clinton et al. |
| 5,295,977 A | 3/1994 | Cohen et al. |
| 5,300,034 A | 4/1994 | Behnke et al. |
| 5,312,368 A | 5/1994 | Haynes |
| 5,314,411 A | 5/1994 | Bierman et al. |
| 5,351,383 A | 5/1994 | Behnke et al. |
| 5,330,438 A | 7/1994 | Gollobin et al. |
| 5,352,205 A | 10/1994 | Dales et al. |
| 5,354,275 A | 10/1994 | Behnke et al. |
| 5,354,282 A | 10/1994 | Bierman |
| 5,356,390 A | 10/1994 | Erskine |
| 5,360,408 A | 11/1994 | Vaillancourt |
| 5,364,368 A | 11/1994 | Kauffman et al. |
| 5,368,801 A | 11/1994 | Vaillancourt |
| 5,375,589 A | 12/1994 | Bhatta |
| 5,376,071 A | 12/1994 | Henderson |
| 5,376,082 A * | 12/1994 | Phelps ............... A61B 17/3401 604/158 |
| 5,400,500 A | 3/1995 | Behnke et al. |
| 5,405,331 A | 4/1995 | Behnke et al. |
| 5,413,562 A | 5/1995 | Swauger |
| 5,425,465 A | 6/1995 | Healy |
| 5,425,721 A | 6/1995 | Malenchek |
| 5,439,451 A | 8/1995 | Collinson et al. |
| 5,445,623 A | 8/1995 | Richmond |
| 5,456,668 A | 10/1995 | Ogle, II |
| 5,458,658 A | 10/1995 | Sircom |
| 5,462,255 A | 10/1995 | Rosen et al. |
| 5,472,430 A | 12/1995 | Vaillancourt et al. |
| 5,474,544 A | 12/1995 | Lynn |
| 5,476,452 A | 12/1995 | Thompson |
| 5,487,728 A | 1/1996 | Vaillancourt |
| 5,487,734 A | 1/1996 | Thorne et al. |
| 5,498,247 A | 3/1996 | Brimhall |
| 5,501,674 A | 3/1996 | Trombley, III et al. |
| 5,509,912 A | 4/1996 | Vaillancourt et al. |
| 5,514,111 A | 5/1996 | Phelps |
| 5,514,116 A | 5/1996 | Vaillancourt et al. |
| 5,522,804 A | 6/1996 | Lynn |
| 5,545,146 A | 8/1996 | Ishak |
| 5,549,651 A | 8/1996 | Lynn |
| 5,558,651 A | 9/1996 | Crawford et al. |
| 5,562,631 A | 10/1996 | Bogert |
| 5,575,769 A | 11/1996 | Vaillancourt |
| 5,575,777 A | 11/1996 | Cover et al. |
| 5,591,138 A | 1/1997 | Vaillancourt |
| 5,601,536 A | 2/1997 | Crawford et al. |
| 5,643,216 A | 7/1997 | White |
| 5,669,891 A | 9/1997 | Vaillancourt |
| 5,676,656 A | 10/1997 | Brimhall |
| 5,676,658 A | 10/1997 | Erskine |
| 5,688,253 A | 11/1997 | Paradis |
| 5,697,914 A | 12/1997 | Brimhall |
| 5,697,915 A | 12/1997 | Lynn |
| 5,702,367 A | 12/1997 | Cover et al. |
| 5,702,371 A | 12/1997 | Bierman |
| 5,704,914 A | 1/1998 | Stocking et al. |
| 5,713,876 A | 2/1998 | Bogert et al. |
| 5,725,499 A | 3/1998 | Silverstein et al. |
| 5,727,770 A | 3/1998 | Dennis |
| 5,735,826 A | 4/1998 | Richmond |
| 5,735,827 A | 4/1998 | Adwers et al. |
| 5,740,810 A | 4/1998 | Johnson et al. |
| 5,743,884 A | 4/1998 | Hasson et al. |
| 5,746,727 A | 5/1998 | Graves et al. |
| 5,749,857 A | 5/1998 | Cuppy |
| 5,755,709 A | 5/1998 | Cuppy |
| 5,769,825 A | 6/1998 | Lynn |
| 5,788,675 A | 8/1998 | Mayer |
| 5,810,780 A | 9/1998 | Brimhall |
| 5,827,221 A | 10/1998 | Phelps |
| 5,830,184 A | 11/1998 | Basta |
| 5,833,662 A | 11/1998 | Stevens |
| 5,846,227 A | 12/1998 | Osterlind |
| 5,879,330 A | 3/1999 | Bell |
| 5,902,274 A | 5/1999 | Yamamoto et al. |
| 5,911,705 A | 6/1999 | Howell |
| 5,913,845 A | 6/1999 | Brimhall |
| 5,916,199 A | 6/1999 | Miles |
| 5,935,110 A | 8/1999 | Brimhall |
| 5,954,698 A | 9/1999 | Pike |
| 5,957,887 A | 9/1999 | Oesterlind et al. |
| 5,989,220 A | 11/1999 | Shaw et al. |
| 5,997,504 A | 12/1999 | Bell |
| 6,001,080 A | 12/1999 | Kuracina et al. |
| 6,004,294 A | 12/1999 | Brimhall et al. |
| 6,022,339 A | 2/2000 | Fowles et al. |
| 6,027,480 A | 2/2000 | Davis et al. |
| 6,033,382 A | 3/2000 | Basta |
| 6,056,718 A | 5/2000 | Funerburk et al. |
| 6,077,244 A | 6/2000 | Botich et al. |
| 6,077,248 A | 6/2000 | Zumschlinge |

(56) References Cited

U.S. PATENT DOCUMENTS

| | | |
|---|---|---|
| 6,086,564 A | 7/2000 | McLaughlin |
| 6,142,981 A | 11/2000 | Heck et al. |
| 6,149,632 A | 11/2000 | Landuyt |
| 6,152,913 A | 11/2000 | Feith et al. |
| 6,162,206 A | 12/2000 | Bindokas et al. |
| 6,168,137 B1 | 1/2001 | Paradis |
| 6,197,007 B1 | 3/2001 | Thorne et al. |
| 6,210,624 B1 | 4/2001 | Mayer |
| 6,213,978 B1 | 4/2001 | Voyten |
| 6,221,048 B1 | 4/2001 | Phelps |
| 6,228,065 B1 | 5/2001 | Lynn |
| 6,261,259 B1 | 7/2001 | Bell |
| 6,261,268 B1 | 7/2001 | Mayer |
| 6,273,869 B1 | 8/2001 | Vaillancourt |
| 6,273,871 B1 | 8/2001 | Davis et al. |
| RE37,357 E | 9/2001 | Lynn |
| 6,299,602 B1 | 10/2001 | Miller et al. |
| 6,302,866 B1 | 10/2001 | Marggi |
| 6,342,120 B1 | 1/2002 | Basta |
| 6,375,639 B1 | 4/2002 | Duplessie et al. |
| 6,379,333 B1 | 4/2002 | Brimhall et al. |
| 6,379,337 B1 | 4/2002 | Mohammad |
| 6,443,929 B1 | 9/2002 | Kuracina et al. |
| 6,506,181 B2 | 1/2003 | Meng et al. |
| 6,520,938 B1 | 2/2003 | Funderburk et al. |
| 6,569,120 B1 | 5/2003 | Green et al. |
| RE38,145 E | 6/2003 | Lynn |
| 6,572,586 B1 | 6/2003 | Wojcik |
| 6,572,588 B1 | 6/2003 | Bierman |
| 6,572,591 B2 | 6/2003 | Mayer |
| 6,595,955 B2 | 7/2003 | Ferguson et al. |
| 6,623,461 B1 | 9/2003 | Wilkinson et al. |
| 6,638,252 B2 | 10/2003 | Moulton et al. |
| 6,652,490 B2 | 11/2003 | Howell |
| 6,663,599 B2 | 12/2003 | Osborne et al. |
| 6,673,046 B2 | 1/2004 | Bierman et al. |
| 6,692,468 B1 | 2/2004 | Waldenburg |
| 6,699,221 B2 | 3/2004 | Vaillancourt |
| 6,712,790 B1 | 3/2004 | Prestidge et al. |
| 6,719,726 B2 | 4/2004 | Meng et al. |
| 6,719,727 B2 | 4/2004 | Brimhall et al. |
| 6,730,096 B2 | 5/2004 | Basta |
| 6,740,277 B2 | 5/2004 | Howell et al. |
| 6,749,588 B1 | 6/2004 | Howell et al. |
| 6,761,706 B2 | 7/2004 | Vaillancourt |
| 6,776,775 B1 | 8/2004 | Mohammad |
| 6,805,860 B1 | 10/2004 | Alt |
| 6,811,545 B2 | 11/2004 | Vaillancourt |
| 6,837,875 B1 | 1/2005 | Bierman |
| 6,849,051 B2 * | 2/2005 | Sramek ............ A61B 10/025 600/565 |
| 6,902,546 B2 | 6/2005 | Ferguson |
| 6,905,483 B2 | 6/2005 | Newby et al. |
| 6,908,459 B2 | 6/2005 | Harding et al. |
| 6,921,391 B1 | 7/2005 | Barker et al. |
| 6,926,721 B2 | 8/2005 | Basta |
| 6,953,448 B2 | 10/2005 | Moulton et al. |
| 6,955,659 B1 | 10/2005 | Carter |
| 6,972,002 B2 | 12/2005 | Thorne |
| 6,981,965 B1 | 1/2006 | Luther et al. |
| 6,981,966 B2 | 1/2006 | Green et al. |
| 6,984,223 B2 | 1/2006 | Newby et al. |
| RE38,996 E | 2/2006 | Crawford et al. |
| 6,997,902 B2 | 2/2006 | Thorne et al. |
| 6,997,913 B2 | 2/2006 | Wilkinson |
| 6,997,917 B2 | 2/2006 | Niedospial, Jr. et al. |
| 7,004,934 B2 | 2/2006 | Vaillancourt |
| 7,008,406 B2 | 3/2006 | Mayer |
| 7,022,111 B2 | 4/2006 | Duplessie et al. |
| 7,060,055 B2 | 6/2006 | Wilkinson et al. |
| 7,060,060 B1 | 6/2006 | Simpson et al. |
| 7,090,660 B2 | 8/2006 | Roberts et al. |
| 7,090,661 B2 | 8/2006 | Morris et al. |
| 7,112,191 B2 | 9/2006 | Daga |
| RE39,334 E | 10/2006 | Lynn |
| 7,125,398 B2 | 10/2006 | Garcia, Jr. |
| 7,141,040 B2 | 11/2006 | Lichtenberg |
| 7,147,622 B2 | 12/2006 | Gutierrez |
| 7,220,249 B2 | 5/2007 | Hwang et al. |
| 7,258,680 B2 | 8/2007 | Mogensen et al. |
| 7,344,516 B2 | 3/2008 | Erskine |
| 7,347,842 B2 | 3/2008 | Thorne et al. |
| 7,351,230 B2 | 4/2008 | Smith et al. |
| 7,354,422 B2 | 4/2008 | Riesenberger et al. |
| 7,396,346 B2 | 7/2008 | Nakajima |
| 7,413,562 B2 | 8/2008 | Ferguson et al. |
| 7,435,238 B2 | 10/2008 | Reid |
| 7,445,611 B2 | 11/2008 | Osborne et al. |
| 7,470,261 B2 | 12/2008 | Lynn |
| 7,481,797 B2 | 1/2009 | Mahurkar |
| 7,507,222 B2 | 3/2009 | Cindrich et al. |
| 7,569,033 B2 | 8/2009 | Greene et al. |
| 7,604,616 B2 | 10/2009 | Thoresen et al. |
| 7,611,499 B2 | 11/2009 | Woehr et al. |
| 7,615,033 B2 | 11/2009 | Leong |
| 7,618,395 B2 | 11/2009 | Ferguson |
| 7,625,360 B2 | 12/2009 | Woehr et al. |
| 7,635,357 B2 | 12/2009 | Mayer |
| 7,651,481 B2 | 1/2010 | Raybuck |
| 7,654,988 B2 | 2/2010 | Moulton et al. |
| 7,658,725 B2 | 2/2010 | Bialecki et al. |
| 7,666,166 B1 | 2/2010 | Emmert et al. |
| 7,670,299 B2 * | 3/2010 | Beckman ............ A61B 10/0275 600/566 |
| 7,670,317 B2 | 3/2010 | Cindrich et al. |
| 7,682,339 B2 | 3/2010 | Fujii |
| 7,694,403 B2 | 4/2010 | Moulton |
| 7,699,814 B2 | 4/2010 | Lande |
| 7,713,243 B2 | 5/2010 | Hillman |
| 7,713,250 B2 | 5/2010 | Harding et al. |
| 7,717,882 B2 | 5/2010 | Harding |
| 7,722,569 B2 | 5/2010 | Söderholm et al. |
| 7,736,332 B2 | 6/2010 | Carlyon et al. |
| 7,736,337 B2 | 6/2010 | Diep et al. |
| 7,736,342 B2 | 6/2010 | Abriles et al. |
| 7,740,615 B2 | 6/2010 | Shaw et al. |
| 7,744,572 B2 | 6/2010 | Bierman |
| 7,749,254 B2 | 7/2010 | Sobelman et al. |
| 7,762,993 B2 | 7/2010 | Perez |
| 7,763,199 B2 | 7/2010 | Fangrow, Jr. |
| 7,766,879 B2 | 8/2010 | Tan et al. |
| 7,766,897 B2 | 8/2010 | Ramsey et al. |
| 7,771,412 B2 | 8/2010 | Anderson et al. |
| 7,776,017 B2 | 8/2010 | Ponzi et al. |
| 7,798,991 B2 | 9/2010 | Insignares |
| 7,798,994 B2 | 9/2010 | Brimhall |
| 7,799,000 B2 | 9/2010 | Silich |
| 7,806,869 B2 | 10/2010 | Nilsson et al. |
| 7,833,201 B2 | 11/2010 | Carlyon et al. |
| 7,862,547 B2 | 1/2011 | Ferguson et al. |
| 7,887,515 B2 | 2/2011 | Bierman |
| 7,892,216 B2 | 2/2011 | Fangrow, Jr. |
| 7,918,828 B2 | 4/2011 | Lundgaard et al. |
| 7,931,615 B2 | 4/2011 | Fangrow, Jr. |
| 7,959,613 B2 | 6/2011 | Rhad et al. |
| 7,972,313 B2 | 7/2011 | Woehr et al. |
| 8,012,145 B2 | 9/2011 | Cawley |
| 8,025,644 B2 | 9/2011 | Chong et al. |
| 8,042,689 B2 | 10/2011 | Fröjd et al. |
| 8,043,265 B2 | 10/2011 | Abe et al. |
| 8,048,031 B2 | 11/2011 | Shaw et al. |
| 8,062,262 B2 | 11/2011 | Christensen et al. |
| 8,066,669 B2 | 11/2011 | Christensen et al. |
| 8,066,670 B2 | 11/2011 | Cluff et al. |
| 8,066,675 B2 | 11/2011 | Cindrich et al. |
| 8,066,678 B2 | 11/2011 | Vaillancourt et al. |
| 8,070,725 B2 | 12/2011 | Christensen |
| 8,079,979 B2 | 12/2011 | Moorehead |
| 8,083,728 B2 | 12/2011 | Rome |
| 8,092,435 B2 | 1/2012 | Beling et al. |
| 8,105,286 B2 | 1/2012 | Anderson et al. |
| 8,105,288 B2 | 1/2012 | Keyser et al. |
| 8,122,923 B2 | 2/2012 | Krause et al. |
| 8,123,738 B2 | 2/2012 | Vaillancourt |

(56) References Cited

U.S. PATENT DOCUMENTS

| | | |
|---|---|---|
| 8,133,202 B2 | 3/2012 | Marsh |
| 8,133,206 B2 | 3/2012 | Greene et al. |
| 8,147,465 B2 | 4/2012 | Kern |
| 8,157,770 B2 | 4/2012 | Elwell et al. |
| 8,162,882 B2 | 4/2012 | Rubinstein et al. |
| 8,162,896 B2 | 4/2012 | Tan |
| 8,162,914 B2 | 4/2012 | Kraushaar et al. |
| 8,163,237 B2 | 4/2012 | Crawford et al. |
| 8,172,803 B2 | 5/2012 | Morrissey et al. |
| 8,172,825 B2 | 5/2012 | Solomon et al. |
| 8,177,745 B2 | 5/2012 | Brechbuehler et al. |
| 8,177,753 B2 | 5/2012 | Vitullo et al. |
| 8,177,754 B2 | 5/2012 | Barnes |
| 8,177,755 B2 | 5/2012 | Berry et al. |
| 8,177,760 B2 | 5/2012 | Rome et al. |
| 8,177,762 B2 | 5/2012 | Beasley et al. |
| 8,182,448 B2 | 5/2012 | Emmert et al. |
| 8,197,452 B2 | 6/2012 | Harding et al. |
| 8,197,466 B2 | 6/2012 | Yokota et al. |
| 8,211,070 B2 | 7/2012 | Woehr et al. |
| 8,226,612 B2 | 7/2012 | Nakajima |
| 8,251,950 B2 | 8/2012 | Albert et al. |
| 8,273,056 B2 | 9/2012 | Kuracina et al. |
| 8,277,424 B2 | 10/2012 | Pan |
| 8,287,518 B2 | 10/2012 | Kitani et al. |
| 8,298,195 B2 | 10/2012 | Peppel |
| 8,313,459 B2 | 11/2012 | Kiehne |
| 8,313,469 B2 | 11/2012 | Fiser |
| 8,323,249 B2 | 12/2012 | White et al. |
| 8,337,471 B2 | 12/2012 | Baid |
| 8,337,483 B2 | 12/2012 | Harding et al. |
| 8,357,121 B2 | 1/2013 | Burkholz |
| 8,361,408 B2 | 1/2013 | Lynn |
| 8,366,676 B2 | 2/2013 | Harding et al. |
| 8,377,010 B2 | 2/2013 | Harding et al. |
| 8,377,040 B2 | 2/2013 | Burkholz et al. |
| 8,382,718 B2 | 2/2013 | Woehr |
| 8,398,597 B2 | 3/2013 | Brimhall |
| 8,398,598 B2 | 3/2013 | Carlyon et al. |
| 8,403,894 B2 | 3/2013 | Lynn et al. |
| 8,403,905 B2 | 3/2013 | Yow |
| 8,408,226 B2 | 4/2013 | Raines et al. |
| 8,409,165 B2 | 4/2013 | Niedospial, Jr. et al. |
| 8,430,850 B2 | 4/2013 | Gyrn et al. |
| 8,439,877 B2 | 5/2013 | Burkholz |
| 8,439,891 B1 | 5/2013 | Milligan |
| 8,444,605 B2 | 5/2013 | Kuracina et al. |
| 8,465,441 B2 | 6/2013 | Srivatsa et al. |
| 8,529,524 B2 | 9/2013 | Newton et al. |
| 8,545,454 B2 | 10/2013 | Kuracina et al. |
| 8,556,854 B2 | 10/2013 | Zivkovic et al. |
| 8,556,855 B2 | 10/2013 | Zivkovic et al. |
| 8,568,372 B2 | 10/2013 | Woehr et al. |
| 8,591,469 B2 | 11/2013 | Keyser et al. |
| 8,622,967 B2 | 1/2014 | Davis et al. |
| 8,628,497 B2 | 1/2014 | Finnestad et al. |
| 8,636,697 B2 | 1/2014 | Scheurer et al. |
| 8,647,301 B2 | 2/2014 | Bialecki et al. |
| 8,657,788 B2 | 2/2014 | Fangrow, Jr. |
| 8,657,790 B2 | 2/2014 | Tal et al. |
| 8,663,169 B2 | 3/2014 | Emmert et al. |
| 8,668,674 B2 | 3/2014 | White et al. |
| 8,671,964 B2 | 3/2014 | Py |
| 8,684,994 B2 | 4/2014 | Lev et al. |
| 8,702,675 B2 | 4/2014 | Imai |
| 8,715,222 B2 | 5/2014 | Truitt et al. |
| 8,715,247 B2 | 5/2014 | Mansour et al. |
| 8,715,250 B2 | 5/2014 | Tremblay |
| 8,721,627 B2 | 5/2014 | Alpert |
| 8,728,035 B2 | 5/2014 | Warring et al. |
| 8,771,230 B2 | 7/2014 | White et al. |
| 8,784,387 B2 | 7/2014 | Woehr |
| 8,790,310 B2 | 7/2014 | White et al. |
| 8,801,678 B2 | 8/2014 | Panian et al. |
| 8,814,833 B2 | 8/2014 | Farrell et al. |
| 8,827,965 B2 | 9/2014 | Woehr et al. |
| 8,834,422 B2 | 9/2014 | Walker et al. |
| 8,834,432 B2 | 9/2014 | Winsor et al. |
| 8,840,577 B1 | 9/2014 | Zollinger et al. |
| 8,858,503 B2 | 10/2014 | Burkholz et al. |
| 8,870,835 B2 | 10/2014 | Baid |
| 8,870,846 B2 | 10/2014 | Davis et al. |
| 8,876,784 B2 | 11/2014 | Coete, Sr. et al. |
| 8,882,742 B2 | 11/2014 | Dikeman et al. |
| 8,900,192 B2 | 12/2014 | Anderson et al. |
| 8,900,199 B2 | 12/2014 | Kawai et al. |
| 8,910,919 B2 | 12/2014 | Bonnal et al. |
| 8,915,891 B2 | 12/2014 | Bornhoft |
| 8,932,259 B2 | 1/2015 | Stout et al. |
| 8,951,233 B2 | 2/2015 | Mansour |
| 8,956,328 B2 | 2/2015 | Antonucci |
| 8,956,330 B2 | 2/2015 | Fangrow, Jr. |
| 8,968,252 B2 | 3/2015 | White et al. |
| 8,968,261 B2 | 3/2015 | Kimball et al. |
| 8,968,271 B2 | 3/2015 | Guala |
| 8,974,425 B2 | 3/2015 | Tachizaki et al. |
| 8,979,795 B2 | 3/2015 | Bokelman et al. |
| 8,979,804 B2 | 3/2015 | Ho et al. |
| 8,986,227 B2 | 3/2015 | Belson |
| 8,998,851 B2 | 4/2015 | Constantineau et al. |
| 9,011,382 B2 | 4/2015 | Nilsson et al. |
| 9,017,288 B1 | 4/2015 | Starnes |
| 9,017,295 B2 | 4/2015 | Pan |
| 9,032,997 B2 | 5/2015 | Abura et al. |
| 9,033,927 B2 | 5/2015 | Maan et al. |
| 9,033,952 B2 | 5/2015 | Chen |
| 9,039,047 B2 | 5/2015 | Imai |
| 9,044,552 B2 | 6/2015 | Schraga |
| 9,044,585 B2 | 6/2015 | Masuda et al. |
| 9,050,128 B2 | 6/2015 | Ros |
| 9,056,188 B2 | 6/2015 | Hager et al. |
| 9,061,130 B2 | 6/2015 | Truitt et al. |
| 9,067,049 B2 | 6/2015 | Panian et al. |
| 9,089,680 B2 | 7/2015 | Ueda et al. |
| 9,089,681 B2 | 7/2015 | Ueda et al. |
| 9,089,682 B2 | 7/2015 | Yeh et al. |
| 9,095,679 B2 | 8/2015 | Nishimura et al. |
| 9,095,683 B2 | 8/2015 | Hall et al. |
| 9,114,231 B2 | 8/2015 | Woehr et al. |
| 9,114,241 B2 | 8/2015 | Stout et al. |
| 9,114,244 B2 | 8/2015 | Yeh et al. |
| 9,119,950 B2 | 9/2015 | Mansour et al. |
| 9,126,017 B2 | 9/2015 | Albert et al. |
| 9,138,572 B2 | 9/2015 | Zeytoonian et al. |
| 9,144,672 B2 | 9/2015 | Mansour et al. |
| 9,162,029 B2 | 10/2015 | Zollinger |
| 9,162,037 B2 | 10/2015 | Belson et al. |
| 9,198,831 B2 | 12/2015 | Rogers |
| 9,199,062 B2 | 12/2015 | Liska et al. |
| 9,199,063 B2 | 12/2015 | Baid |
| 9,212,772 B2 | 12/2015 | Ho et al. |
| 9,220,871 B2 | 12/2015 | Thörne et al. |
| 9,227,038 B2 | 1/2016 | Woehr |
| 9,233,229 B2 | 1/2016 | Emmert et al. |
| 9,234,616 B2 | 1/2016 | Carrez et al. |
| 9,238,128 B2 | 1/2016 | Yamaguchi et al. |
| 9,238,130 B2 | 1/2016 | Mouri |
| 9,259,533 B2 | 2/2016 | Weilbacher et al. |
| 9,259,537 B2 | 2/2016 | Baney et al. |
| 9,265,882 B2 | 2/2016 | Ito |
| 9,271,668 B2 | 3/2016 | Crawford et al. |
| 9,278,180 B2 | 3/2016 | Wong |
| 9,278,195 B2 | 3/2016 | Erskine |
| 9,289,237 B2 | 3/2016 | Woehr et al. |
| 9,289,588 B2 | 3/2016 | Chen |
| 9,308,352 B2 | 4/2016 | Teoh et al. |
| 9,308,353 B2 | 4/2016 | Shaw et al. |
| 9,308,354 B2 | 4/2016 | Farrell et al. |
| 9,314,604 B2 | 4/2016 | Bonnal et al. |
| 9,320,469 B2 | 4/2016 | Shaw et al. |
| 9,320,858 B2 | 4/2016 | Grimm et al. |
| 9,320,859 B2 | 4/2016 | Grimm et al. |
| 9,320,860 B2 | 4/2016 | Grimm et al. |
| 9,345,641 B2 | 5/2016 | Krause et al. |

(56) References Cited

U.S. PATENT DOCUMENTS

| | | |
|---|---|---|
| 9,352,127 B2 | 5/2016 | Yeh et al. |
| 9,370,466 B2 | 6/2016 | Garfield et al. |
| 9,370,641 B2 | 6/2016 | Woehr et al. |
| 9,370,651 B2 | 6/2016 | Zollinger et al. |
| 9,375,551 B2 | 6/2016 | Harding |
| 9,375,552 B2 | 6/2016 | Tremblay |
| 9,381,324 B2 | 7/2016 | Fuchs et al. |
| 9,381,337 B2 | 7/2016 | Carter et al. |
| 9,393,398 B2 | 7/2016 | Truitt et al. |
| 9,399,116 B2 | 7/2016 | Goral et al. |
| 9,399,119 B2 | 7/2016 | Kuracina et al. |
| 9,399,120 B2 | 7/2016 | Burkholz |
| 9,408,632 B2 | 8/2016 | Erskine |
| 9,409,007 B2 | 8/2016 | Yeh |
| 9,415,192 B2 | 8/2016 | Kuracina et al. |
| 9,421,345 B2 | 8/2016 | Woehr et al. |
| 9,421,352 B2 | 8/2016 | Butts et al. |
| 9,427,549 B2 | 8/2016 | Woehr et al. |
| 9,433,708 B2 | 9/2016 | Eddy |
| 9,433,758 B2 | 9/2016 | Farley et al. |
| 9,522,255 B2 | 12/2016 | Knutsson |
| 9,809,355 B2 | 11/2017 | Solomon et al. |
| 9,827,398 B2 | 11/2017 | White et al. |
| 2001/0041871 A1 | 11/2001 | Brimhall |
| 2002/0045843 A1 | 4/2002 | Barker et al. |
| 2002/0165497 A1 | 11/2002 | Greene et al. |
| 2003/0032922 A1 | 2/2003 | Moorehead |
| 2003/0073956 A1 | 4/2003 | Hoffman et al. |
| 2003/0083620 A1 | 5/2003 | Luther et al. |
| 2003/0083621 A1 | 5/2003 | Shaw et al. |
| 2003/0120222 A1 | 6/2003 | Vaillancourt |
| 2003/0181871 A1 | 9/2003 | Wilkinson et al. |
| 2003/0195479 A1 | 10/2003 | Kuracina et al. |
| 2003/0199827 A1 | 10/2003 | Thorne |
| 2004/0010227 A1 | 1/2004 | Riesenberger et al. |
| 2004/0106903 A1 | 1/2004 | Shue et al. |
| 2004/0030294 A1 | 2/2004 | Mahurkar |
| 2004/0064102 A1 | 4/2004 | Yamada |
| 2004/0097888 A1 | 5/2004 | Gutierrez |
| 2004/0102735 A1 | 5/2004 | Moulton et al. |
| 2004/0111059 A1 | 6/2004 | Howlett et al. |
| 2004/0116855 A1 | 6/2004 | Popov et al. |
| 2004/0127856 A1 | 7/2004 | Johnson |
| 2004/0143216 A1 | 7/2004 | Douglas et al. |
| 2004/0181192 A1 | 9/2004 | Cuppy |
| 2004/0206416 A1 | 10/2004 | Paradis |
| 2004/0267210 A1 | 12/2004 | Popovsky |
| 2005/0027263 A1 | 2/2005 | Woehr et al. |
| 2005/0043709 A1 | 2/2005 | Brimhall et al. |
| 2005/0045192 A1 | 3/2005 | Fulton et al. |
| 2005/0059933 A1 | 3/2005 | Johnson |
| 2005/0113755 A1 | 5/2005 | Greene et al. |
| 2005/0131350 A1 | 6/2005 | Shaw et al. |
| 2005/0192535 A1 | 9/2005 | Takagi et al. |
| 2006/0015071 A1* | 1/2006 | Fitzgerald ......... A61M 25/0606 604/168.01 |
| 2006/0015075 A1 | 1/2006 | Blanco et al. |
| 2006/0030815 A1 | 2/2006 | Csincsura et al. |
| 2006/0060892 A1 | 3/2006 | Hackler et al. |
| 2006/0094983 A1 | 5/2006 | Burbank et al. |
| 2006/0106335 A1 | 5/2006 | Putter et al. |
| 2006/0116638 A1 | 6/2006 | Woehr et al. |
| 2006/0155258 A1 | 7/2006 | Rogers et al. |
| 2006/0189942 A1 | 8/2006 | Chang et al. |
| 2006/0247577 A1 | 11/2006 | Wright |
| 2006/0264833 A1 | 11/2006 | Moulton |
| 2006/0270994 A1 | 11/2006 | Bierman |
| 2007/0016149 A1 | 1/2007 | Hunn et al. |
| 2007/0038179 A1 | 2/2007 | Bialecki et al. |
| 2007/0038182 A1 | 2/2007 | Bialecki et al. |
| 2007/0038183 A1 | 2/2007 | Bialecki et al. |
| 2007/0038185 A1 | 2/2007 | Albert et al. |
| 2007/0038186 A1 | 2/2007 | Sutton et al. |
| 2007/0038187 A1 | 2/2007 | Albert et al. |
| 2007/0066958 A1 | 3/2007 | Wright |
| 2007/0066960 A1 | 3/2007 | Jones et al. |
| 2007/0073221 A1 | 3/2007 | Bialecki et al. |
| 2007/0078400 A1 | 4/2007 | Gesler, III |
| 2007/0129689 A1 | 6/2007 | Woehr et al. |
| 2007/0142785 A1 | 6/2007 | Lundgaard et al. |
| 2007/0161950 A1 | 7/2007 | Carlyon et al. |
| 2007/0173768 A2 | 7/2007 | Bierman |
| 2007/0179446 A1 | 8/2007 | Carrez et al. |
| 2007/0185454 A1 | 8/2007 | Fangrow |
| 2007/0185455 A1 | 8/2007 | Fangrow |
| 2007/0191776 A1 | 8/2007 | Bialecki et al. |
| 2007/0191777 A1 | 8/2007 | King |
| 2007/0244438 A1 | 10/2007 | Perez |
| 2007/0250011 A1 | 10/2007 | Lee |
| 2007/0250057 A1 | 10/2007 | Nobis et al. |
| 2007/0255212 A1 | 11/2007 | Smith et al. |
| 2007/0265572 A1 | 11/2007 | Smith et al. |
| 2007/0270754 A1 | 11/2007 | Soderholm et al. |
| 2007/0270758 A1 | 11/2007 | Hanner et al. |
| 2008/0039796 A1 | 2/2008 | Nakajima |
| 2008/0051726 A1 | 2/2008 | Lee et al. |
| 2008/0097315 A1 | 4/2008 | Miner et al. |
| 2008/0125717 A1 | 5/2008 | Shue et al. |
| 2008/0132846 A1 | 6/2008 | Shue et al. |
| 2008/0135443 A1 | 6/2008 | Frojd et al. |
| 2008/0140004 A1 | 6/2008 | Thorne et al. |
| 2008/0140011 A1 | 6/2008 | Hager et al. |
| 2008/0147009 A1 | 6/2008 | Nilsson et al. |
| 2008/0195033 A1 | 8/2008 | Eagleson et al. |
| 2008/0215009 A1 | 9/2008 | Shaw et al. |
| 2008/0228144 A1 | 9/2008 | Liniger et al. |
| 2008/0262431 A1 | 10/2008 | Anderson et al. |
| 2008/0287876 A1 | 11/2008 | Shue et al. |
| 2008/0300543 A1 | 12/2008 | Abriles et al. |
| 2008/0300574 A1 | 12/2008 | Belson et al. |
| 2009/0012480 A1 | 1/2009 | Moulton et al. |
| 2009/0036836 A1 | 2/2009 | Nystrom et al. |
| 2009/0036914 A1 | 2/2009 | Houser |
| 2009/0043260 A1 | 2/2009 | Bierman |
| 2009/0069751 A1 | 3/2009 | Curtis et al. |
| 2009/0076435 A1 | 3/2009 | Melsheimer et al. |
| 2009/0082732 A1 | 3/2009 | Hillman |
| 2009/0082733 A1 | 3/2009 | Fujii |
| 2009/0124981 A1 | 5/2009 | Evans |
| 2009/0131870 A1 | 5/2009 | Fiser |
| 2009/0131872 A1 | 5/2009 | Popov |
| 2009/0137958 A1 | 5/2009 | Erskine |
| 2009/0137961 A1 | 5/2009 | Bracken |
| 2009/0163861 A1 | 6/2009 | Carlyon |
| 2009/0177167 A1 | 7/2009 | Kuracina et al. |
| 2009/0221961 A1 | 9/2009 | Tal et al. |
| 2009/0227896 A1 | 9/2009 | Tan et al. |
| 2009/0247952 A1 | 10/2009 | Weilbacher et al. |
| 2009/0299295 A1 | 12/2009 | Rubinstein et al. |
| 2009/0306602 A1 | 12/2009 | Elwell et al. |
| 2010/0004604 A1 | 1/2010 | Stearns |
| 2010/0016804 A1 | 1/2010 | Muskatello et al. |
| 2010/0036331 A1 | 2/2010 | Sen |
| 2010/0094310 A1 | 4/2010 | Warring et al. |
| 2010/0106135 A1 | 4/2010 | Radmand |
| 2010/0137815 A1 | 6/2010 | Kuracina et al. |
| 2010/0137833 A1 | 6/2010 | Glynn |
| 2010/0168675 A1 | 7/2010 | Cindrich et al. |
| 2010/0204648 A1 | 8/2010 | Stout et al. |
| 2010/0210934 A1 | 8/2010 | Belson |
| 2010/0222746 A1 | 9/2010 | Burkholz |
| 2010/0234804 A1 | 9/2010 | Hiejima et al. |
| 2010/0241088 A1 | 9/2010 | Ranalletta et al. |
| 2010/0262038 A1 | 10/2010 | Tan et al. |
| 2010/0262083 A1 | 10/2010 | Grunhut et al. |
| 2010/0268156 A1* | 10/2010 | Milacek ............ A61B 17/3415 604/30 |
| 2010/0274199 A1 | 10/2010 | Weston |
| 2010/0286615 A1 | 11/2010 | Gyrn et al. |
| 2010/0286620 A1 | 11/2010 | Edginton et al. |
| 2010/0286623 A1 | 11/2010 | Liversidge |
| 2010/0292673 A1 | 11/2010 | Korogi et al. |
| 2010/0305519 A1 | 12/2010 | McKinnon et al. |
| 2010/0318063 A1 | 12/2010 | Soll |

(56) References Cited

U.S. PATENT DOCUMENTS

| | | |
|---|---|---|
| 2011/0015573 A1 | 1/2011 | Maan et al. |
| 2011/0021994 A1 | 1/2011 | Anderson et al. |
| 2011/0054404 A1 | 3/2011 | Tanabe et al. |
| 2011/0060288 A1 | 3/2011 | Carlyon et al. |
| 2011/0077592 A1 | 3/2011 | Takemoto |
| 2011/0125096 A1 | 5/2011 | Baid |
| 2011/0125097 A1 | 5/2011 | Shaw et al. |
| 2011/0166475 A1 | 7/2011 | Crawford et al. |
| 2011/0178427 A1 | 7/2011 | Tan et al. |
| 2011/0178464 A1 | 7/2011 | Rawls |
| 2011/0178478 A1 | 7/2011 | Huet et al. |
| 2011/0196260 A1 | 8/2011 | Melsheimer et al. |
| 2011/0208124 A1 | 8/2011 | Rhad et al. |
| 2011/0213307 A1 | 9/2011 | Kawai et al. |
| 2011/0224617 A1 | 9/2011 | Miner |
| 2011/0306933 A1 | 12/2011 | Djordjevic et al. |
| 2011/0319859 A1 | 12/2011 | Zeytoonian et al. |
| 2012/0010577 A1 | 1/2012 | Liska et al. |
| 2012/0016312 A1 | 1/2012 | Brown et al. |
| 2012/0022464 A1 | 1/2012 | Zivkovic et al. |
| 2012/0191010 A1 | 1/2012 | Cabot |
| 2012/0035552 A1 | 2/2012 | Woehr |
| 2012/0041371 A1 | 2/2012 | Tal et al. |
| 2012/0041377 A1 | 2/2012 | Haak |
| 2012/0056746 A1 | 3/2012 | Kaigler et al. |
| 2012/0109077 A1 | 5/2012 | Ryan |
| 2012/0143151 A1 | 6/2012 | Low et al. |
| 2012/0150117 A1 | 6/2012 | Andino |
| 2012/0150121 A1 | 6/2012 | Silverman et al. |
| 2012/0153201 A1 | 6/2012 | Larose et al. |
| 2012/0184910 A1 | 7/2012 | Woehr |
| 2012/0197200 A1 | 8/2012 | Belson |
| 2012/0197205 A1 | 8/2012 | Peters |
| 2012/0220944 A1 | 8/2012 | Charlez |
| 2012/0220955 A1 | 8/2012 | Maseda et al. |
| 2012/0220984 A1 | 8/2012 | Christensen et al. |
| 2012/0226240 A1 | 9/2012 | Bedford et al. |
| 2012/0259293 A1 | 10/2012 | Bialecki et al. |
| 2012/0316536 A1 | 12/2012 | Carrez et al. |
| 2012/0323181 A1 | 12/2012 | Shaw et al. |
| 2012/0330248 A1 | 12/2012 | Woehr |
| 2013/0030370 A1 | 1/2013 | Walker et al. |
| 2013/0041313 A1* | 2/2013 | Chung ............... A61M 1/008 604/31 |
| 2013/0053781 A1 | 2/2013 | Woehr et al. |
| 2013/0053815 A1 | 2/2013 | Mucientes et al. |
| 2013/0060201 A1 | 3/2013 | Popov |
| 2013/0060205 A1 | 3/2013 | Mansour et al. |
| 2013/0066276 A1 | 3/2013 | Ito et al. |
| 2013/0079730 A1 | 3/2013 | Mosler et al. |
| 2013/0110036 A1 | 5/2013 | Fojtik |
| 2013/0116598 A1 | 5/2013 | Howell et al. |
| 2013/0150784 A1 | 6/2013 | Rodriguez Lelis et al. |
| 2013/0158506 A1 | 6/2013 | White et al. |
| 2013/0178798 A1 | 7/2013 | Pearson et al. |
| 2013/0178825 A1 | 7/2013 | Helm, Jr. |
| 2013/0211325 A1 | 8/2013 | Wang et al. |
| 2013/0226144 A1 | 8/2013 | Milligan |
| 2013/0231630 A1 | 9/2013 | Krause et al. |
| 2013/0261554 A1 | 10/2013 | Baid |
| 2013/0296808 A1 | 11/2013 | Triplett et al. |
| 2014/0012196 A1 | 1/2014 | Zivkovic et al. |
| 2014/0012206 A1 | 1/2014 | Shaw et al. |
| 2014/0025036 A1 | 1/2014 | Bierman et al. |
| 2014/0039399 A1 | 2/2014 | Burkholz |
| 2014/0052065 A1 | 2/2014 | Woehr et al. |
| 2014/0058329 A1 | 2/2014 | Walker et al. |
| 2014/0058357 A1 | 2/2014 | Keyser et al. |
| 2014/0074032 A1 | 3/2014 | Bornhoft |
| 2014/0081210 A1 | 3/2014 | Bierman et al. |
| 2014/0100528 A1 | 4/2014 | Finnestad et al. |
| 2014/0135702 A1 | 5/2014 | Woehr et al. |
| 2014/0135703 A1 | 5/2014 | Yeh et al. |
| 2014/0151083 A1 | 6/2014 | White et al. |
| 2014/0163470 A1 | 6/2014 | Baid |
| 2014/0163523 A1 | 6/2014 | Constantineau et al. |
| 2014/0171876 A1 | 6/2014 | Shaw et al. |
| 2014/0174578 A1 | 6/2014 | Bonnal et al. |
| 2014/0180212 A1 | 6/2014 | Baid |
| 2014/0180219 A1 | 6/2014 | Ho et al. |
| 2014/0180250 A1 | 6/2014 | Belson |
| 2014/0180258 A1 | 6/2014 | Ho et al. |
| 2014/0188003 A1 | 7/2014 | Belson |
| 2014/0209197 A1 | 7/2014 | Carrez et al. |
| 2014/0221931 A1 | 8/2014 | Kuracina et al. |
| 2014/0257202 A1 | 9/2014 | Woehr |
| 2014/0261860 A1 | 9/2014 | Heath et al. |
| 2014/0276453 A1 | 9/2014 | Woehr |
| 2014/0276455 A1 | 9/2014 | Yeh et al. |
| 2014/0276458 A1 | 9/2014 | Mansour et al. |
| 2014/0276459 A1 | 9/2014 | Yeh et al. |
| 2014/0276462 A1 | 9/2014 | Vincent et al. |
| 2014/0276463 A1 | 9/2014 | Mansour et al. |
| 2014/0276466 A1 | 9/2014 | Yeh et al. |
| 2014/0296794 A1 | 10/2014 | Li |
| 2014/0296829 A1 | 10/2014 | White et al. |
| 2014/0303561 A1 | 10/2014 | Li |
| 2014/0316350 A1 | 10/2014 | Yamaguchi et al. |
| 2014/0323980 A1 | 10/2014 | Cronenberg et al. |
| 2014/0336582 A1 | 11/2014 | Tisci et al. |
| 2014/0336583 A1 | 11/2014 | Morrissey et al. |
| 2014/0358033 A1 | 12/2014 | Lynn |
| 2014/0364809 A1 | 12/2014 | Isaacson et al. |
| 2014/0371686 A1 | 12/2014 | Sano et al. |
| 2015/0005718 A1 | 1/2015 | Walker et al. |
| 2015/0038943 A1 | 2/2015 | Warring et al. |
| 2015/0045746 A1 | 2/2015 | Macy, Jr. et al. |
| 2015/0073304 A1 | 3/2015 | Miller |
| 2015/0080801 A1 | 3/2015 | Tanabe et al. |
| 2015/0148748 A1 | 5/2015 | Shluzas et al. |
| 2015/0148749 A1 | 5/2015 | Cohn |
| 2015/0148756 A1 | 5/2015 | Lynn |
| 2015/0151083 A1 | 6/2015 | White et al. |
| 2015/0157799 A1 | 6/2015 | Chen et al. |
| 2015/0157800 A1 | 6/2015 | Chen et al. |
| 2015/0157848 A1 | 6/2015 | Wu et al. |
| 2015/0165132 A1 | 6/2015 | Perot et al. |
| 2015/0174339 A1 | 6/2015 | Bokelman et al. |
| 2015/0174374 A1 | 6/2015 | Woehr |
| 2015/0190168 A1 | 7/2015 | Bierman et al. |
| 2015/0190627 A1 | 7/2015 | Ueda et al. |
| 2015/0196737 A1 | 7/2015 | Baid |
| 2015/0196749 A1 | 7/2015 | Ziv et al. |
| 2015/0196750 A1 | 7/2015 | Ueda et al. |
| 2015/0202424 A1 | 7/2015 | Harton |
| 2015/0209508 A1 | 7/2015 | Constantineu et al. |
| 2015/0224267 A1 | 8/2015 | Farrell et al. |
| 2015/0258325 A1 | 9/2015 | Panian et al. |
| 2015/0265829 A1 | 9/2015 | Truitt et al. |
| 2015/0290431 A1 | 10/2015 | Hall et al. |
| 2015/0297817 A1 | 10/2015 | Guala |
| 2015/0297880 A1 | 10/2015 | Ogawa et al. |
| 2015/0313523 A1 | 11/2015 | Chelak et al. |
| 2015/0328438 A1 | 11/2015 | Baid |
| 2015/0352331 A1 | 12/2015 | Helm, Jr. |
| 2015/0352333 A1 | 12/2015 | Arellano Cabrera et al. |
| 2016/0000364 A1 | 1/2016 | Mendels et al. |
| 2016/0001057 A1 | 1/2016 | Lopez et al. |
| 2016/0015943 A1 | 1/2016 | Belson et al. |
| 2016/0015945 A1 | 1/2016 | Warring et al. |
| 2016/0015958 A1 | 1/2016 | Ueda et al. |
| 2016/0015961 A1 | 1/2016 | Mansour et al. |
| 2016/0022963 A1 | 1/2016 | Belson |
| 2016/0022977 A1 | 1/2016 | Ueda et al. |
| 2016/0022978 A1 | 1/2016 | Ueda |
| 2016/0030730 A1 | 2/2016 | Mosler et al. |
| 2016/0038730 A1 | 2/2016 | Zollinger |
| 2016/0088995 A1 | 3/2016 | Ueda et al. |
| 2016/0114136 A1 | 4/2016 | Woehr et al. |
| 2016/0114147 A1 | 4/2016 | Slopes et al. |
| 2016/0121082 A1 | 5/2016 | Emmert et al. |
| 2016/0129180 A1 | 5/2016 | Roman et al. |
| 2016/0135841 A1 | 5/2016 | Albert et al. |
| 2016/0136051 A1 | 5/2016 | Lavi |

(56) References Cited

U.S. PATENT DOCUMENTS

| | | |
|---|---|---|
| 2016/0158498 A1 | 6/2016 | White et al. |
| 2016/0158499 A1 | 6/2016 | Helm |
| 2016/0158524 A1 | 6/2016 | Quach et al. |
| 2016/0183976 A1 | 6/2016 | Bertoli et al. |
| 2016/0199575 A1 | 7/2016 | Belley et al. |
| 2016/0206813 A1 | 7/2016 | Abe et al. |
| 2016/0206858 A1 | 7/2016 | Ishida |
| 2016/0220270 A1 | 8/2016 | Tamura et al. |
| 2016/0235944 A1 | 8/2016 | Ma |
| 2016/0235949 A1 | 8/2016 | Baid |
| 2016/0235961 A1 | 8/2016 | Maffei |
| 2016/0256667 A1 | 9/2016 | Ribelin et al. |
| 2016/0263353 A1 | 9/2016 | Kuracina et al. |
| 2016/0271370 A1 | 9/2016 | Keyser et al. |
| 2016/0296724 A1 | 10/2016 | Goral et al. |
| 2016/0325078 A1 | 11/2016 | Burkholz |
| 2017/0000983 A1 | 1/2017 | Woehr |
| 2017/0239443 A1 | 8/2017 | Abitabilo et al. |
| 2018/0154119 A1 | 6/2018 | White |

FOREIGN PATENT DOCUMENTS

| | | |
|---|---|---|
| EP | 1 323 442 | 7/2003 |
| JP | H06-78999 A | 3/1994 |
| JP | 2901915 B2 | 6/1999 |
| JP | 4211858 B2 | 1/2009 |
| WO | WO 1990/01351 | 2/1990 |
| WO | WO 1997/015342 | 5/1997 |
| WO | WO 2006/082350 | 8/2006 |
| WO | WO 2006/090148 | 8/2006 |
| WO | WO 2007/008511 | 1/2007 |
| WO | WO 2007/143555 | 12/2007 |
| WO | WO 2008/042285 | 4/2008 |
| WO | WO 2009/032008 | 3/2009 |
| WO | WO 2009/092076 | 7/2009 |
| WO | WO 2011/019985 | 2/2011 |
| WO | WO 2011/146764 | 11/2011 |
| WO | WO 2011/146769 | 11/2011 |
| WO | WO 2011/146772 | 11/2011 |
| WO | WO 2011/146781 | 11/2011 |
| WO | WO 2015/119940 | 8/2015 |
| WO | WO 2018/009653 | 1/2018 |

OTHER PUBLICATIONS

U.S. Appl. No. 15/427,714, filed Feb. 8, 2017, White et al.
International Preliminary Report on Patentability, re PCT Application No. PCT/US2015/014240, dated Aug. 9, 2016.
BD Nexvia Closed IV Catheter System, http://www.bd.com/infusion/products/ivcatheters/nexiva/index.asp, downloaded Sep. 6, 2013 in 19 pages.
European Extended Search Report, re EP Application No. 15746055.1, dated Nov. 29, 2017.

* cited by examiner

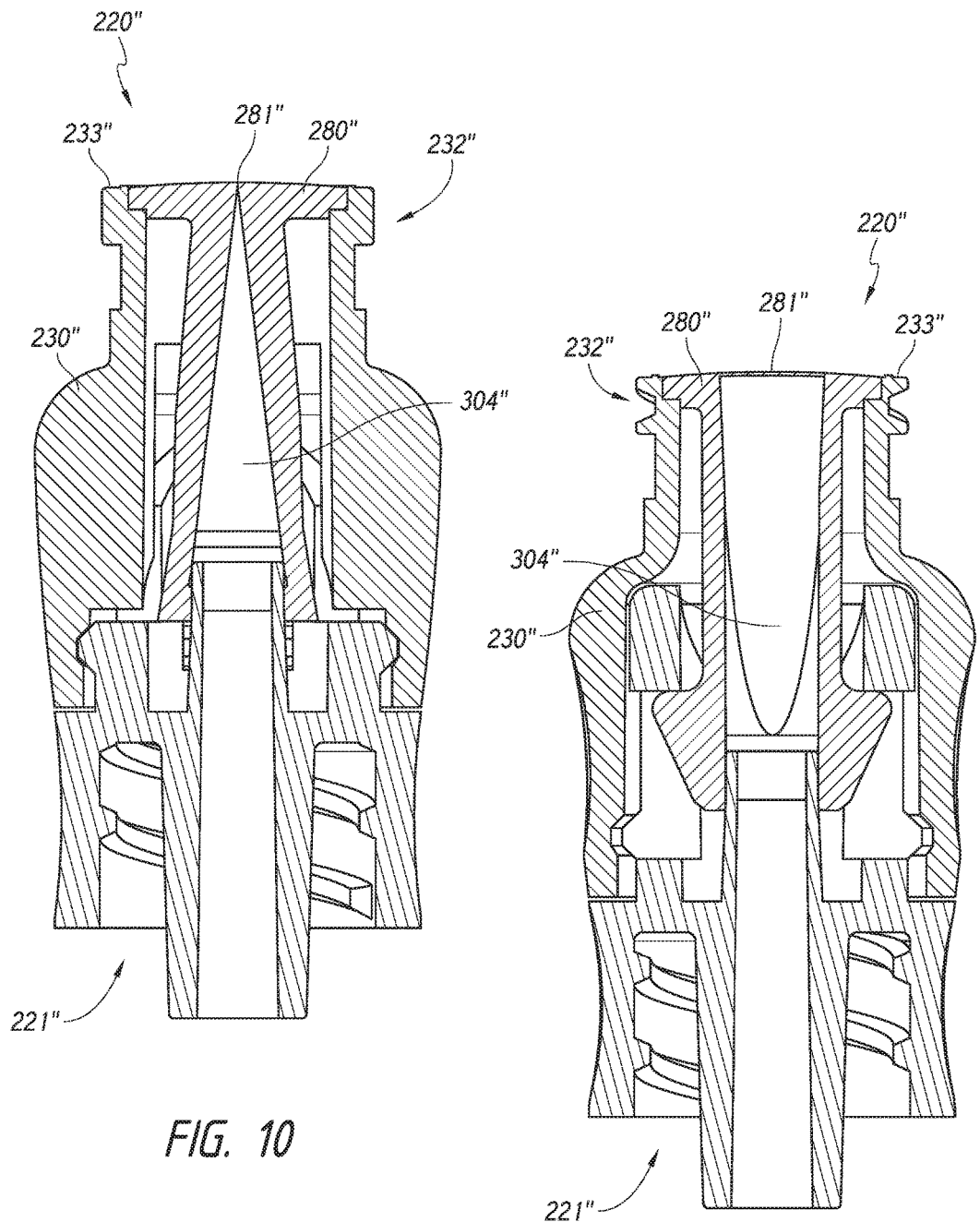

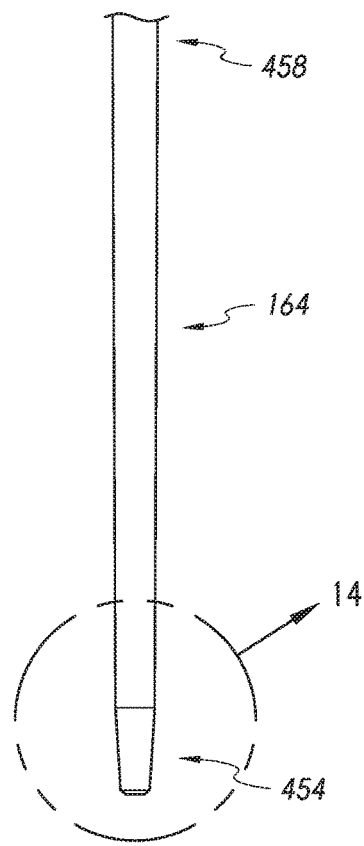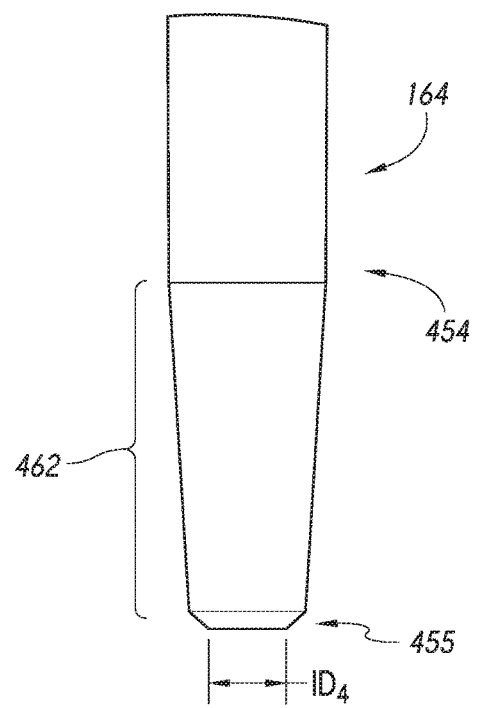
FIG. 13
FIG. 14

SELF-PRIMING SYSTEMS AND METHODS

RELATED APPLICATIONS

This application is a continuation of International Patent App. No. PCT/US2015/014240, filed Feb. 3, 2015, titled SELF-PRIMING SYSTEMS AND METHODS, which claims the benefit of U.S. Provisional Application No. 61/935,802, filed Feb. 4, 2014, titled SELF-PRIMING SYSTEMS AND METHODS. The entire contents of the above-identified patent applications are incorporated by reference herein and made a part of this specification.

This application also hereby incorporates by reference the entire disclosures of U.S. patent application Ser. No. 14/199,836, entitled "MEDICAL CONNECTORS WITH FLUID-RESISTANT MATING INTERFACES," filed on Mar. 6, 2014, now published as US-2014-0246616 A1, and of International Patent Application Serial No. PCT/US2013/069312, entitled "MEDICAL CONNECTOR," filed on Nov. 8, 2013, now published as WO 2014/074929.

BACKGROUND

Field

Certain embodiments disclosed herein relate to vascular access systems and methods. Some embodiments relate to systems and methods to remove fluid from vascular access systems.

Description of the Related Art

In various medical procedures, medical professionals need to access patients' veins and/or arteries. For example, a peripheral venous catheter, a central venous catheter, or another tube can be placed into a vein. Once in the vein, the catheter can be used to deliver medication or fluids. The catheter can also be used to draw blood samples.

Vascular access can include placing a needle in a vein. The needle can then be removed while a tube (e.g., a cannula) remains in the vein and provides a fluid path between the vein and an external assembly.

Gas embolism is one potential complication associated with vascular access. Gas, such as air, located inside of a vascular access device can enter a patient's blood (i.e., circulatory system). During venous access, most gas emboli are stopped by the lungs, which can reduce the likelihood of complications. Gas emboli during arterial access can result in higher complication rates. In spite of advances in medical equipment and procedures, gas embolism remains a significant risk. Thus, there is a need for medical equipment and procedures that reduce the risk of gas embolism.

BRIEF SUMMARY

In various embodiments described herein, a vascular access system can be configured to remove gas and to remove at least a portion of a piercing member from a vascular access system. In some embodiments, removal of gas and of the piercing member can be performed by the same action, such as by withdrawing a plunger. This can help minimize the possibility of operator error and increase the efficiency of a procedure. In some embodiments, gas can be removed first and the piercing member can be removed second. In some embodiments, the piercing member can remain fixed while gas is removed. In some embodiments, removal of gas and of the piercing member can occur simultaneously. In some embodiments, a vascular access system can be configured such that the same action that removes gas can also draw blood into the vascular access system to confirm proper placement of the piercing member. In various embodiments blood can be drawn into the vascular access system simultaneously with or before removing a piercing member from a vascular access system. In some embodiments, blood can be drawn into the vascular access system while the piercing member remains fixed within the vascular access system. These various embodiments can further increase the efficiency of the system and minimize the risk of errors.

In some embodiments, blood can also be drawn into the vascular access system to prime a medical connector, such as a needleless medical connector. Relying on a patient's own blood to prime the medical connector can minimize the steps required to use the vascular access system. In various embodiments, blood can be drawn into a medical connector to prime the medical connector with the same actions used to remove gas and/or draw blood to confirm placement of the piercing member. In some embodiments, a medical connector can be primed or partially primed while a piercing member remains fixed within the vascular access system. In some embodiments, a medical connector can be primed or partially primed before a piercing member is removed from the vascular access system.

In some embodiments, a vascular access system can comprise a first barrel, second barrel, and a plunger. The plunger can comprise a first shaft and a second shaft, wherein the first shaft is slidably coupled inside at least a portion of the first barrel between a first position and a second position, and the second shaft is slidably coupled inside at least a proximal portion of the second barrel between a first position and a second position. A vascular access system can comprise a piercing member coupled to the second shaft, the piercing member movable from a first position in which a distal tip of the piercing member extends from a distal portion of the second barrel to a second position in which the distal tip is retracted into the second barrel. A vascular access system can comprise a first reservoir located inside of the first barrel such that sliding the first shaft proximally relative to the first barrel increases a volume of the first reservoir. In several embodiments, the plunger is configured such that moving the plunger proximally relative to the first barrel simultaneously retracts the piercing member and increases the volume of the first reservoir.

In some embodiments, the first barrel and the second barrel are oriented parallel relative to each other or at an angle relative to each other. The first barrel can be located in a first position that is fixed relative to the second barrel. The first barrel can comprise a first central axis and the second barrel can comprise a second central axis. An angle between the first central axis and the second central axis can be less than or equal to about 25 degrees.

In several embodiments, a vascular access system comprises a plunger handle coupled to the first shaft and to the second shaft such that moving the plunger handle proximally increases the volume of the first reservoir and at least partially retracts the piercing member. The plunger can comprise a third shaft and a protrusion coupled to a distal portion of the third shaft. The protrusion can extend perpendicularly relative to the third shaft. The first shaft, the second shaft, and the third shaft can be oriented parallel relative to each other or they can be angled relative to each other.

In some embodiments, the piercing member remains in the first position until the volume of the first reservoir has been increased by a threshold volume. In some cases, the piercing member moves to the second position when the volume of the first reservoir has been increased by a volume greater than the threshold volume. In some cases the threshold volume is greater than 1 cubic centimeter. According to some variants, when the piercing member is in the first position the distal tip of the piercing member is a generally constant distance from the distal portion of the second barrel. In some embodiments, the second barrel comprises flexible locking arms having a locked position configured to lock the piercing member axially relative to the second barrel and an unlocked position in which the piercing member can move axially relative to the second barrel. In some cases, a biasing member couples the piercing member to the second shaft. According to some variants, the vascular access system includes a piercing member holder coupling the piercing member to the biasing member.

In some embodiments, a vascular access system can be configured to concurrently remove gas and a piercing member from a catheter assembly. A vascular access system can comprise a catheter comprising a first passage and a piercing member oriented coaxially with the first passage. The piercing member can be configured to slide out of the first passage of the catheter. A vascular access system can comprise a fluid removal syringe comprising a fluid reservoir and a plunger. The fluid removal syringe can be configured such that sliding the plunger proximally expands the fluid reservoir. The plunger can be coupled to the piercing member such that sliding the plunger proximally causes the piercing member to retract proximally. The system can include a second passage that fluidly couples the first passage radially outward to the fluid removal syringe. The second passage can be configured such that fluid can flow radially outward from the first passage to the fluid removal syringe.

Some embodiments include a guide having a funnel portion, a cylindrical portion, and an inner channel. The proximal portion of the catheter can be located inside of the cylindrical portion of the guide. The guide can be configured to direct the piercing member towards the catheter as the piercing member passes through the inner channel of the guide. The guide can be metal or plastic.

In several embodiments, a vascular access system can comprise a plunger handle and a syringe. The syringe can comprise a plunger and a fluid reservoir having a volume. The plunger can be coupled to the plunger handle. The syringe can be configured such that moving the plunger proximally increases the volume of the fluid reservoir. A piercing member can be coupled to a shaft that is coupled to the plunger handle. The shaft can be coaxial with the piercing member. The syringe can be located radially outward from the shaft and beside the shaft. A vascular access system can comprise a catheter wherein at least a portion of the piercing member can be located inside of the catheter.

In some embodiments, a piercing member can comprise a needle having a distal tip and a solid proximal portion. The needle can comprise a passage that fluidly couples a first hole in the distal tip with a second hole located proximally relative to the distal tip. The second hole can be located distally relative to the solid proximal portion.

Several embodiments include a housing that couples a catheter to a syringe. A catheter can be coaxial with the piercing member. Some embodiments include a lever arm having a distal portion located distally relative to a pivot and a proximal portion located proximally relative to the pivot. The pivot can couple the lever arm to the syringe. The syringe can comprise a central axis. The distal portion of the lever arm can comprise a first tooth that extends perpendicularly relative to the central axis. The housing can comprise a second tooth that extends perpendicularly relative to the central axis. The first tooth can be configured to contact the second tooth to limit proximal movement of the syringe relative to the housing. The first tooth can extend radially inward relative to the central axis. The second tooth can extend radially outward relative to the central axis. The lever arm can be configured such that pressing the proximal portion of the lever arm radially inward can move the first tooth radially outward such that the first tooth no longer limits the proximal movement of the syringe. A plunger handle can comprise a slidable blocking bar located radially inward from the proximal portion of the lever arm. The blocking bar can be in a distal position to inhibit or prevent the proximal portion of the lever arm from moving radially inward far enough to allow the first tooth to no longer limit the proximal movement of the syringe relative to the housing.

In several embodiments, a syringe can comprise a central axis. The distal portion of the lever arm can comprise a first tooth. The housing can comprise a distally facing surface oriented at an angle within about 75 degrees to about 105 degrees relative to the central axis. The first tooth of the lever arm can contact the distally facing surface such that the first tooth can be configured to limit proximal motion of the syringe relative to the housing unless the proximal portion of the lever arm is moved radially to move the first tooth away from the distally facing surface.

In some embodiments, the syringe can comprise a flow controller. The distal portion of the lever arm can comprise a second tooth located proximally relative to the first tooth. A proximal protrusion can hold the flow controller in an open position.

In several embodiments, the distal portion of the lever arm can comprise a first tooth and a second tooth. The second tooth can be located proximally relative to the first tooth. The housing can comprise a distally facing surface oriented at an angle within about 75 degrees to about 105 degrees relative to the central axis of the syringe. The second tooth of the lever arm can be attached to the distally facing surface such that the second tooth is configured to limit proximal motion of the syringe relative to the housing. Contact between the second tooth and the distally facing surface can press a proximal protrusion against the flow controller to hold the flow controller in an open position.

In some embodiments, a barrel can be oriented coaxially with the piercing member. A portion of the shaft can be located inside of the barrel. The plunger handle can be located proximally relative to the barrel. The syringe can be located outside of the barrel. The piercing member can be configured to retract into the barrel.

Some embodiments include a ratchet assembly configured to allow proximal motion of the plunger handle relative to the syringe and/or configured to block, prevent, and/or inhibit distal motion of the plunger handle relative to the syringe. The ratchet assembly can comprise a linear rack coupled to the plunger handle and a pawl coupled to the syringe. In some embodiments, the ratchet assembly can comprise a linear rack coupled to the syringe and a pawl coupled to the plunger handle. The linear rack can comprise at least two teeth, at least three teeth, or at least five teeth. The pawl can comprise a protrusion that extends towards the teeth of the linear rack. Each of the three teeth can comprise a distal face oriented at an angle of greater than or equal to about 115 degrees and/or less than or equal to about 155 degrees relative to a distal end of a central axis of the syringe.

In several embodiments, a vascular access system can be configured to concurrently remove gas and at least a portion of a piercing member from a vascular access assembly. A vascular access system can include a plunger assembly comprising a first plunger and a shaft. The shaft can be located radially outward from the first plunger. The first plunger and the shaft can be coupled by a base. The first plunger and/or the shaft can extend distally from the base.

Some embodiments include a syringe comprising a fluid reservoir having a volume. At least a portion of the first plunger can be located inside of the syringe. The syringe can be configured such that moving the first plunger proximally relative to the syringe can increase the volume of the fluid reservoir. A first passage can be located in a catheter. A second passage can be located in a connector that can couple the catheter to the syringe. The second passage can be configured to be placed in fluid communication with the fluid reservoir. A third passage can be configured to fluidly couple the first passage to the second passage to enable fluid communication from the first passage to the fluid reservoir. A piercing member can be coupled to the shaft of the plunger assembly. The piercing member can be located at least partially inside of the first passage. The piercing member can be configured to retract proximally out of the first passage. The vascular access system can be configured such that moving the plunger assembly proximally relative to the syringe concurrently proximally retracts the piercing member and communicates fluid from the first passage to the fluid reservoir.

In several embodiments, the second passage can be oriented parallel to the first passage and/or the third passage can be oriented perpendicular to the first passage. Some embodiments comprise a tube that couples the connector to the catheter. At least a portion of the third passage can be located inside of the tube. A clamp can removably couple the connector to the catheter. The clamp can be a C-shaped clamp.

In some embodiments, a housing can have a distal passage and a proximal passage. The tube can comprise a first end located in the proximal passage. The tube can comprise a second end coupled to the connector. At least a proximal portion of the catheter can be located in the distal passage of the housing. The distal passage and the proximal passage can be oriented at an angle relative to each other. The angle can be at least about 25 degrees and/or less than about 70 degrees.

In some embodiments, the connector can comprise a flow controller capable of opening and closing at least a portion of the second passage. The flow controller can comprise a seal configured to block, obstruct, occlude, and/or cover an exit from the second passage.

In several embodiments, a method to remove gas and a piercing member from a vascular access assembly can include obtaining a syringe comprising a barrel, a plunger, and a fluid reservoir having a volume. The piercing member can be coupled to the plunger. The syringe can be configured such that moving the plunger proximally relative to the barrel increases the volume of the fluid reservoir and moves the piercing member proximally relative to the barrel. Some methods include obtaining a catheter comprising a passage configured to communicate fluid to the fluid reservoir. Several methods include opening a channel between the fluid reservoir and the passage of the catheter by moving the syringe distally relative to the catheter.

Some methods include extending the piercing member from a distal end of the catheter and/or inserting the piercing member into a patient. Several methods include retracting the piercing member proximally relative to the catheter while removing the gas from the channel.

In some embodiments, methods include determining if blood from the patient is flowing into the passage and/or determining if blood from the patient is flowing into the fluid reservoir. Opening the channel can comprise moving the plunger distally relative to the catheter. Opening the channel can comprise moving a flow controller to an open position. The flow controller can comprise a seal configured to block an exit of the channel. Opening the channel can comprise compressing the seal to unblock the exit. Some methods include locking the channel in an open position to allow fluid communication between the passage of the catheter and the fluid reservoir.

In some embodiments, retracting the piercing member proximally relative to the catheter while removing the gas from the channel can comprise moving the plunger proximally while activating a one-way ratchet assembly configured to allow proximal movement while blocking, impeding, preventing, and/or inhibiting distal movement of the plunger relative to the barrel. The one-way ratchet assembly can include teeth and/or a pawl.

Several methods include disengaging a lock that couples the syringe to the catheter and then decoupling the syringe from the catheter. The lock can include at least one tooth and/or protrusion that contacts and/or interferes with a surface, which can be a distally facing surface.

In various embodiments, a method of using a vascular access system to place a catheter in a patient can include providing a vascular access system that includes a plunger housing, a plunger assembly slidably positioned within the plunger housing, a catheter housing connected to the plunger housing, a catheter connected to the catheter housing, and a piercing member having a first position in which the piercing member extends through the catheter and a distal tip of the piercing member is outside of the catheter. The piercing member and catheter can be inserted into a blood vessel of a patient. The plunger assembly can be drawn proximally relative to the plunger housing to draw blood into the catheter while the piercing member remains in the first position. In some embodiments, the plunger assembly can be drawn proximally relative to the plunger housing to retract the distal tip of the piercing member into the plunger housing. The catheter housing can then be disconnected from the plunger housing.

Several methods include drawing blood into the piercing member when drawing blood into the catheter. Some methods include confirming that blood is drawn into the catheter before continuing to draw the plunger assembly proximally relative to the plunger housing to retract the distal tip of the piercing member into the plunger housing. In some embodiments, the vascular access system further comprises a medical connector connected to the catheter housing and to the plunger housing. In some cases, the method comprises drawing the plunger assembly proximally relative to the plunger housing to prime the medical connector. Several methods include disconnecting the medical connector from the plunger housing. In some embodiments, methods the plunger assembly is drawn proximally relative to the plunger housing to prime the medical connector after the plunger assembly is drawn proximally relative to the plunger housing to retract the distal tip of the piercing member into the plunger housing. In some cases, the distal tip of the piercing member is a first distance from the catheter when the piercing member is in the first position.

BRIEF DESCRIPTION OF THE DRAWINGS

Various embodiments are depicted in the accompanying drawings for illustrative purposes, and should in no way be interpreted as limiting the scope of the embodiments. In addition, various features of different disclosed embodiments can be combined to form additional embodiments, which are part of this disclosure.

FIG. 10 illustrates a cross-sectional view of a connector, according to some embodiments.

FIG. 11 illustrates a cross-sectional view of the connector of FIG. 10, rotated 90 degrees.

FIG. 13 illustrates a side view of a catheter, according to some embodiments.

FIG. 14 illustrates a side view of the distal portion of the catheter from FIG. 13, according to some embodiments.

DETAILED DESCRIPTION

Figure 1:
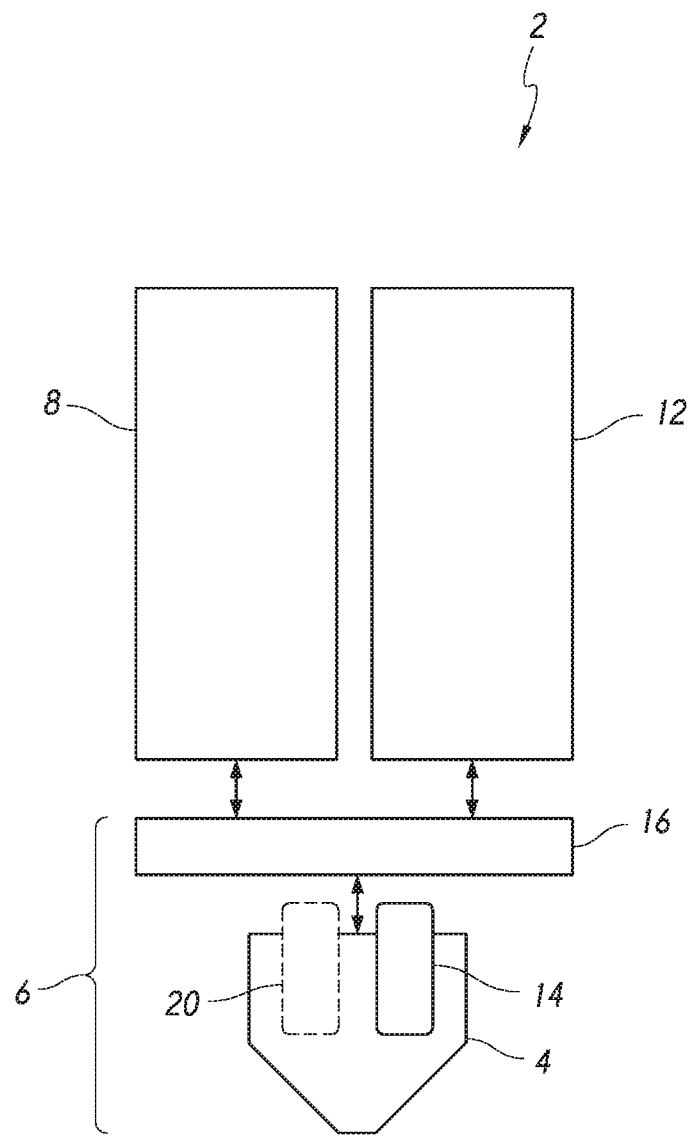
FIG. 1 schematically illustrates a vascular access system that can enable a medical professional to access a patient's vascular system, according to some embodiments.

Although certain embodiments and examples are disclosed herein, inventive subject matter extends beyond the examples in the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. No feature, benefit, advantage, structure, or step disclosed herein is essential or indispensable.

The drawings illustrate certain embodiments and are not intended to be limiting. The drawings can be semi-diagrammatic and not to scale. For clarity of presentation and discussion, some portions of and/or dimensions in the drawings are shown greatly exaggerated. In some instances, certain relative characteristics (e.g., height ratios, angles, proportional distances, width ratios, etc.) of the illustrated embodiments are presented in a proportionally accurate manner, independent of the scale of the overall Figures in which those embodiments are illustrated.

For expository purposes, the term "horizontal" as used herein is defined as a plane parallel to the plane or surface of the floor of the area in which the device being described is used or the method being described is performed, regardless of its orientation. The term "floor" can be interchanged with the term "ground." The term "vertical" refers to a direction perpendicular to the horizontal as just defined. Terms such as "above," "below," "bottom," "top," "side," "higher," "lower," "upper," "over," and "under," are defined with respect to the horizontal plane unless otherwise indicated.

FIG. 1 schematically illustrates a vascular access system 2 that can enable a medical professional to access a patient's vascular system (e.g., a circulatory system). Vascular access can enable a medical professional to deliver medication or fluids to a patient's circulatory system. Vascular access can also be used to draw blood samples.

A vascular access system 2 can include a vascular access assembly 6 configured to provide a fluid path between a portion of the circulatory system (e.g., a vein, an artery) and a device located externally to the patient's body (e.g., a catheter, a tube, a syringe barrel, an intravenous therapy bag). The vascular access system 6 can include a transcutaneous assembly 4 configured to enable a medical professional to pierce a patient's skin and enter a vein or artery. Some transcutaneous assemblies 4 include an access assembly 14, which can include a piercing member such as a needle. Needles can be made from a medical-grade metal. Some transcutaneous assemblies 4 do not include needles. In some embodiments, piercing members are made from plastic (e.g., with a hardness of about 75 Shore D to about 90 Shore D).

Figure 2:
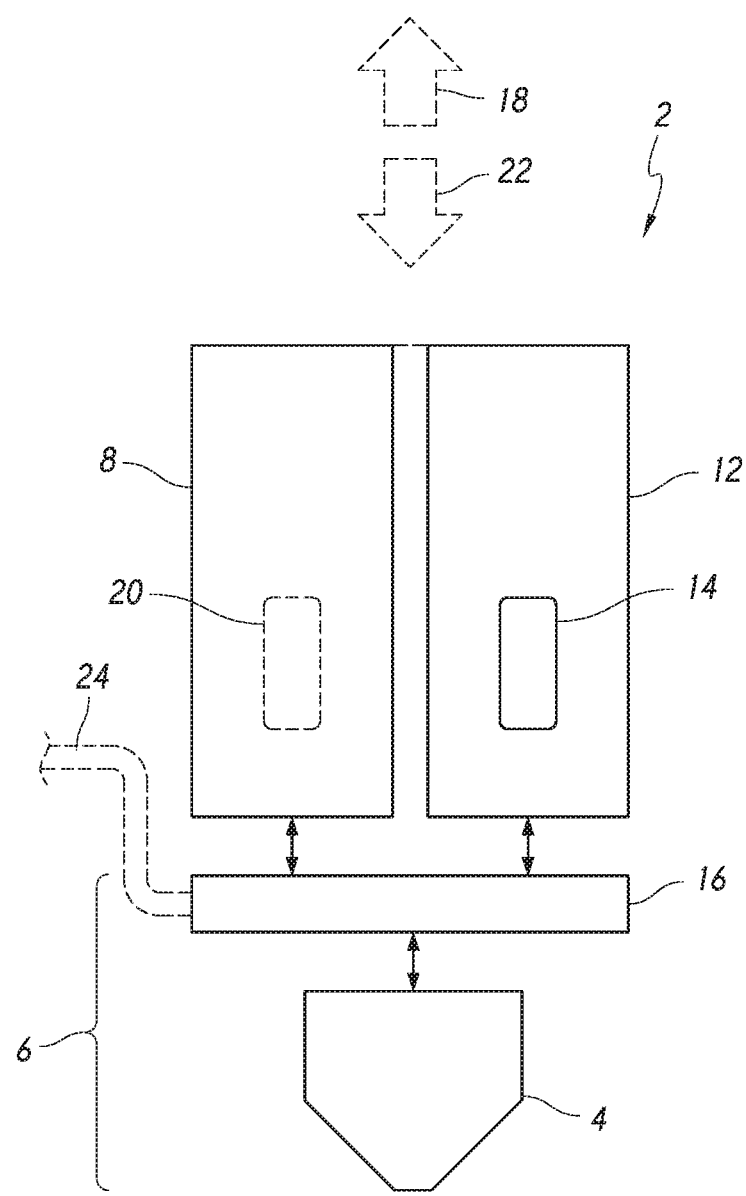
FIG. 2 schematically illustrates a vascular access system after a fluid extraction assembly has moved fluid into a portion of the fluid extraction assembly, according to some embodiments.

Prior to insertion into a patient, some vascular access assemblies 6 include fluid 20 (e.g., gas, air). If this fluid 20 is allowed to enter the circulatory system (e.g., the blood inside the patient), the fluid 20 can result in gas embolic complications. Some vascular access systems 2 include structures for extracting the fluid 20 from the vascular access assembly 6. In some embodiments, for example as shown, a fluid extraction assembly 8 pulls the fluid 20 into a fluid communication assembly 16 and then into the fluid extraction assembly 8. The fluid communication assembly 16 can include a passage that fluidly couples portions of the vascular access assembly 6 that contain the fluid 20 with the fluid extraction assembly 8. A low pressure area inside the fluid extraction assembly 8 can cause the fluid 20 to flow through the passage in the fluid communication assembly 16 and then into the fluid extraction assembly 8. The low pressure area can be caused by a syringe or any suitable vacuum assembly. FIG. 2 illustrates the fluid 20 after the fluid extraction assembly 8 has moved the fluid 20 into a portion of the fluid extraction assembly 8.

The access assembly 14 can pose a risk to medical professionals. For example, if the access assembly 14 includes a needle (or other sharp piercing member), medical professionals could inadvertently pierce their skin with the needle. This accidental piercing ("needle stick") could transfer blood from the patient to the medical professional. Blood transfer can transmit dangerous conditions such as human immunodeficiency virus ("HIV") and hepatitis. Some embodiments include structures for reducing the risk of a medical professional inadvertently piercing skin with the access assembly 14.

Referring now to FIGS. 1 and 2, several embodiments include an access extraction assembly 12 configured to move an access assembly 14 from a transcutaneous assembly 4 into the access extraction assembly 12. For example, some embodiments move a needle from a transcutaneous assembly 4 into the access extraction assembly 12, which can shield the needle from medical professionals and patients.

The transcutaneous assembly 4 can be removably coupled to the fluid communication assembly 16. The vascular access assembly 6 (or a portion thereof) can be removably coupled to the fluid extraction assembly 8. The vascular access assembly 6 (or a portion thereof) can be removably coupled to the access extractor assembly 12. In some embodiments, the fluid extraction assembly 8 is coupled and/or attached to the access extraction assembly 12, although in some embodiments, the fluid extraction assembly 8 is not coupled to the access extraction assembly 12. In some embodiments, for example as shown, the fluid extraction assembly 8 includes a syringe with a plunger configured to create a low pressure area to remove the fluid 20 from the vascular access assembly 6. In some embodiments, the access extraction assembly 12 includes a plunger coupled to the access assembly 14 such that moving the plunger proximally can cause the access assembly 14 to move proximally. The plunger of the fluid extraction assembly 8 can be mechanically coupled to the plunger of the access extraction assembly 12. FIG. 2 illustrates a proximal direction 18 and a distal direction 22 (as indicated by dashed arrows).

In some examples, once the fluid extraction assembly 8 and/or the access extraction assembly 12 has been decoupled from the vascular access assembly 6, a tubing assembly 24 (e.g., a catheter) can be coupled to the vascular access assembly 6 to enable a device located outside of the patient to be in fluid communication with a portion of the patient's circulatory system (e.g., a vein, an artery). In some embodiments, the tubing assembly 24 is placed in fluid communication with the fluid communication assembly 16, which is placed in fluid communication with the transcutaneous assembly 4, which is in fluid communication with a portion of the patient's circulatory system. In some embodiments, the tubing assembly 24 can be coupled to the vascular access assembly before the fluid extraction assembly 8 and/or the access extraction assembly 12 has been decoupled from the vascular access assembly.

Figure 3:
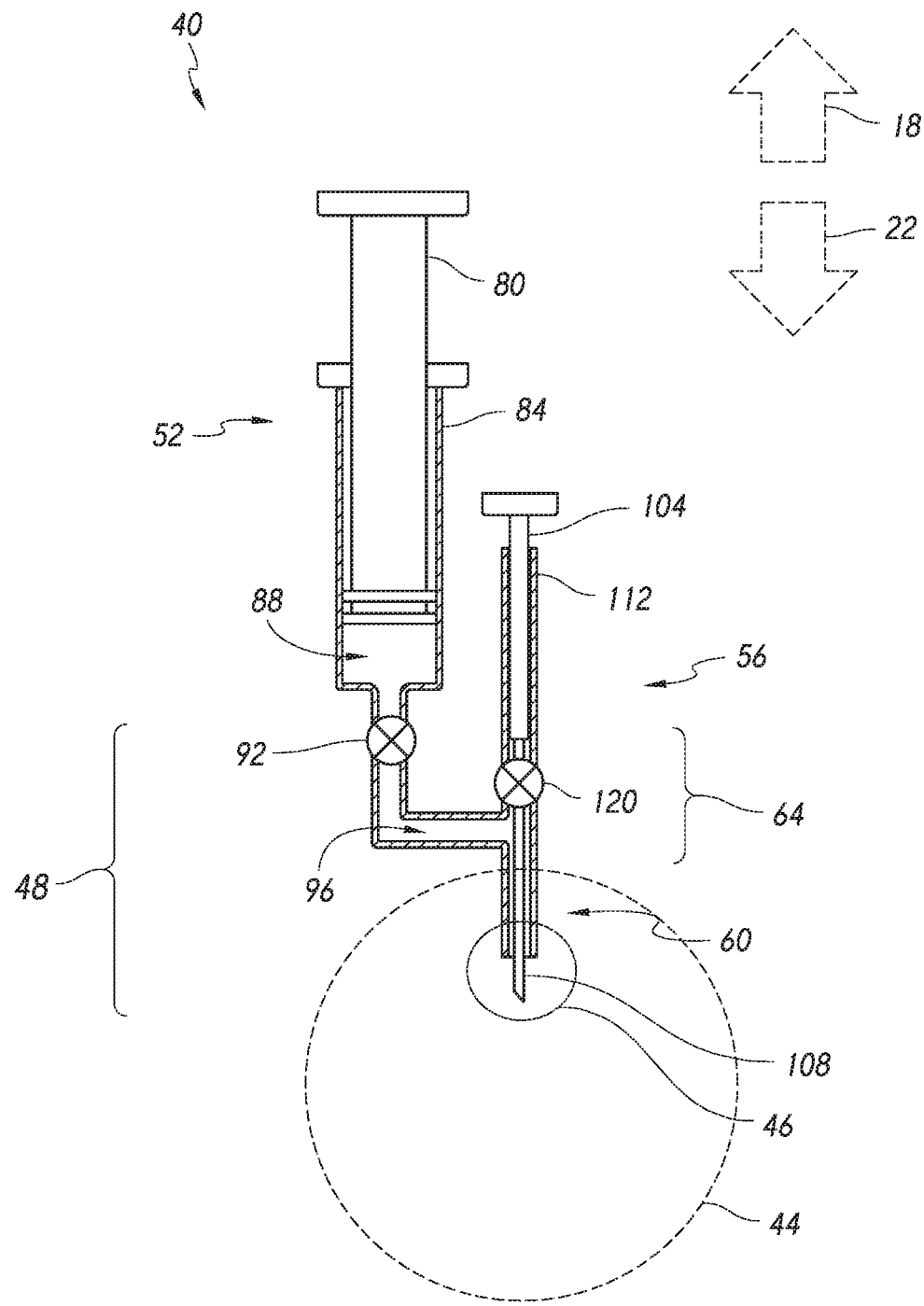
FIG. 3 schematically illustrates a vascular access system and a portion of a patient, according to some embodiments.

FIG. 3 schematically illustrates a vascular access system 40 and a portion of a patient 44 (e.g., a patient's arm). The system 40 can be the same or identical to any of the other systems described herein and can include any of the features of those other systems. A portion of the vascular access system 40 can pass through the skin of the patient 44 and into a blood channel 46 (e.g., a vein, an artery).

The vascular access system 40 can include a fluid extraction assembly 52. The fluid extraction assembly 52 can be removably or fixedly coupled to a vascular access assembly 48. In some embodiments, the vascular access system 40 includes an access extraction assembly 56 removably or fixedly coupled to the vascular access assembly 48. The vascular access assembly 48 can include a fluid communication assembly 64. In some embodiments, the fluid communication assembly 64 is configured to permit and/or restrict fluid communication between the vascular access assembly 48 and the fluid extraction assembly 52. In some embodiments, the fluid communication assembly 64 is configured to permit and/or restrict fluid communication between the vascular access assembly 48 and the access extraction assembly 56. The vascular access assembly 48 can include one or more components (e.g., needles, cannulas, catheters) configured to facilitate fluid communication between the vascular access system 40 and an internal fluid pathway (e.g., vein, artery, digestive tract, airway, etc.) of a patient.

The fluid extraction assembly 52 can include a plunger 80 located at least partially inside of a barrel 84. Plungers and barrels can be cylindrical, but do not necessarily have to be cylindrical. The plunger 80 can be configured to be slidably coupled to the barrel 84. The fluid extraction assembly 52 can include a syringe.

Sliding the plunger 80 proximally can increase the volume of a first reservoir 88 (e.g., a fluid reservoir), which can be located inside of the barrel 84. In some embodiments, the volume of the first reservoir 88 can be increased from an initial volume of zero or approximately zero. Increasing the volume of the first reservoir 88 can reduce the pressure inside of the first reservoir 88, creating a negative pressure to draw fluid into the first reservoir 88. Opening a first flow controller 92 can open a fluid passage between the first reservoir 88 and an internal portion 96 of the vascular access assembly 48. The internal portion 96 can be an inner channel and/or a passage, such as a passage located inside of the vascular access assembly 48.

In some embodiments, a flow controller allows fluid to flow through a passage when the flow controller is in an open position and prevents (or inhibits) fluid from flowing through the passage when the flow controller is in a closed position. Flow controllers can be formed by valves and/or seals that open and close passages. The flow controller can be and/or include a pump assembly, a valve assembly, a sealing assembly, a seal assembly, a plug assembly, and/or a system that pumps and/or selectively seals. In some embodiments, the flow controller is a valve that has an open position to allow fluid to pass through the valve and a closed position that blocks fluid from passing through the valve. In some embodiments, a flow controller is a cap or a plug configured to block fluid flow when the cap or plug is in a closed position.

Once the first reservoir 88 and the internal portion 96 are in fluid communication, fluid located inside of the internal portion 96 can flow into the first reservoir 88. Moving the plunger 80 proximally can cause the fluid to exit the vascular access assembly 48 and enter the fluid extraction assembly 52.

The vascular access system 40 can also include an access extraction assembly 56 configured to remove an access assembly from the patient 44 and/or from a fluid communication assembly 64. The access extraction assembly 56 can include a plunger 104 that can be mechanically coupled with a piercing member 108 (e.g., a needle, a cutting device, a sharp plastic spear, a tube configured to pierce skin). The plunger 104 can be slidably coupled to a barrel 112 such that at least a portion of the plunger 104 can slide within the barrel 112.

The access extraction assembly 56 can include a second flow controller 120 configured to inhibit or prevent fluid from inadvertently exiting the vascular access assembly 48. In some embodiments, the piercing member 108 passes through the second flow controller 120 such that the second flow controller 120 seals against a portion of the piercing member 108 and/or such that the second flow controller 120 closes (e.g., blocks fluid flow) once the piercing member 108 is not fully inside or not at least partially inside of the second flow controller 120. The second flow controller 120 can be a seal through which a piercing member 108 can pass. In several embodiments, the second flow controller 120 is in a closed position when the piercing member 108 is at least partially inside of the second flow controller 120 and when the piercing member 108 is located outside of the second flow controller 120. In some embodiments, the first flow controller 92 and the second flow controller 120 are formed by one flow controller. Several embodiments include more than two flow controllers.

In some embodiments, a first plunger (e.g., 80) and a second plunger (e.g., 104) are mechanically coupled such that the first plunger is configured to move proximally when the second plunger is moved proximally (and vice versa). In several embodiments, the first plunger and the second plunger are not mechanically coupled such that they can move independently of each other. In some embodiments, a first barrel (e.g., 84) and a second barrel (e.g., 112) are oriented parallel relative to each other (e.g., to move parallel to each other). In several embodiments, the first barrel and the second barrel are mechanically coupled such that they are oriented parallel relative to each other.

The fluid communication assembly 64 can include the first flow controller 92, the second flow controller 120, and/or the internal portion 96 (e.g., an internal channel, a passage). The fluid communication assembly 64 can be configured to enable removing fluid from inside of the vascular access assembly 48.

Figure 4:
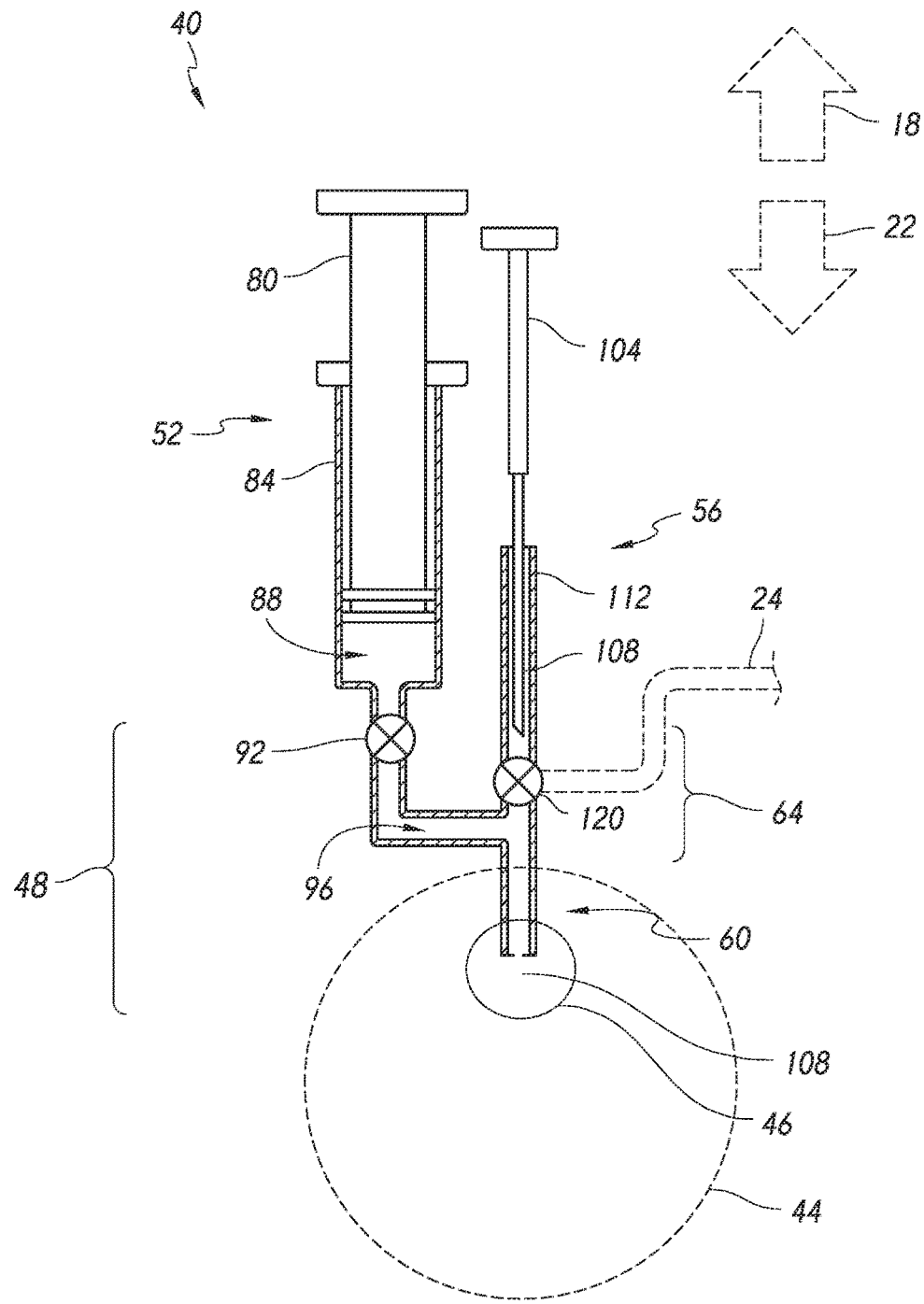
FIG. 4 schematically illustrates a plunger of the access extraction assembly located in a more proximal position than shown in FIG. 3, according to some embodiments.

FIG. 4 schematically illustrates the vascular access system 40 in which the plunger 104 of the access extraction assembly 56 is located in a more proximal position than shown in FIG. 3. The more proximal position of the plunger 104 results in the piercing member 108 being located outside of the transcutaneous assembly 60, outside of the fluid communication assembly 64, and outside of the second flow controller 120 (which can be a grommet and/or a seal constructed from a resilient or flexible material such as, for example, rubber or silicone). In some examples, upon detachment of the access extraction assembly 56 from the vascular access assembly 48, a tubing assembly 24 can be fluidly connected to the vascular access assembly 48 (e.g., to the first or second flow controllers 92 120).

Figure 5:
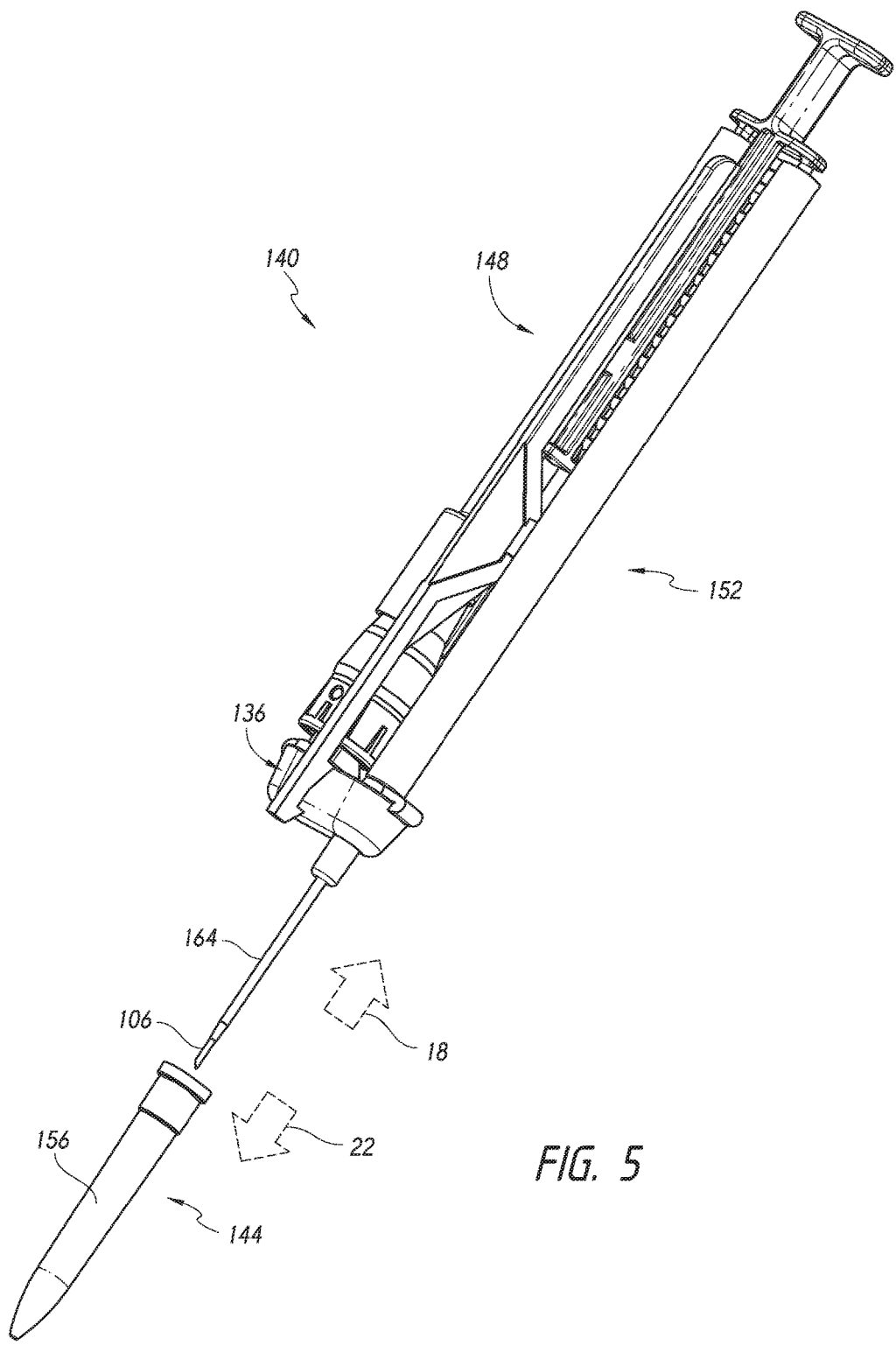
FIG. 5 illustrates a perspective view of a vascular access system, according to some embodiments.

FIG. 5 illustrates a perspective view of a vascular access system 140. The system 140 can be the same or identical to any of the other systems described herein and can include any of the features of those other systems. The vascular access system 140 can include a vascular access assembly 144. A fluid extraction assembly 148 can be removably coupled to the vascular access assembly 144. In some embodiments, an access extraction assembly 152 is coupled (e.g., removably or fixedly) to the fluid extraction assembly 148 and/or to the vascular access assembly 144. A cap 156 can cover a distal portion of a piercing member. The cap 156 can be a protective cover configured to shield medical professionals from the piercing member. The fluid extraction assembly 148 can be a syringe and/or can include a syringe.

A piercing member 160 (e.g., a needle) can be advanced from a catheter 164 such that the piercing member 160 protrudes distally from the distal end of the catheter 164. In FIG. 5, the piercing member 160 is located at the distal end of the vascular access system 140 and a plunger handle 172 is located at a proximal end of the vascular access system 140. The plunger handle 172 can be mechanically coupled to multiple plungers such that moving the plunger handle 172 distally and/or proximally causes multiple plungers to move distally and/or proximally.

Not all items are labeled in each figure in the interest of increasing the clarity of particular items in each figure. Many of the figures focus on different embodiments, although many embodiments can be combined to form assembly-level embodiments and/or system-level embodiments.

Figure 6:
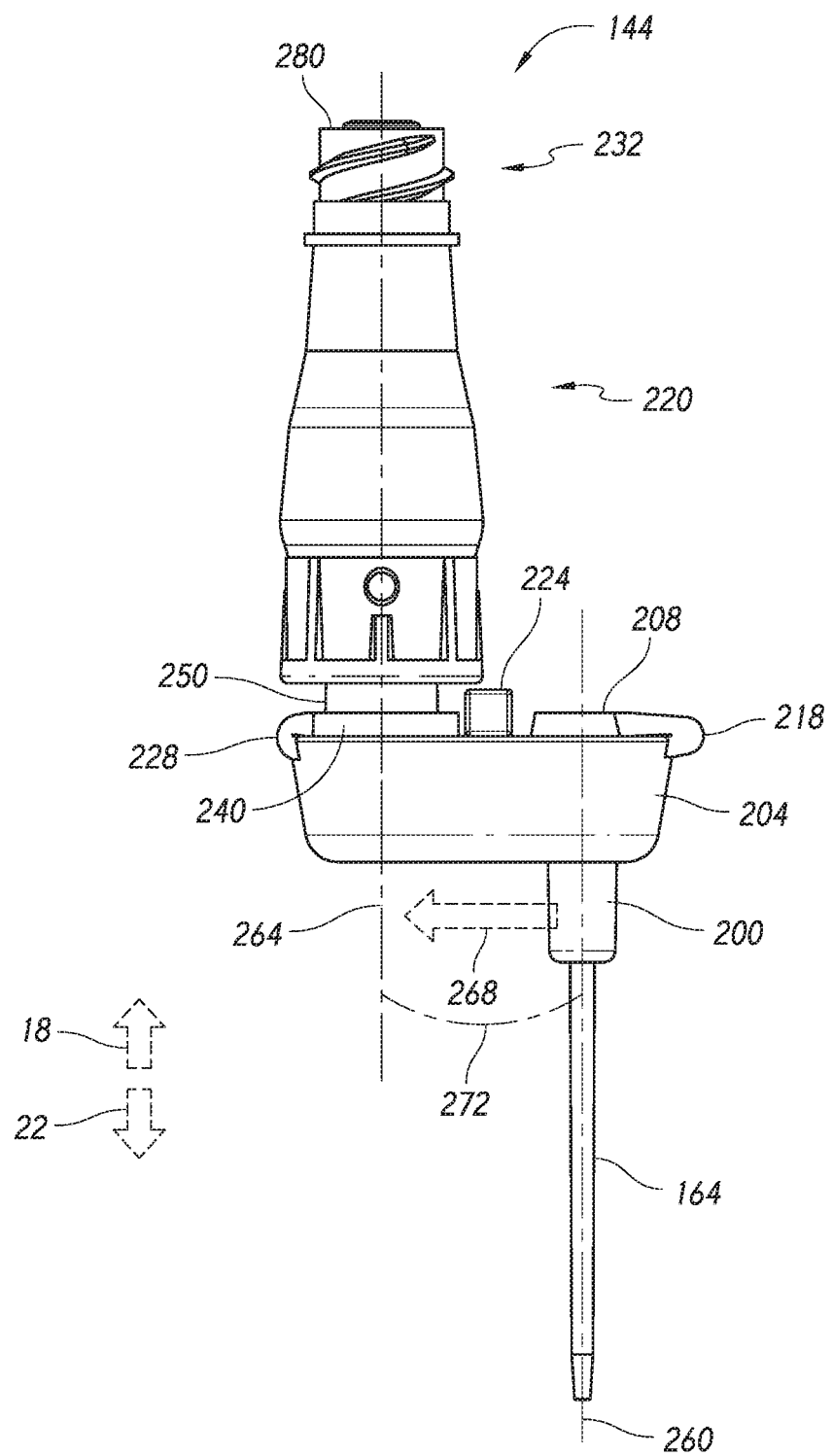
FIG. 6 illustrates a side view of the vascular access assembly, according to some embodiments.

FIG. 6 illustrates a side view of the vascular access assembly 144. The vascular access assembly 144 can include a connector 220. The connector 220 can be a fluid connector and/or a mechanical connector. The connector 220 can be configured to place the vascular access assembly 144 in fluid communication with the fluid extraction assembly 148 (shown in FIG. 11). The connector 220 can mechanically couple the vascular access assembly 144 to the fluid extraction assembly 148. The connector 220 can mechanically and fluidly couple to the rest of the vascular access assembly 144. The connector 220 can include threads 232 configured to threadably couple with another portion of the vascular access system 140 or other complementary medical device (e.g., a syringe). In some embodiments, the connector 220 is friction-fit with a portion of the vascular access system 140. In some embodiments, the connector 220 can be a needleless medical connector. In some embodiments, the connector 220 can be configured to accommodate any standard medical connector, such as ANSI (American National Standards Institute, Washington, D.C.) or other applicable standards. Some embodiments use a connector that is a MicroClave® neutral displacement connector commercially available from ICU Medical, Inc. Some embodiments use a connector that is a Clave® needle-free connector commercially available from ICU Medical, Inc. Several embodiments use different types of connectors, including those that do not conform to recognized standards and/or don't include internal conduits that engage a third seal 720 of the vascular access system 140 (described below).

An outer housing 204 can encase at least a portion of the vascular access assembly 144. A catheter support protrusion 200 can extend distally from the vascular access assembly 144 and/or from the outer housing 204 to support and/or increase the rigidity of the catheter 164. The catheter 164 can be configured to transmit a patient's blood and/or to transmit fluid from an external device into a patient. The catheter 164 can include one or more lumens.

A plug 208 can be coupled to the vascular access assembly 144 and/or to the outer housing 204. For example, the plug 308 can connect to a portion of the assembly 144 via a first hinge 218. The first hinge 218 can be a living hinge. The plug 208 can be a seal (e.g., a silicone seal, a grommet) through which a piercing member 160 (e.g., a needle) can pass. In several embodiments, the piercing member 160 can pass from a portion of an access extraction assembly (e.g., a barrel of the access extraction assembly 152 shown in FIG. 5) and through the catheter 164. The plug 208 can be a seal, such as a soft, silicone seal configured to inhibit or prevent fluid (e.g., blood) from leaking out of the vascular access assembly 144 (e.g., by leaking around the perimeter of a piercing member). In some embodiments, the plug 208 includes a seal made from a material (e.g., a rubber) with a durometer that is between about 10 Shore A and about 90 Shore A. Several seal and/or plug embodiments include seals molded from medical-grade silicone with a durometer between about 35 Shore A and about 80 Shore A. Other seals, grommets, and plugs are molded from other flexible or semi-flexible materials.

In several embodiments, the plug 208 is molded from a first material and a seal is molded from a second material, which has a durometer that is at least 15 Shore A less than the durometer of the first material. The seal can be located inside of the plug 208 such that the plug 208 at least partially surrounds the seal and a piercing member 160 (shown in FIG. 5) passes through the seal (e.g., a first seal 236 shown in FIG. 13, but hidden in many figures).

The outer housing 204 can also include a second hinge 228, which can be a living hinge. The second hinge 228 can couple a hoop 240 to the outer housing 204. The hoop 240, which can be circular, can wrap around a proximal protrusion 250 configured to couple with the connector 220. In some embodiments, the hoop 240 is not connected to a hinge. For example, the hoop 240 can be positioned around one or more portions of the outer housing 204 via a friction fit.

As illustrated in FIG. 6, a hoop 240 can surround at least a portion of the proximal protrusion 250. The hoop 240 can help couple the outer housing 204 to an inner housing 350 (shown in FIG. 7). The outer housing 204 can at least partially surround and/or encase the inner housing 350.

The catheter 164 can include a first central axis 260 and the connector 220 can include a second central axis 264. The first central axis 260 can be parallel to the second central axis 264. In several embodiments, the lateral distance 268 between the first central axis and the second central axis can be at least about 4 millimeters and/or less than or equal to about 75 millimeters; at least about 8 millimeters and/or less than or equal to about 50 millimeters; or at least about 10 millimeters and/or less than or equal to about 20 millimeters.

In several embodiments, for example as illustrated, the first central axis 260 and the second central axis 264 can be oriented at an angle 272 relative to each other. The angle 272 is in the plane that includes both the first central axis 260 and the second central axis 264. The angle 272 is the smallest angle in the plane between the first central axis 260 and the second central axis 264. In some embodiments, the angle 272 between the first central axis 260 and the second central axis 264 is greater than or equal to about zero degrees and/or less than or equal to about 90 degrees; greater than or equal to about zero degrees and/or less than or equal to about 25 degrees; or greater than or equal to about 5 degrees and/or less than or equal to about 15 degrees.

In several embodiments, vascular access assemblies have fluid (e.g., gas) located inside an internal portion of the vascular access assemblies. This fluid, which can be a gas such as air, can cause air embolic complications if allowed to enter a patient's vascular system. For example, the vascular access assembly 144 can include fluid located inside of the vascular access assembly 144 (e.g., inside of the outer housing 204 and/or inside of a second passage 296). In some embodiments, methods of use include removing this fluid prior to transmitting fluids (e.g., through a first passage 300 in the catheter 164) into the patient.

To remove the fluid (e.g., a gas) from the vascular access assembly 144, blood from a blood channel 46 can flow into the first passage 300 of the catheter, into a second passage 296, and then into a third passage 304 located inside of the connector 220. The blood can then flow into a syringe (not shown). This blood flow can remove fluid (e.g., the fluid in the vascular access assembly 144) from the vascular access assembly 144 to "prime" the vascular access assembly 144.

Figure 7:
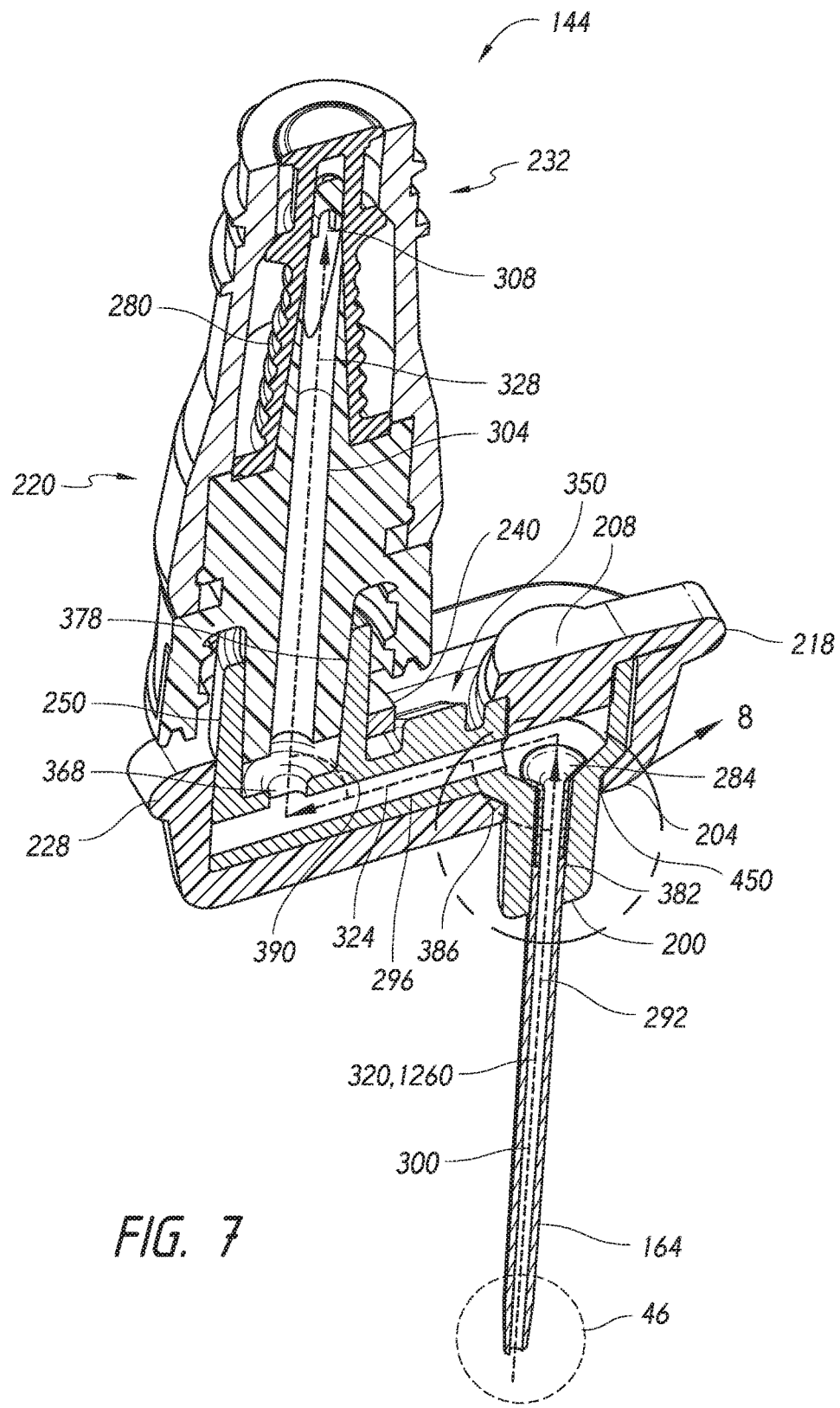
FIG. 7 illustrates a perspective view cross section view of the vascular access assembly of FIG. 6, according to some embodiments.

As illustrated in FIG. 7, a second seal 280 (e.g., a flow controller) can block, close, and/or seal an exit 308 (e.g., an aperture) from the third passage 304 such that fluid is inhibited or prevented from moving past the second seal 280 from the third passage 304. Moving the second seal 280 distally can unblock and/or unseal the exit 308 such that fluid can move from the third passage 304 past the second seal 280. Dashed lines 320, 324, 328 illustrate one way in which fluid and/or blood can travel through the first passage 300, the second passage 296, and the third passage 304. Mechanically coupling the connector 220 to the fluid extraction assembly 148 (shown in FIG. 22) can cause the second seal 280 to move distally to open the exit 308. The third passage 304 can be a channel configured to open (to allow fluid flow) and close (to block and/or inhibit fluid flow).

The plug 208 can block, seal, and/or close a fluid path 292 from the first passage 300 of the catheter 164. Unblocking, unsealing, and/or opening the plug 208 can enable a medical professional to establish fluid communication between an outside device (e.g., a tube located outside of the patient, tubing assembly 24 in FIG. 4) and the catheter 164 such that the outside device is in fluid communication with the blood channel 46.

The outer housing 204 can be part of the fluid communication assembly discussed previously. The fluid communication assembly can include at least a portion of the first passage 300, the second passage 296, and/or the third passage 304. The connector 220 can include a portion of the fluid communication assembly.

The catheter support protrusion 200 can include a cylinder that is oriented parallel to the catheter 164 and/or the piercing member 160 (shown in FIG. 6). The catheter support protrusion 200 can include a hollow portion and/or a channel in which a portion of the catheter 200 and/or a portion of the piercing member 160 can be located.

Although some embodiments use the connector 220 illustrated in FIG. 7, other embodiments include other types of mechanical connectors, fluid connectors, and flow controllers. In some embodiments, as illustrated, a connector 220 can include one or more circumferential projections or flanges, such as the circumferential projection 238, that can extend completely or partially around the connector. In some embodiments, the projection can be used to help attach the connector to a fluid extraction assembly 148, as described in more detail below.

Figure 9:
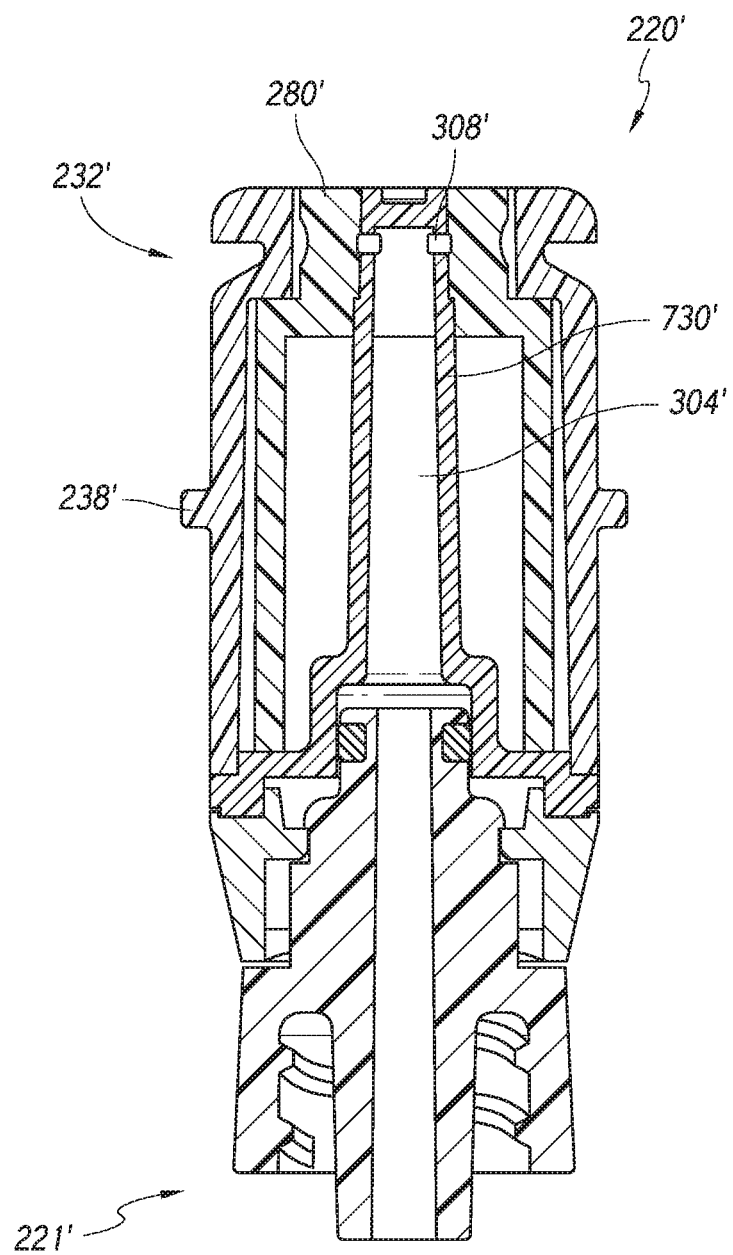
FIG. 9 illustrates a cross-sectional view of a connector, according to some embodiments.

In some embodiments, as described above, medical connectors for use in a vascular access system may not conform to recognized standards. For example, FIG. 9 illustrates a cross-sectional view of one embodiment of a medical connector 220' that is not configured to conform to applicable connection standards. Such a connector is disclosed in greater detail in U.S. patent application Ser. No. 14/199,836, entitled "MEDICAL CONNECTORS WITH FLUID-RESISTANT MATING INTERFACES, filed on Mar. 6, 2014, now published as US-2014-0246616 A1, the entire disclosure of which is hereby incorporated by reference and made part of the present specification. This can be helpful where it is desirable that the particular connector be used, since a different connector cannot be accidentally used with the system. In some embodiments, the base 221' of the medical connector may not conform to connection standards but the threads 232' or other upper connection mechanism may. In some embodiments, the threads or upper connection mechanism may not conform to connection standards while the base does. In some embodiments, neither the upper connection mechanism nor the base conform to applicable connection standards.

In some embodiments, a medical connector may have a shoulder instead of a projection. For example, FIGS. 10 and 11 illustrates one embodiment of a medical connector 220" that includes a shoulder 230" instead of a circumferential projection to help attach the connector to a fluid extraction assembly. Examples of medical connectors having the same or similar features as medical connector 220" are further explained in International Patent Application Serial No. PCT/US2013/069312, entitled "MEDICAL CONNECTOR," filed on Nov. 8, 2013, now published as WO 2014/074929, the entire content of which is hereby incorporated by reference and made part of the present specification.

Figure 12:
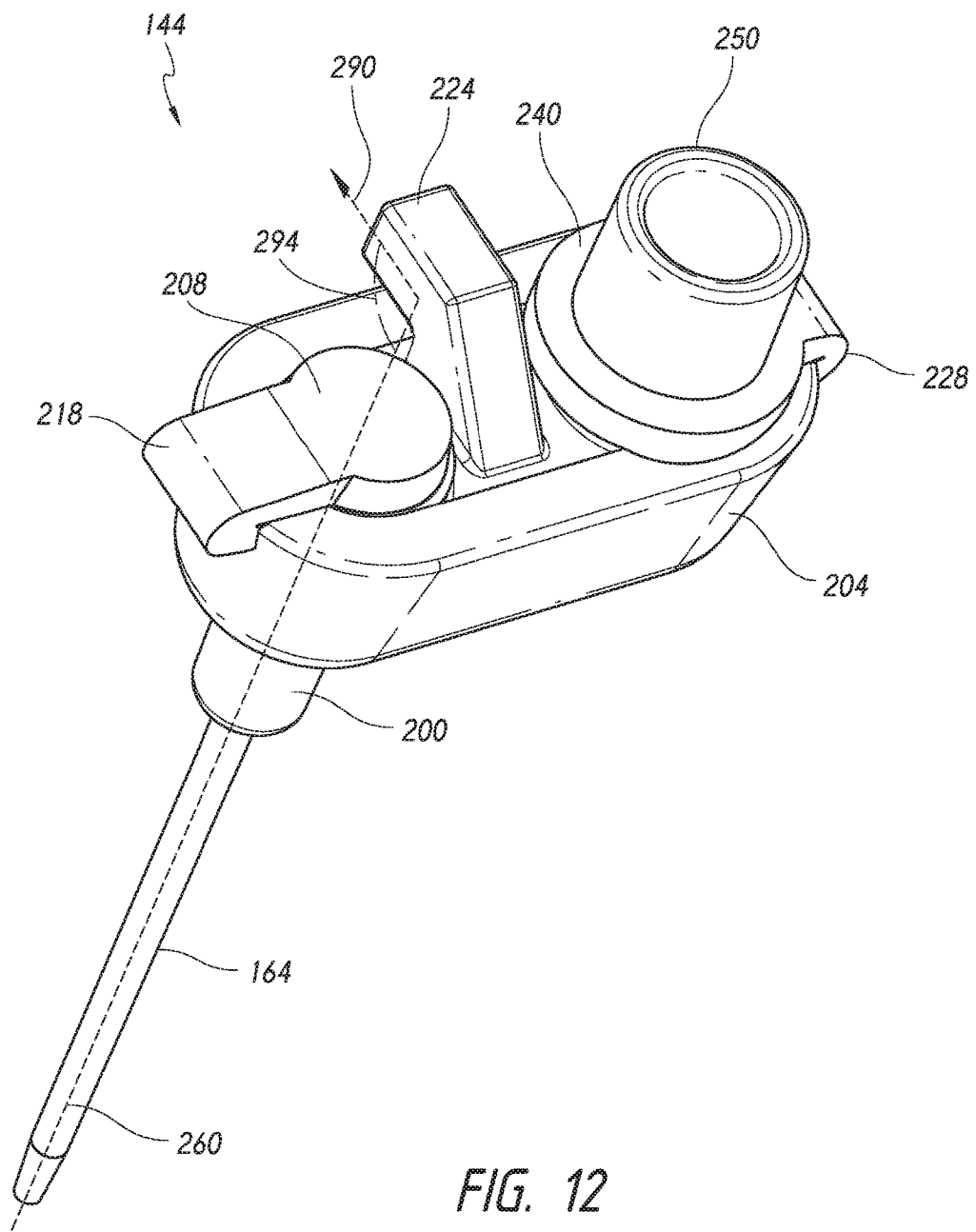
FIG. 12 illustrates a perspective view of a fluid communication assembly without the connector, according to some embodiments.

FIG. 12 illustrates a perspective view of a fluid communication assembly without the connector 220. In some embodiments, the fluid communication assembly can include a locking tooth 224. A protrusion direction 290 of the locking tooth 224 can be oriented at an angle 294 relative to the first central axis 260 of the catheter 164. The angle 294 can be approximately 90 degrees. In several embodiments, the angle 294 is greater than or equal to about 45 degrees and/or less than or equal to about 135 degrees; greater than or equal to about 60 degrees and/or less than or equal to about 120 degrees; or greater than or equal to about 80 degrees and/or less than or equal to about 100 degrees. In some embodiments, the angle 294 is greater than 75 degrees and less than 105 degrees.

In some embodiments, the plug 208 can be unblocked, unsealed, or opened to expose the fluid path 292. As a result, the fluid path 292 can transmit fluid through the catheter support protrusion 200 (e.g., through a catheter) and into and/or out of an external device (e.g., a tube, a cannula, an IV bag) (not shown). In some embodiments, fluid can also or alternatively flow through an internal channel 382 in the catheter support protrusion 200, through the second passage 296, through a fourth passage 368, and into an internal channel 382 in the proximal protrusion 250. Fluid can also flow in the opposite direction.

In some embodiments, as illustrated in FIG. 7, the inner channel 382 of the catheter support protrusion 200 can be oriented at an angle 386 relative to the second passage 296. In several embodiments, the angle 386 is greater than or equal to about 45 degrees and/or less than or equal to about 135 degrees; greater than or equal to about 60 degrees and/or less than or equal to about 120 degrees; or greater than or equal to about 80 degrees and/or less than or equal to about 100 degrees. In some embodiments, the angle 294 is greater than about 75 degrees and less than about 105 degrees.

The inner channel 378 of the proximal protrusion 250 can be oriented at an angle 390 relative to the second passage 296. In several embodiments, the angle 390 is greater than or equal to 45 degrees and/or less than or equal to about 135 degrees; greater than or equal to about 60 degrees and/or less than or equal to about 120 degrees; or greater than or equal to about 80 degrees and/or less than or equal to about 100 degrees. In some embodiments, the angle 294 is greater than about 75 degrees and less than about 105 degrees.

Figure 8:
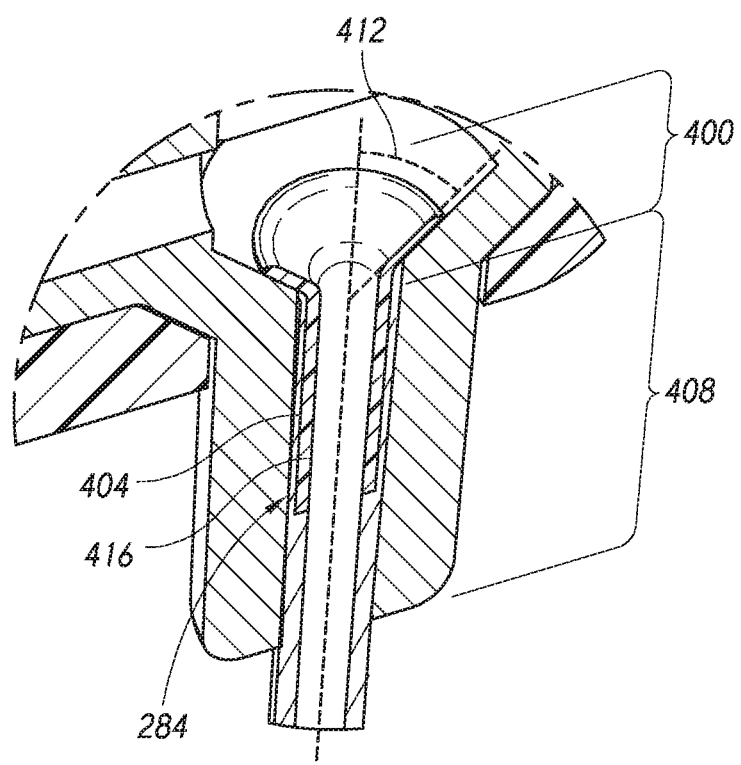
FIG. 8 illustrates a zoomed-in perspective view of the cross section illustrated in FIG. 7.

In some embodiments, as illustrated in FIGS. 7 and 8, a guide 284 can inhibit or prevent the piercing member 160 (shown in FIG. 5) from going through a wall of the inner housing 350. The guide 284 can be machined and/or formed from metal, such as medical-grade stainless steel. An inner channel 416 in the guide 248 can help direct the piercing member 160 as it passes through the guide 284.

The guide 284 can include a funnel portion 400 and a substantially cylindrical portion 404. In some embodiments, the funnel portion 400 can be located outside of a proximal end of the catheter and the substantially cylindrical portion 404 and/or a distal portion 408 can be located inside of an inner channel (e.g., a lumen) of the catheter 164. The funnel portion 400 can include a funnel angle 412. In several embodiments, the angle 412 is greater than or equal to about 15 degrees and/or less than or equal to about 75 degrees; greater than or equal to about 25 degrees and/or less than or equal to about 65 degrees; or greater than or equal to about 35 degrees and/or less than or equal to about 55 degrees. In some embodiments, the angle 294 is greater than about 30 degrees and less than about 60 degrees. In several embodiments, the angle 294 is approximately 45 degrees.

Although many different shapes of outer housings 204 are used in various embodiments, some embodiments include at least one plug 208 and a ring, such as a hoop 240. An exit hole 450 can enable at least a portion of a piercing member 160, a catheter 164, a guide 284, and/or an inner housing 350 (not shown) to pass through at least a portion of the outer housing 204. In some embodiments, the outer housing 204 is integrated with at least one other component described herein. In some embodiments, the outer housing 204 is not necessarily a separate component.

FIG. 13 illustrates a side view of a catheter 164. The catheter 164 can include a distal portion 454 and a proximal portion 458. FIG. 14 illustrates a side view of the distal portion 454 of the catheter 164. Referring now to FIGS. 13 and 14, the distal portion 454 of the catheter can include a tapered end 462 having a distal-most edge 455. The tapered end 462 can help widen an opening made by a piercing member in a patient's tissue as the catheter is inserted into the opening. The catheter can have an inner diameter $ID_4$ at the distal most edge 455 of the tapered end 462. In some embodiments, the inner diameter $ID_4$ can remain generally constant along the length of the catheter. In some embodiments, the inner diameter of the catheter can vary.

The proximal portion 458 of the catheter 164 can be located inside of the guide 284, the outer housing 204, and/or the inner housing 350 (shown in FIGS. 7 and 11). Referring now to FIG. 7, the plug 208 and/or the second passage 296 can be located proximally relative to the proximal portion 458.

Figure 15:
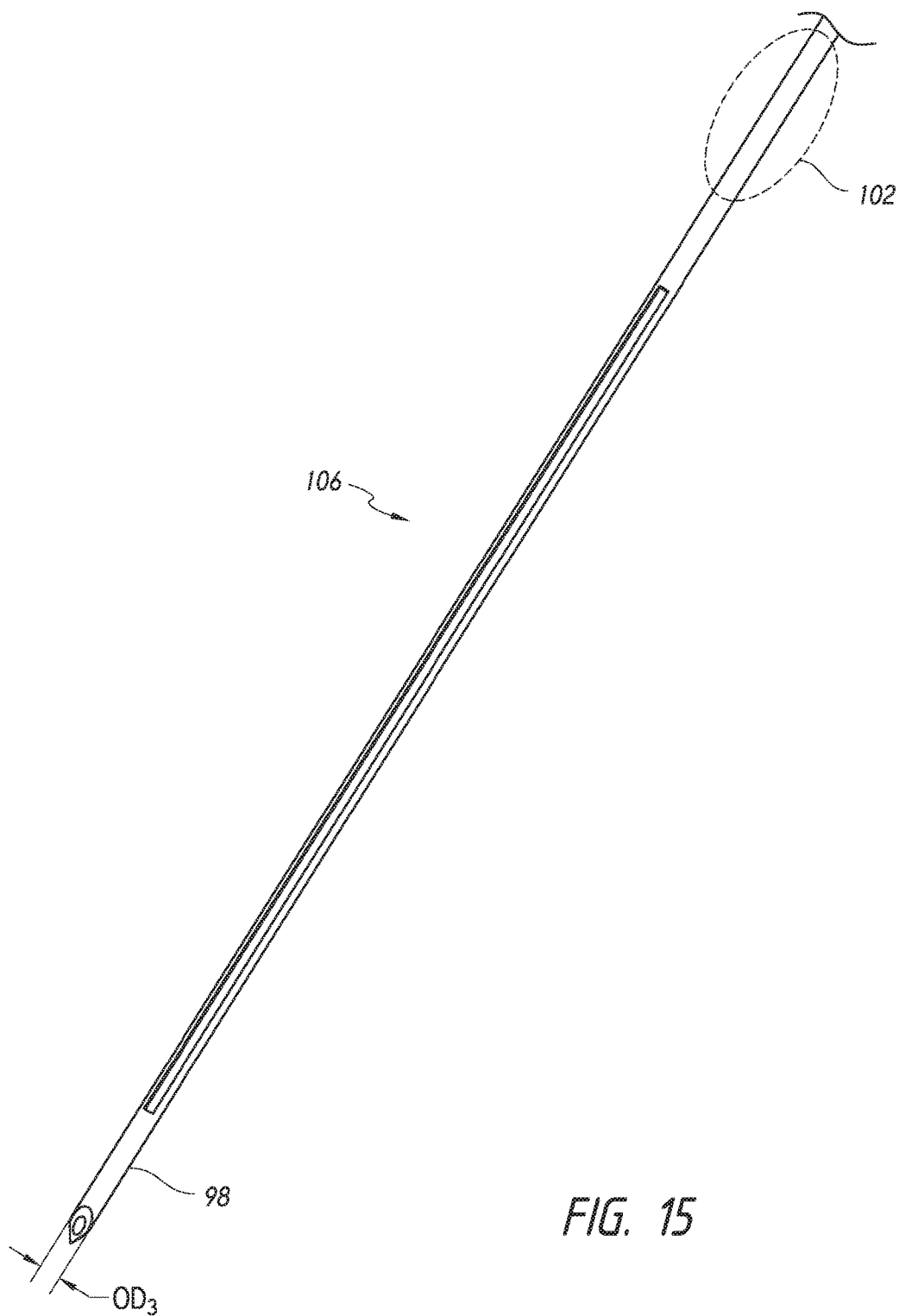
FIG. 15 illustrates a perspective view of a needle, according to some embodiments.
Figure 16:
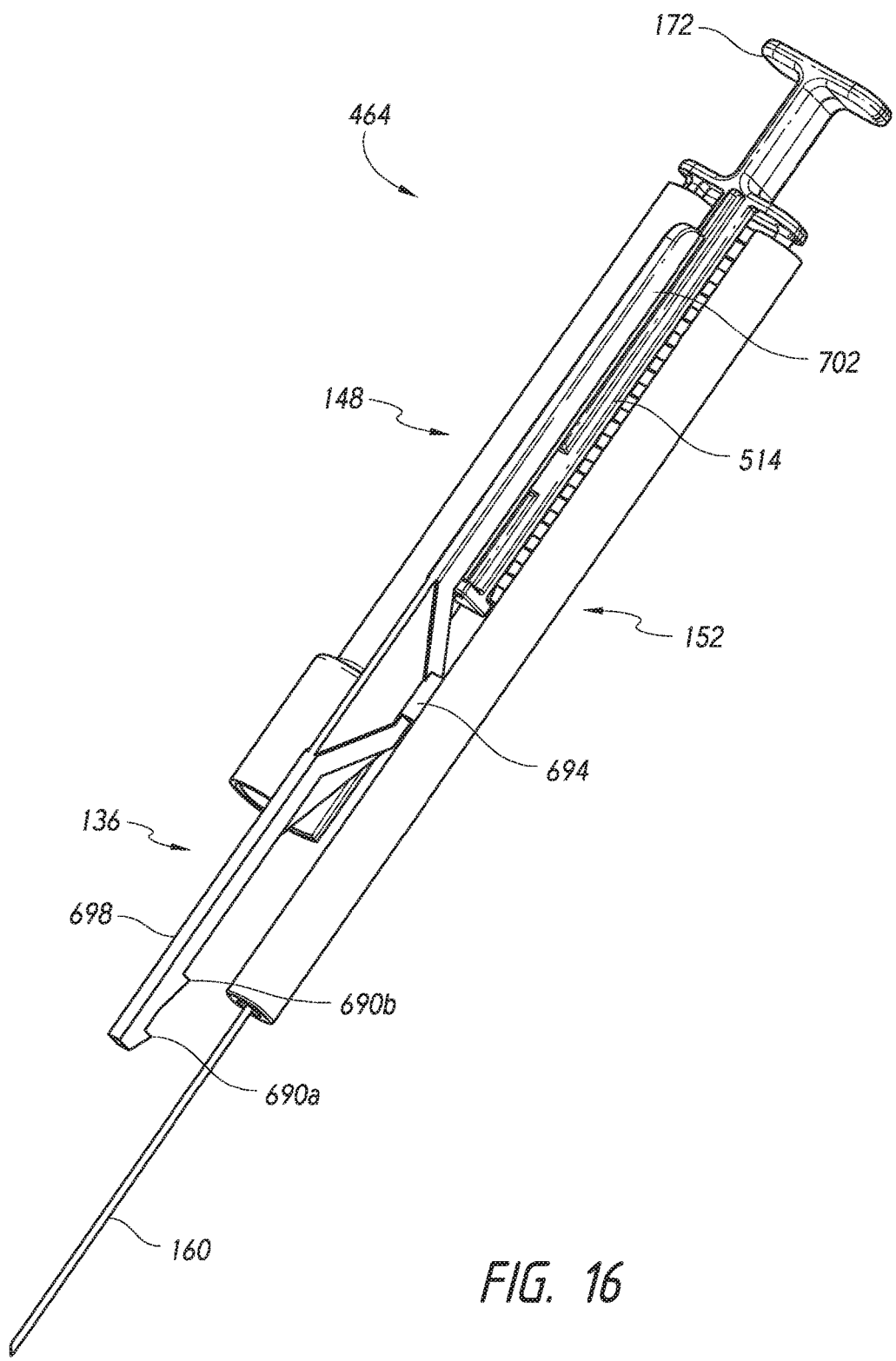
FIG. 16 illustrates a perspective view of a fluid extraction assembly and an access extraction assembly, according to some embodiments.

FIG. 15 illustrates a perspective view of a needle 106, which can be a type of piercing member (e.g., 160 in FIG. 16). The needle 106 can include a proximal portion 102 coupled to the slot 670 of the shaft 484 illustrated in FIG. 37. The needle 106 can include a distal tip 98 and a lumen. The needle can have an outer diameter $OD_3$ at the distal tip 98. In some embodiments, the outer diameter can be constant along the length of the needle. In some embodiments, the outer diameter $OD_3$ can be greater than the inner diameter $ID_4$ of the catheter. In such embodiments, the needle can expand the catheter in order to pass through. This can help create a seal between the catheter and the needle 106 such that when the needle and catheter are within a patient's blood vessel, blood will be prevented or substantially prevented from flowing between the needle and the catheter. In various embodiments, these dimensional relationships can exist for other types of catheters and for other types of piercing members 160.

FIG. 16 illustrates a perspective view of the fluid extraction assembly 148 and the access extraction assembly 152. FIG. 16 generally shows the front of the extraction assembly 464. The extraction assembly 464 can include the fluid extraction assembly 148, the access extraction assembly 152, and a plunger handle 172.

In several embodiments, the fluid extraction assembly 148 and the access extraction assembly 152 are mechanically coupled together. A single plunger handle 172 can be configured to operate the fluid extraction assembly 148 and the access extraction assembly 152. In several embodiments, the plunger handle 172 simultaneously and/or concurrently operates the fluid extraction assembly 148 and the access extraction assembly 152.

The access extraction assembly 152 can include a piercing member 160. Moving the plunger handle 172 proximally can retract the piercing member 160 and can cause the fluid extraction assembly 148 to remove fluid (e.g., air, bodily fluid) from a vascular access assembly 144 (shown in FIG. 12).

Figure 17:
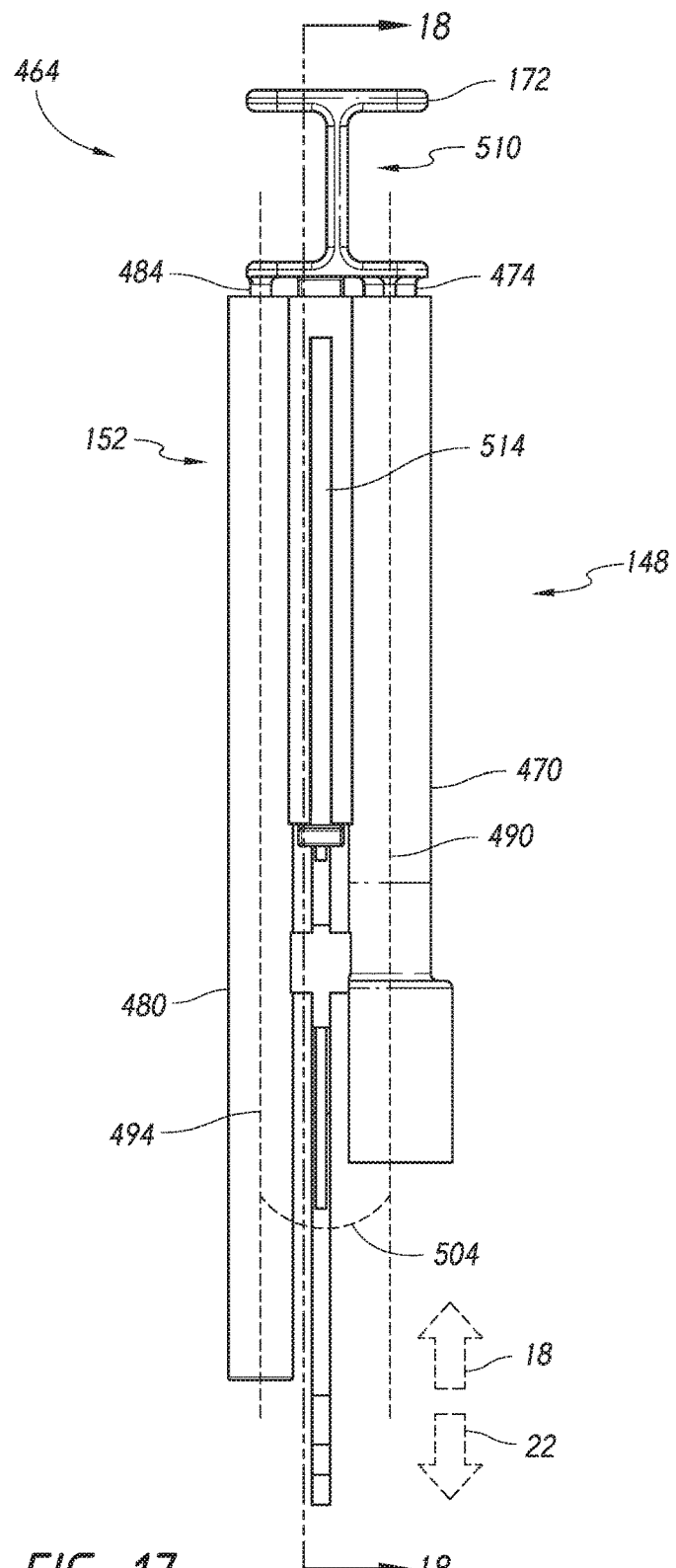
FIG. 17 illustrates a back view of the extraction assembly, according to some embodiments.

FIG. 17 illustrates a back view of the extraction assembly 464. The fluid extraction assembly 148 can include a first barrel 470 and a first plunger 474 (which can be a shaft or rod). The first barrel 470 and the first plunger 474 can be part of a syringe configured to remove fluid and/or prime a vascular access assembly. The first plunger 474 can be slidably coupled to the first barrel 470 such that the first plunger 474 can be configured to slide within at least a portion of the first barrel 470.

The first barrel 470 and the first plunger 474 can include cylindrical portions. In some embodiments, more than 50% of the external surface of the barrel 470 is cylindrical. In several embodiments, the first barrel 470 and/or the first plunger 474 do not include cylindrical portions.

The access extraction assembly 152 can include a second barrel 480 and a shaft 484. The shaft 484 can be a second plunger. In some embodiments, the shaft 484 is a protrusion that is greater than or equal to about 50 millimeters ("mm") long (measured in the proximal-distal direction) and less than or equal to about 10 mm wide (measured perpendicularly relative to the length). In several embodiments, the shaft is greater than or equal to about 20 mm long and/or less than or equal to about 250 mm long; greater than or equal to about 40 mm long and/or less than or equal to about 150 mm long; or greater than or equal to about 50 mm long and/or less than or equal to about 120 mm long. The shaft 484 can be slidably coupled to the second barrel 480 such that at least a portion of the shaft 484 is configured to slide inside of at least a portion of the second barrel 480.

The first barrel 470 can have a third central axis 490. The second barrel 480 can have a fourth central axis 494. In some embodiments, for example as illustrated, the first barrel 470 is parallel to the second barrel 480. In several embodiments, the first barrel 470 can be oriented at an angle 504 relative to the second barrel 480. The third central axis 490 and the fourth central axis 494 can be oriented at an angle 504 relative to each other. The angle 504 is in the plane that includes both the third central axis 490 and the fourth central axis 494. In some embodiments, the angle 504 between the third central axis 490 and the fourth central axis 494 is greater than or equal to about zero degrees and/or less than or equal to about 45 degrees; greater than or equal to about zero degrees and/or less than or equal to about 15 degrees; or greater than or equal to about 1 degree and/or less than or equal to about 5 degrees. In some embodiments, the angle 504 is equal to or greater than about zero degrees and/or less than about 4 degrees.

In some embodiments, the plunger assembly 510 can include a locking device 514 (e.g., which can be a shaft, a rod, or a slidable blocking bar). The locking device 514 can be configured to allow the plunger assembly 510 to slide in the proximal direction 180 while impeding sliding and/or preventing sliding in the distal direction 176. In some embodiments, the locking device 514 can be configured to prevent movement and/or to impede movement in the distal direction and/or proximal direction 180.

As used herein, "radially outward" means radially outward from a central axis of the reference item. For example, in FIG. 17, the first barrel 470 (e.g., part of a syringe) is located radially outward from the shaft 484, which is located inside of the second barrel 480.

Figure 18:
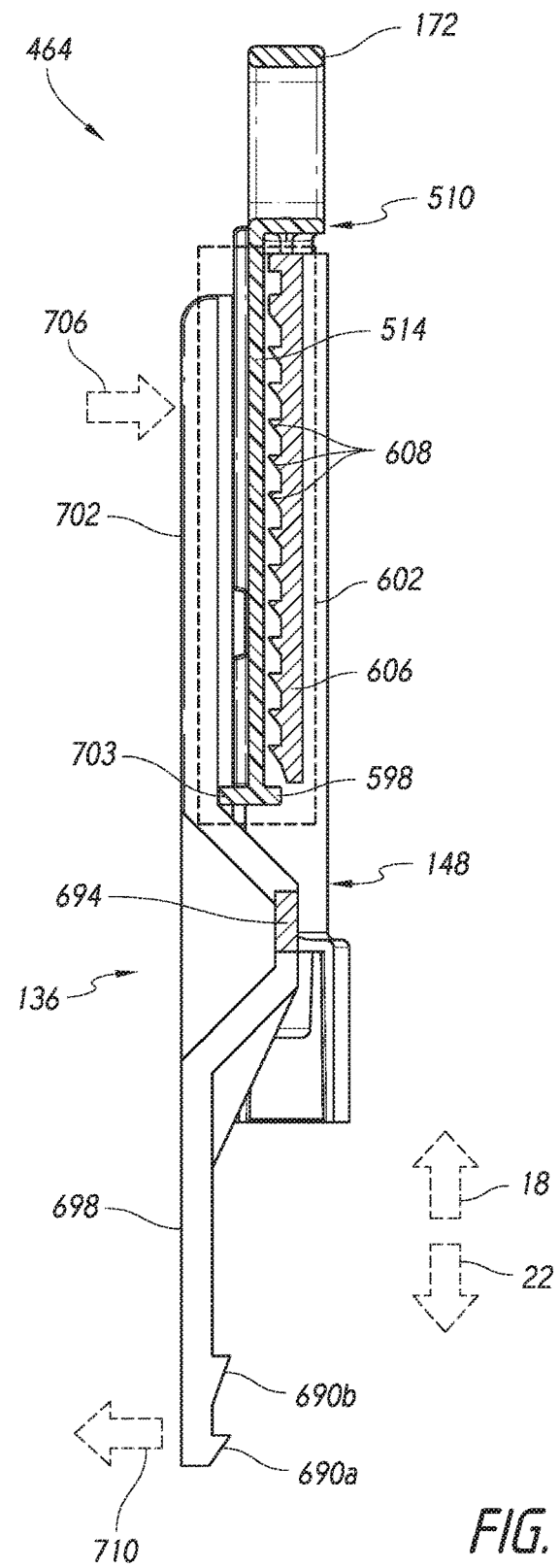
FIG. 18 illustrates a cross-sectional view along line 18-18 from FIG. 17, according to some embodiments.
Figure 19:
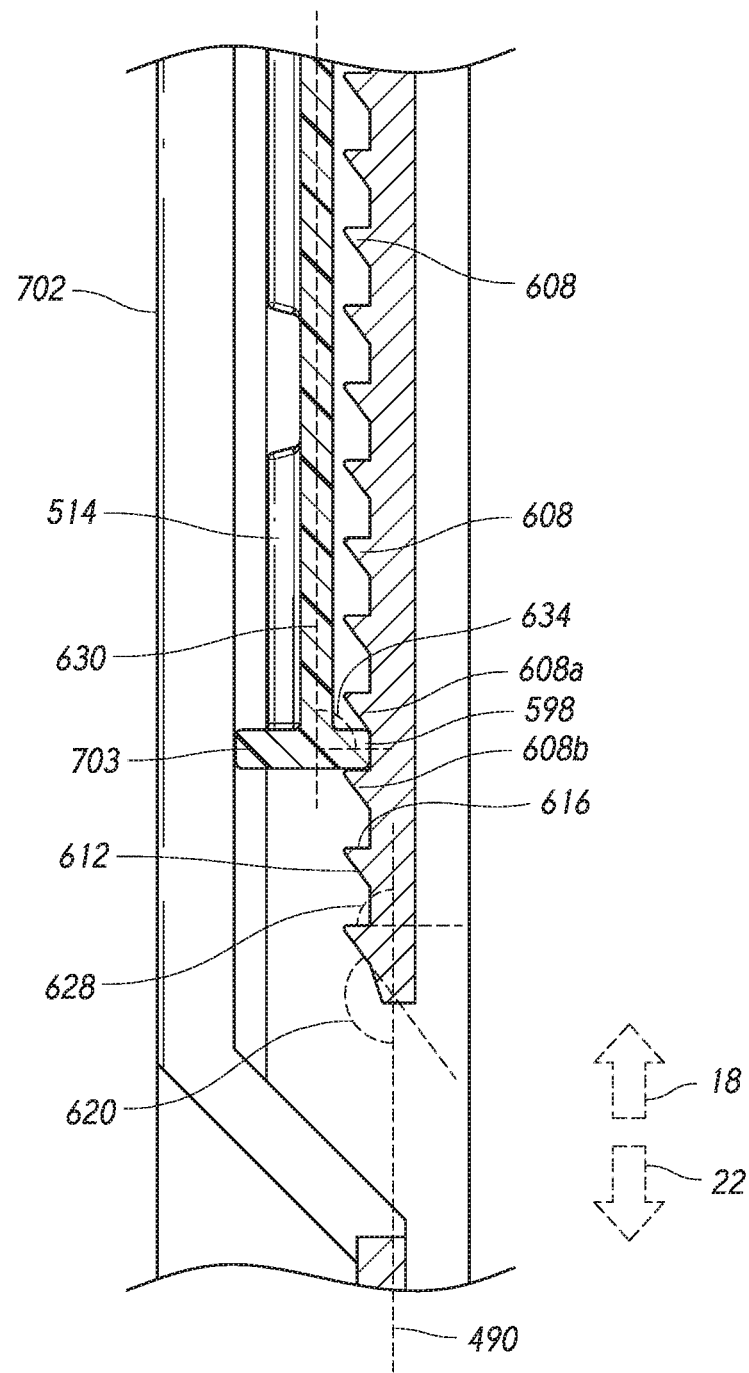
FIG. 19 illustrates a close-up view of the plunger tooth from FIG. 18, according to some embodiments.

FIG. 18 illustrates a cross-sectional view along line 18-18 from FIG. 17. The extraction assembly 464 can include teeth 608 configured to contact a plunger tooth 598 on a locking device 514 (not all of the teeth 608 are labeled). The teeth 608 can be fixed to a portion of the extraction assembly 464 such as the first barrel 470, the second barrel 480, the fluid extraction assembly 148, and/or the access extraction assembly 152 (shown in FIG. 17). The teeth 608 and the plunger tooth 598 can form a ratchet assembly configured to allow proximal movement and to prevent, impede, and/or hinder distal movement. This can help inhibit or prevent a piercing member from being accidentally exposed once it has been pulled into the access extraction assembly 152. In some embodiments, the ratchet assembly allows the plunger assembly 510 to slide proximally while at least a portion of the first plunger 474 is located inside the first barrel 470 and while at least a portion of the shaft 484 is located inside the second barrel 480 (shown in FIG. 17). In several embodiments, the ratchet assembly hinders, impedes, limits, and/or prevents the plunger assembly 510 from sliding more than a certain amount distally while at least a portion of the first plunger 474 is located inside the first barrel 470 and while at least a portion of the shaft 484 is located inside the second barrel 480 (shown in FIG. 17). In some embodiments, the certain amount is determined by the thickness of the plunger tooth 598 along the third central axis 490 (shown in FIG. 17) compared to the distance between the teeth 608. For example, in some embodiments, the plunger tooth 598 can slide distally and/or proximally between a first tooth 608a and an adjacent tooth 608b (as shown in FIG. 19).

Some embodiments include a ratchet assembly 602 In FIG. 18, the ratchet assembly 602 is shown in a dashed box. The ratchet assembly 602 can be a one-way ratchet assembly. The ratchet assembly 602 can include a linear rack 606 and a pawl (e.g., the plunger tooth 598). The linear rack 606 can include multiple teeth 608. The plunger tooth 598 can be a protrusion that extends towards the teeth 608 of the linear rack 606.

FIG. 18 illustrates the plunger tooth 598 located distally relative to the teeth 608. FIG. 19 illustrates a close-up view of the plunger tooth 598 from FIG. 18, positioned in a more proximal position. Each tooth 608 can include a distal face 612 and a proximal face 616. The distal face 612 can be oriented at an angle 620 relative to the third central axis 490 as shown in FIG. 19. In some embodiments, the angle 620 is configured to enable the plunger tooth 598 to slide proximally past the teeth 608. At least a portion of the locking device 514 can deform away from the teeth 608 to enable the plunger tooth 598 to clear each tooth 608. In some embodiments, the angle 620 is greater than or equal to about 100 degrees and/or less than or equal to about 175 degrees; greater than or equal to about 110 degrees and/or less than or equal to about 160 degrees; greater than or equal to about 120 degrees and/or less than or equal to about 160 degrees; or approximately 135 degrees. In several embodiments, the angle 620 is greater than about 115 degrees and/or less than about 155 degrees.

The locking device 514 can have a fifth central axis 630. The plunger tooth 598 can protrude away from the fifth central axis 630 at an angle 634. In several embodiments, the angle 634 is approximately 90 degrees. In some embodiments, the angle 634 is greater than or equal to about 45 degrees and/or less than or equal to about 135 degrees; greater than or equal to about 65 degrees and/or less than or equal to about 115 degrees; or greater than or equal to about 80 degrees and/or less than or equal to about 100 degrees. In some embodiments, the angle 634 is less than about 105 degrees and more than about 75 degrees.

Figure 20:
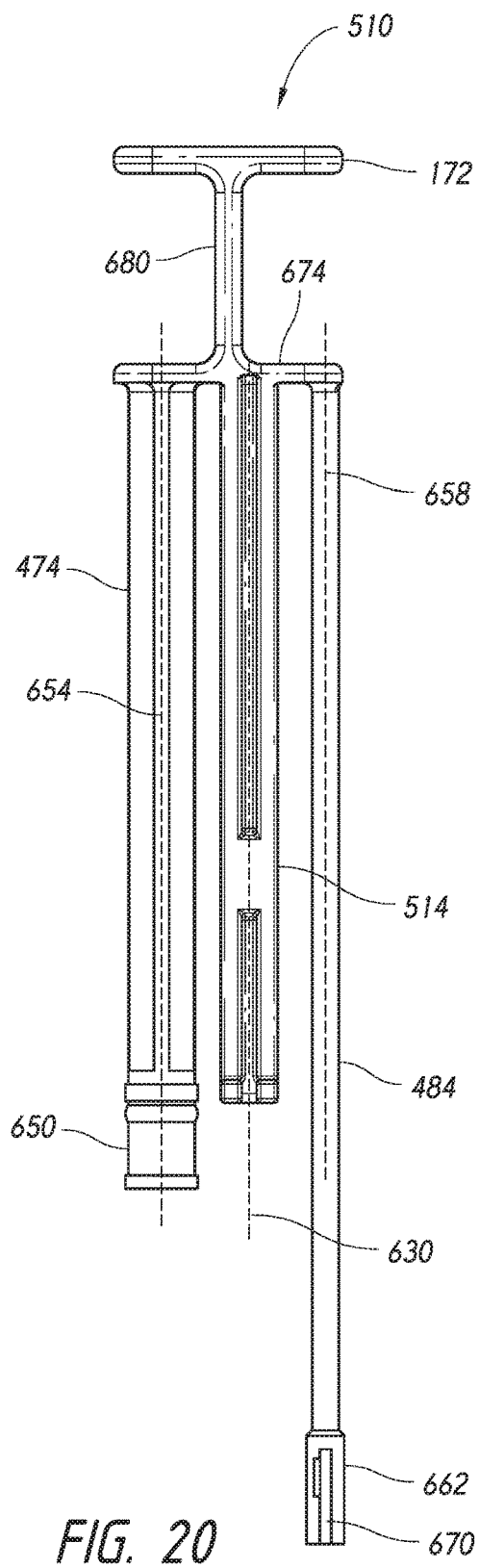
FIG. 20 illustrates a front view of the plunger assembly, according to some embodiments.

FIG. 20 illustrates a front view of the plunger assembly 510. The first plunger 474 can include a plunger seal 650 located on a distal end of the first plunger 474. The plunger seal 650 can be configured to form a fluid seal against a portion of the inside of the first barrel 470 (shown in FIG. 17). In some embodiments, the plunger seal 650 can be made of silicone. In some embodiments, the plunger seal 650 can include at least one O-ring and/or at least one wiper seal. The first plunger 474 can include a sixth central axis 654.

The plunger assembly 510 can include a shaft 484 with a seventh central axis 658. A distal end of the shaft 484 can include a coupler 662 configured to mechanically couple the shaft 484 to a piercing member 160 (shown in FIG. 16). The coupler 662 can be a slot 670 in the distal end portion of the shaft 484. A proximal portion of a piercing member can be configured to fit within the slot 670.

In several embodiments, the first plunger 474, the shaft 484, and/or the locking device 514 are approximately parallel to each other. In some embodiments, the first plunger 474 (or the sixth central axis 654) is oriented at an angle relative to the shaft 484 (or the seventh central axis 658), wherein the angle can be greater than or equal to about zero degrees and/or less than or equal to about 15 degrees; greater than or equal to about zero degrees and/or less than or equal to about 10 degrees; or greater than or equal to about zero degrees and/or less than or equal to about 5 degrees. In some embodiments, the first plunger 474 (or the sixth central axis 654) is oriented at an angle relative to the locking device 514 (or the fifth central axis 630), wherein the angle can be greater than or equal to about zero degrees and/or less than or equal to about 15 degrees; greater than or equal to about zero degrees and/or less than or equal to about 10 degrees; or greater than or equal to about zero degrees and/or less than or equal to about 5 degrees. In some embodiments, the shaft 484 (or the seventh central axis 658) is oriented at an angle relative to the locking device 514 (or the fifth central axis 630), wherein the angle can be greater than or equal to about zero degrees and/or less than or equal to about 15 degrees; greater than or equal to about zero degrees and/or less than or equal to about 10 degrees; or greater than or equal to about zero degrees and/or less than or equal to about 5 degrees.

In some embodiments, the shaft 484 extends farther distally than the first plunger 474 and/or the plunger seal 650. The shaft 484, the first plunger 474, and/or the plunger seal 650 can extend farther distally than the locking device 514. In some embodiments, the shaft 484, the first plunger 474, and/or the locking device 514 extend from a base 674 that is oriented perpendicularly relative to the shaft 484, the first plunger 474, and/or the locking device 514. The first plunger 474 and the shaft 484 can be located at least partially within barrels while the locking device 514 is located outside of and/or between the barrels.

The first plunger 474, the locking device 514, and the shaft 484 can be protrusions that extend in a distal direction from a base 674. In several embodiments, the first plunger 474, the locking device 514, and/or the shaft 484 can be spaced apart from each other. In some embodiments a plunger handle 172 can be coupled to the base 674. The plunger handle 172 can be located proximally relative to the base 674. In some embodiments an arm 680 can couple the plunger handle 172 to the base 674. The arm 680 can be a protrusion and/or a shaft. The arm 680, the first plunger 474, the locking device 514, and/or the shaft 484 can be approximately parallel to each other. In several embodiments, the arm 680, the first plunger 474, the locking device 514, and/or the shaft 484 can be within 10 degrees of being parallel to each other.

In some embodiments the vascular access system 140 can include a locking assembly 136. The locking assembly 136 can be configured to removably couple the vascular access assembly to the fluid extraction assembly 148 and/or to the access extraction assembly 152. The locking assembly can include a feature that latches onto a portion of the vascular access assembly 144 to inhibit or prevent the fluid extraction assembly 148 and/or the access extraction assembly 152 from inadvertently dislodging from the vascular access assembly 144 (or from a portion of the vascular access assembly 144).

As illustrated in FIG. 18, the locking assembly 136 can include a first securing tooth 690a, a second securing tooth 690b, a pivot 694 (e.g., as illustrated in FIGS. 16 and 18), a distal protrusion 698, and a lever 702 (e.g., a lever arm). Pressing the lever 702 in a first direction 706 can cause the securing teeth 690a, 690b to move in a second direction 710 (e.g., radially outward relative to the same axis), which can be opposite to the first direction 706. The lever 702 can be located on the proximal side of the pivot 694, which is shown inside of a dashed box. The distal protrusion 698 can be a second lever located on the distal side of the pivot 694. The pivot 694 can be located between the first barrel 470 and the second barrel 480 (shown in FIG. 17).

The locking device 514 can inhibit or prevent a user from moving the lever 702 in the first direction 706. In other words, the locking device 514 can interfere with movement in the first direction 706 when the locking device 514 is in the path of the movement. A user can move the plunger assembly 510 proximally to cause the locking device 514 to move proximally. Once the locking device 514 and/or the plunger assembly 510 is in a sufficiently proximal position, the locking device 514 and the plunger assembly 510 no longer impede, limit, and/or prevent pressing the lever 702 in the first direction 706 to enable the first securing tooth 690a and/or the second securing tooth 690b to move sufficiently far in the second direction 710 to clear the locking tooth 224 shown in FIG. 12.

In some embodiments, the first securing tooth 690a and/or the second securing tooth 690b can be protrusions that extend at least partially perpendicularly to the distal direction and/or to a central axis of a barrel. The locking tooth 224 can be an indentation configured such that at least a portion of the protrusion can enter therein. In several embodiments, the first securing tooth 690a and/or the second securing tooth 690b removably couple with a surface of a vascular access assembly, wherein the surface can generally face distally.

The locking device 514 can include protrusions on each side of a portion of the lever 702. The protrusions can be configured to inhibit or prevent the lever 702 from slipping to either side of the locking device 514 (and thus allowing undesirable movement in the first direction 706 before the plunger handle 172 is in a sufficiently proximal position). Preferably, a sufficiently proximal position is a position where a piercing member (e.g., a needle) is fully enclosed in a protective housing, such as a barrel.

In a first locked position, the first securing tooth 690a can couple with the locking tooth 224. In a second locked position, the second securing tooth 690b can couple with the locking tooth 224. The first securing tooth 690a can be located distally relative to the second securing tooth 690b. Placing the components in the second locking position can cause the piercing member 160 to protrude from the catheter 164. In the first locking position, the distal end of the piercing member 160 can be located inside of the catheter (e.g., to help protect medical professionals from the piercing member 160).

The extraction assembly 464 (shown in FIG. 16) can be located more proximally in the first locked position than in the second locked position. In some embodiments, the purpose of having more than one locked position is to avoid seal aging issues. In other words, in several embodiments, a seal that is left in an "open" position for too long might develop compression set and be unable to sufficiently seal or close in the future. While this consideration does not necessarily apply to all embodiments, the first locked position can couple an extraction assembly (e.g., 464 in FIG. 16) to a vascular access assembly (e.g., 144 in FIG. 7) without placing a seal (e.g., the second seal 280) in an open position and/or without opening a fluid passage (or channel) between an internal portion of the extraction assembly and an internal portion of the vascular access assembly.

Figure 21:
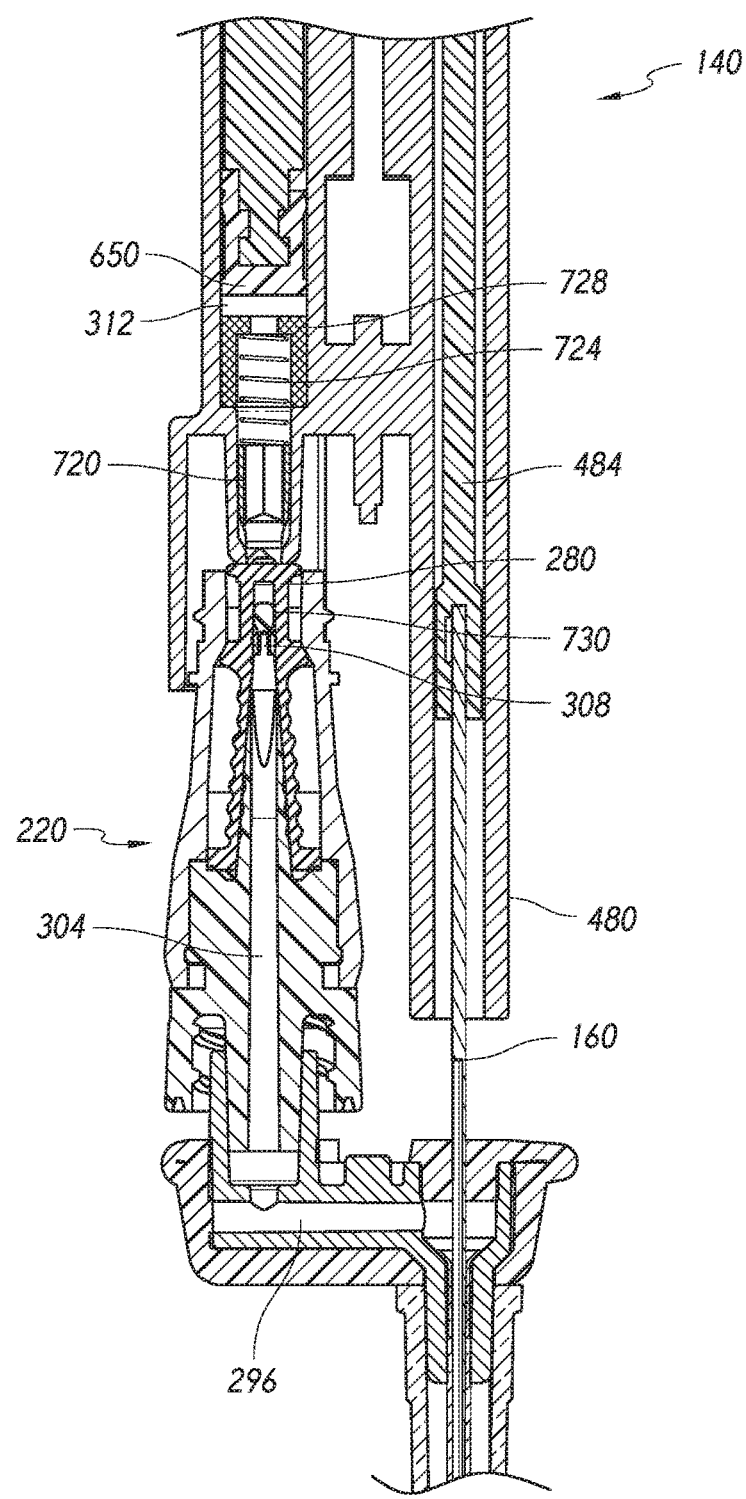
FIG. 21 illustrates a cross-sectional view of the vascular access system in the first locked position, according to some embodiments.

FIG. 21 illustrates a cross-sectional view of the vascular access system 140 in the first locked position. In the first locked position, the second seal 280 seals the exit 308 such that the third passage 304 is not in fluid communication with the first reservoir 312. In some embodiments a third seal 720 (e.g., a flow controller) can be used to seal a distal exit to the first reservoir 312. A spring 724 can push the third seal 720 in a distal direction. Moving the third seal 720 in a distal direction can cause the third seal 720 to seal against a tapered surface. In some embodiments the third seal 720 can include a tapered portion that seals, blocks, and/or closes against a tapered portion of a fluid extraction assembly in a seal zone. The third seal 720 and/or the second seal 280 can be one or more flow controllers and/or valves.

Figure 22:
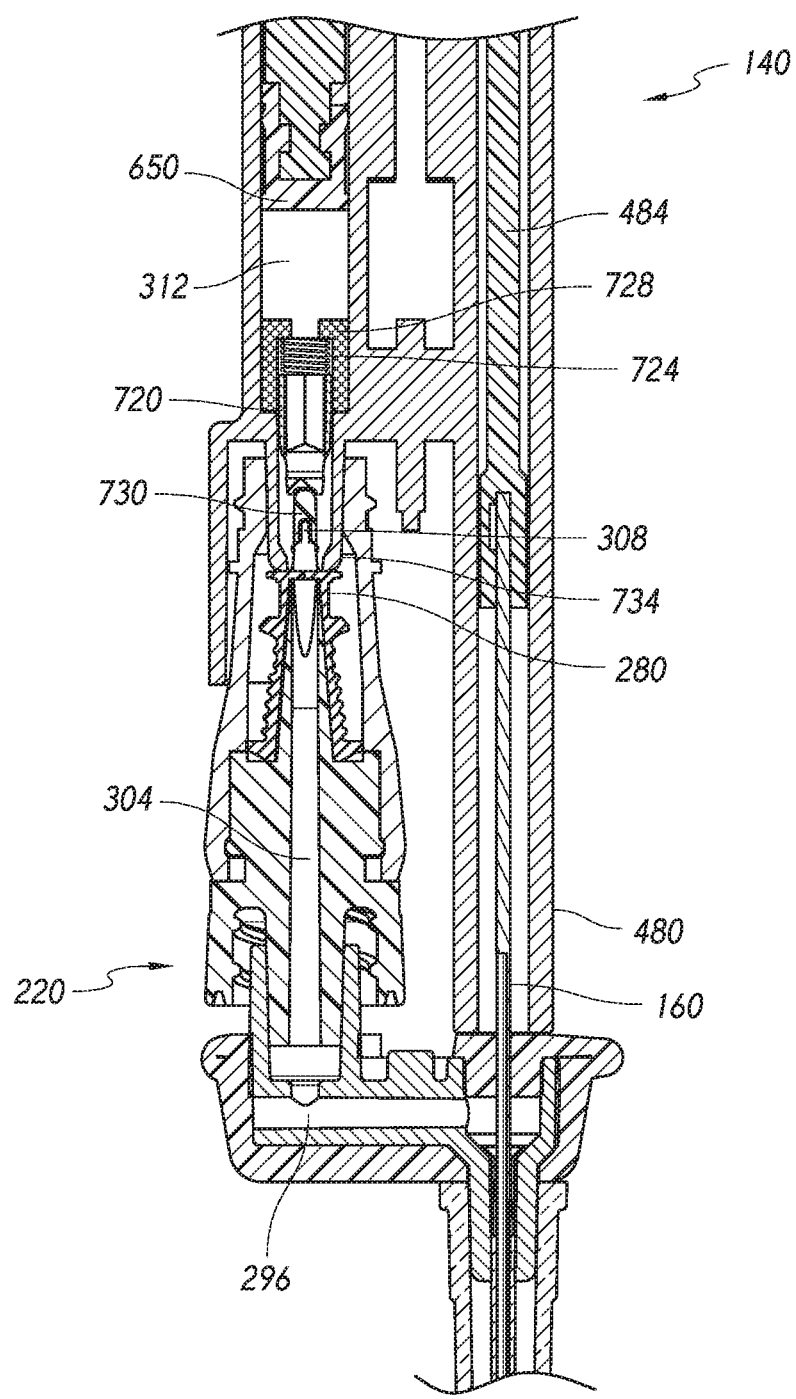
FIG. 22 illustrates a cross-sectional view of the vascular access system in the second locked position, according to some embodiments.

FIG. 22 illustrates a cross-sectional view of the vascular access system 140 in the second locked position. The connector 220 can include a proximal protrusion 730, which can be a shaft, rod, or tube. In some embodiments, the connector 220 can be in a second locked position when the vascular access system is in the second locked position. When the connector is in the second locked position, the proximal protrusion 730 can force the third seal 720 to move proximally, which can place the third passage 304 in fluid communication with the first reservoir 312. A tube 734, which in some embodiments can be a portion of the extraction assembly 464, can move the second seal 280 distally and into an open position. In some embodiments the tube can also compress the second seal. When the second seal is in an open position, the exit 308 can be exposed to place the third passage 304 in fluid communication with the first reservoir 312. Moving from the first locked position to the second locked position can include moving the proximal protrusion 730 into contact with the third seal 720 (e.g., by passing into the tube 734) and moving the third seal proximally, compressing the spring 724.

In some embodiments, as described further below, needleless connectors can be used that do not have a proximal protrusion to help move the third seal proximally. In some such embodiments, such as illustrated by example in FIG. 23, third seal 720 may be attached to struts 731 that can extend substantially parallel to the third seal. The struts may extend through a base surface 733 at a proximal end of tube 734. They may slide through the base surface and sealingly engage the base surface so that fluid does not leak. In some embodiments, the struts may be integrally formed with the third seal. In some embodiments, the struts may be formed separately and later attached to the third seal.

In some embodiments, the proximal protrusion can extend further into the second seal than illustrated in FIGS. 21 and 22 when the vascular access system is in the first locked position. The medical connector 220' of FIG. 9 provides an example of one such embodiment. FIG. 9 illustrates a cross-sectional view of the medical connector 220' of FIG. 9. As shown, in some embodiments the proximal protrusion 730' can extend through the second seal 280' to a proximal face of the second seal when the access system is in the first locked position. When the second seal 280' is moved distally into the open position, it can expose the exit 308' and place the third passage 304' into fluid communication with the first reservoir 312.

In some embodiments, instead of having a proximal protrusion that defines an internal conduit, such as the third passage, the second seal can at least partially define the third passage. The medical connector 220" of FIGS. 10 and 11 provides an example of one such embodiment. FIG. 10 illustrates a cross-sectional view of the medical connector 220" of FIGS. 10 and 11, and FIG. 11 illustrates a cross-sectional view of the connector 220" rotated 90 degrees. As illustrated, the second seal 280" can define a portion of the third passage 304".

In some embodiments, for example as further shown by the medical connector 220", a second seal 280" can be configured to remain in the same position when the vascular access system is in the first locked position and when the vascular access system is in the second locked position. When the vascular access system moves to the second locked position, instead of having a tube 734 move the second seal distally, the tube can pass through a slit 281" of the second seal, opening the slit to place the third passage 304" in fluid communication with a first reservoir 312.

Figure 23:
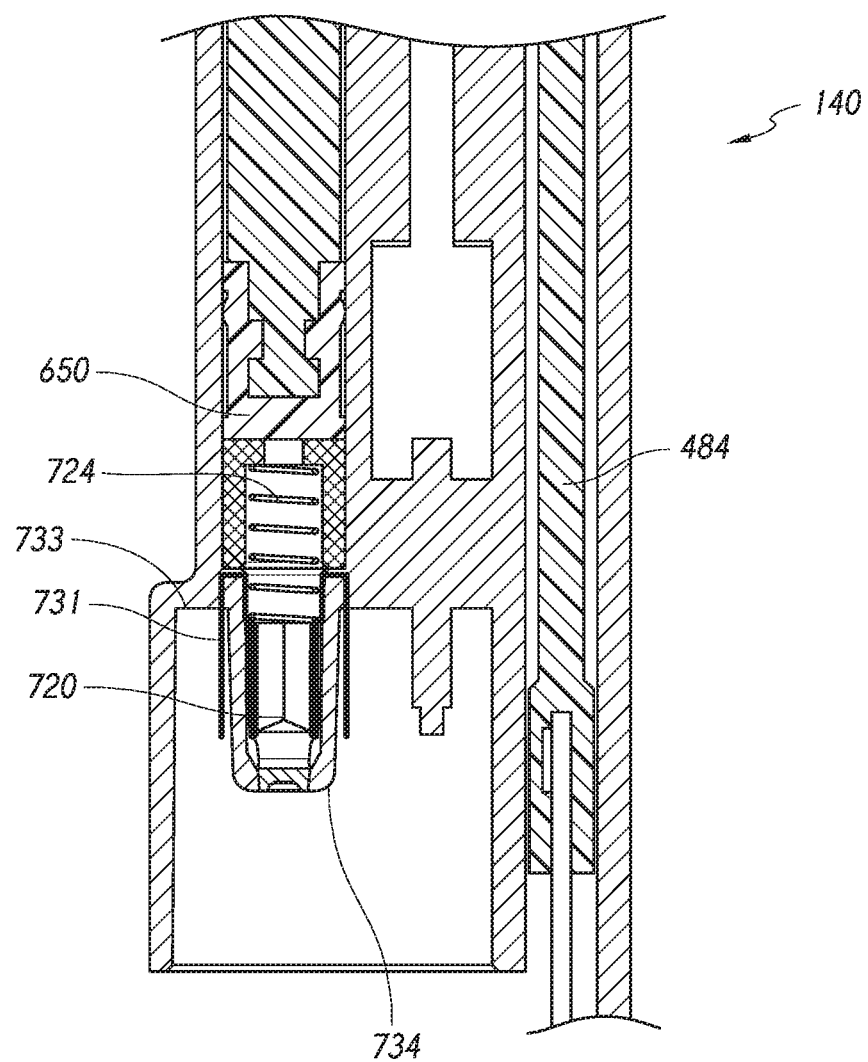
FIG. 23 illustrates a cross-sectional view of a portion of a vascular access system, according to some embodiments.

In some embodiments, also as shown by example in FIGS. 10 and 11, a medical connector 220" may not include a proximal protrusion 730. In some such embodiments, the connector 220" can be used with a vascular access system that includes struts 731 attached to third seal 720 (for example, as shown in FIG. 23). The struts may engage an end surface 233" of the connector as the connector moves toward the second locked position. The end surface may move the struts and third seal proximally to open fluid communication with the first reservoir 312.

In various embodiments, medical connectors used with a vascular access system can combine one or more of the different features discussed herein. For example, in some embodiments a medical connector can include a proximal protrusion that extends all the way through a second seal but can have a shoulder instead of a circumferential projection. In some embodiments, as a further example, a medical connector with a second seal and protrusion as shown in FIGS. 21 and 22 can be configured to have non-standard connections. Other combinations are considered.

Figure 24:
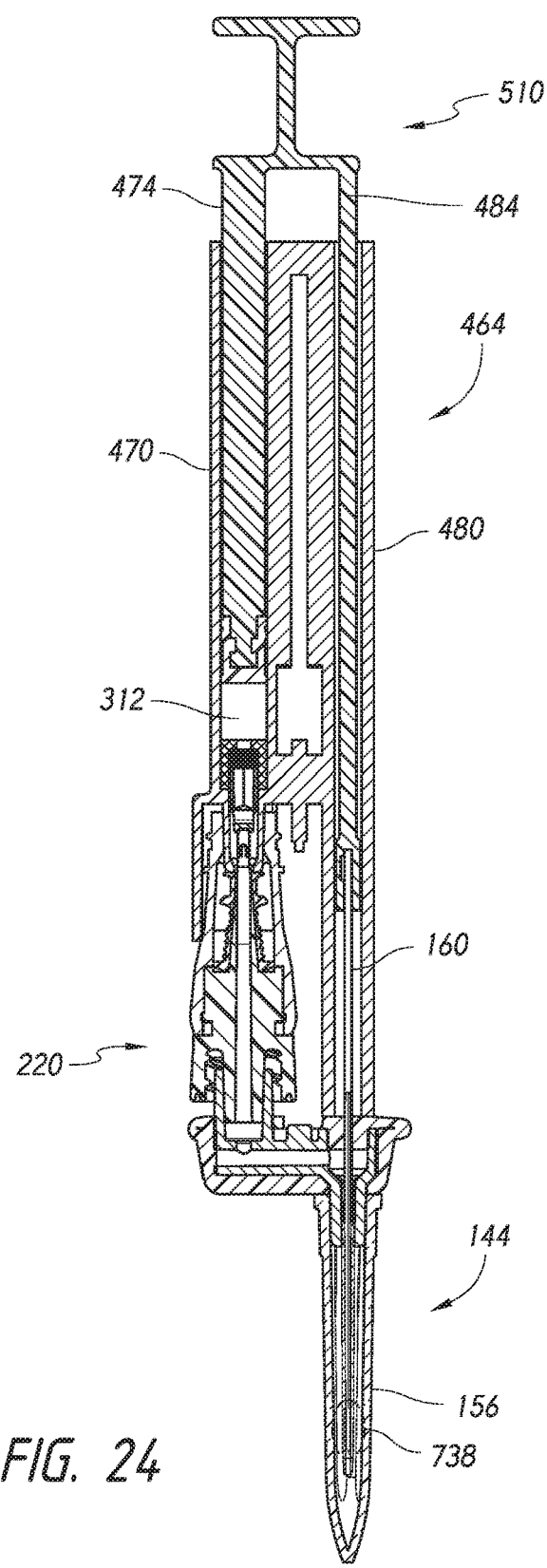
FIGS. 24 and 25 illustrate cross-sectional views of an extraction assembly coupled to a vascular access assembly, according to some embodiments.
Figure 25:
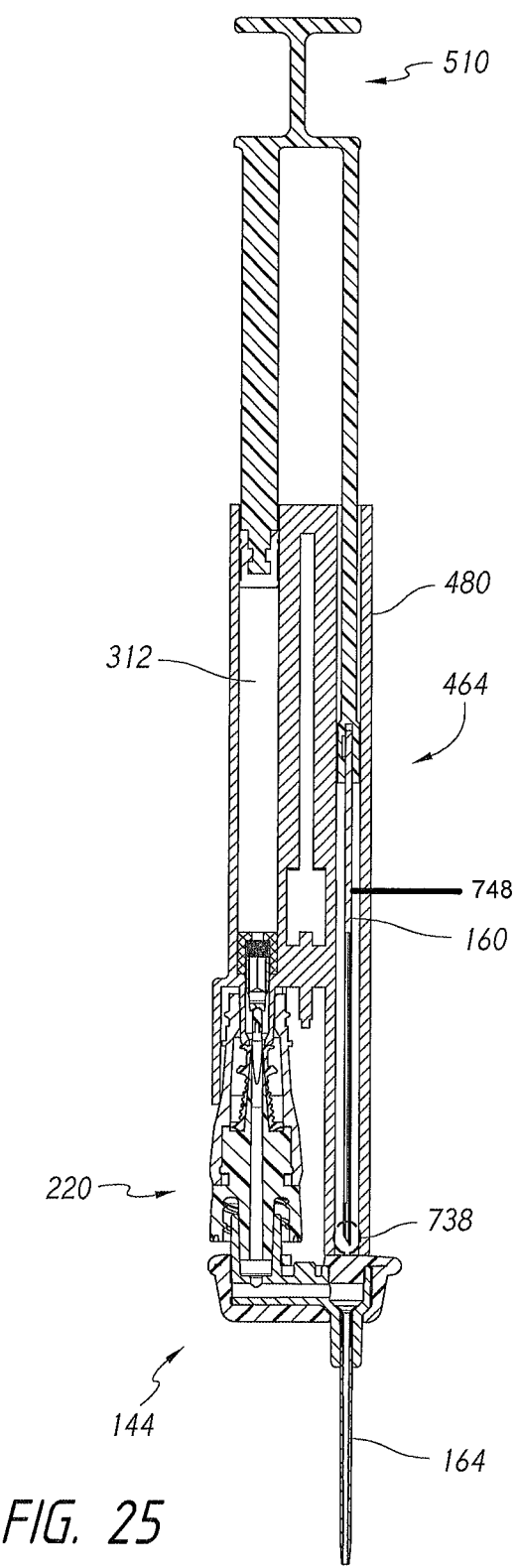

FIGS. 24 and 25 illustrate cross-sectional views of the extraction assembly 464 coupled to the vascular access assembly 144. In FIG. 24, a cap 156 covers a distal tip 738 of the piercing member 160. The plunger assembly 510 is in a more proximal location in FIG. 25 than in FIG. 24. Pulling the plunger assembly 510 sufficiently proximally can cause the distal tip 738 of the piercing member 160 to recede into the second barrel 480 and/or into a portion of the extraction assembly 464.

In FIG. 25, the fluid (e.g., gas, air) that was inside of the vascular access assembly 144 is now in the first reservoir 312 and the piercing member 160 that was used to access a patient's vein or artery is in the second barrel 480. Thus, the vascular access assembly 144 is primed and ready to be decoupled from the extraction assembly.

Figures 26, 27:
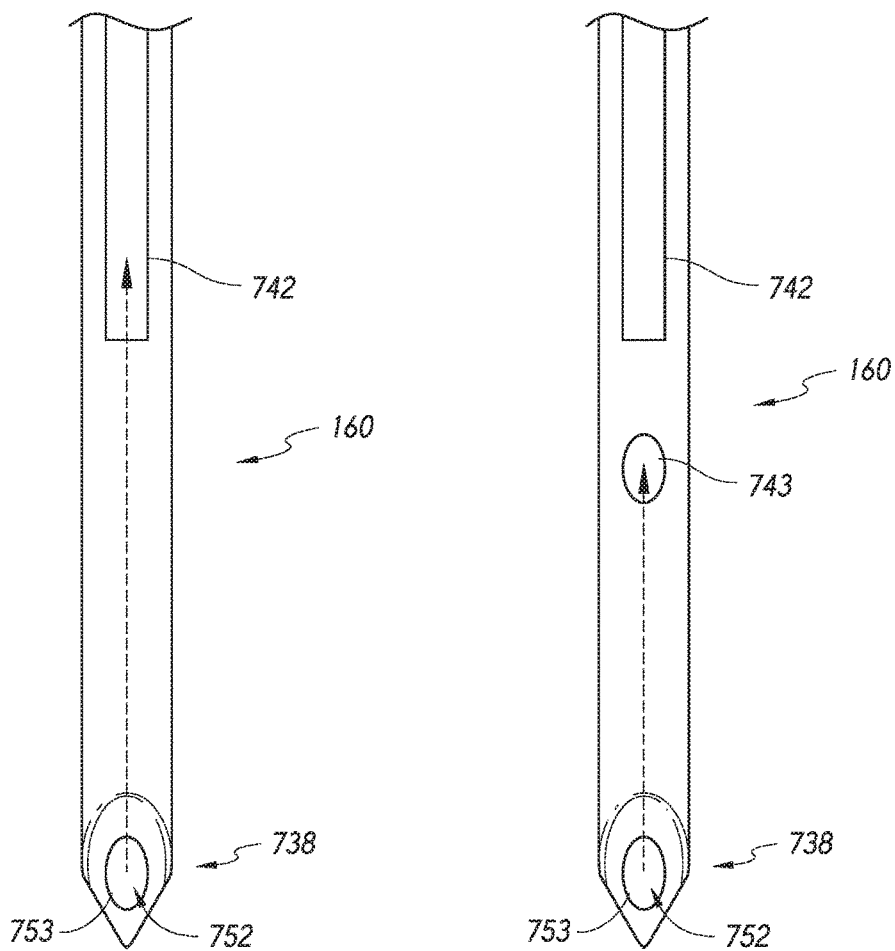
FIG. 26 illustrates a side view of a distal portion of the piercing member, according to some embodiments.
FIG. 27 illustrates a side view of a distal portion of the piercing member, according to some embodiments.

FIG. 26 illustrates a side view of a distal portion of the piercing member 160. The piercing member 160 can include passage 752 that leads from a distal tip 738 to a hole, such as a slot 742. The slot 742 can place the passage 752 in fluid communication with an area located to the side of the piercing member 160. Thus, for example, in some embodiments blood that flows into the passage opening 753 can flow out of the slot 742 and into the outer housing 204. In embodiments in which the outer housing is clear, this can provide a visual indication that the piercing member is properly positioned within a patient's vasculature. In some embodiments, the slot 742 can be oriented within +/−45 degrees of perpendicular to a central axis of the piercing member 160. The slot 742 can be located proximally relative to the passage opening 753 and/or relative to the distal tip 738. A portion of the piercing member 160 can be solid such that the portion does not include a lumen or passage. This solid area 748 (see, e.g., FIG. 25) can inhibit or prevent fluid from entering an internal area of the piercing member 160 (e.g., via the distal tip 738, passage 752, and/or the slot 742) and then reaching the proximal end 756 of the piercing member 160. The piercing member 160 can be approximately straight and can include a tapered and/or sharpened distal tip 738.

In some embodiments, as illustrated in FIG. 27, a piercing member 160 can have an additional opening, such as confirmation opening 743. In some embodiments, the confirmation opening 743 can be used to provide visual confirmation that the piercing member is properly positioned within a patient's vasculature. This can help minimize the blood flow required into the piercing member before confirmation can be provided, since blood will not need to flow all the way into the outer housing 204. Preferably, the opening 743 is aligned with the passage opening 753, which is typically aligned with a clinician's line of sight when inserting the piercing member into a patient. Where a clear or translucent catheter is used, blood that enters the passage 752 can be visible through the catheter in the opening 743. In some embodiments, this can create a red mark that is shaped like the opening (whether circular, oval, or other shape). The slot 742 can allow air within the piercing member to exit into the outer housing so that blood can flow into the passageway 752.

In some embodiments, a piercing member 160 can be sized as described according to FIG. 15 to create a seal between the piercing member and a catheter. In some embodiments, the distal most edge of the catheter can seal with the piercing member between the passage opening 753 and the confirmation opening 743. Preferably, the distance between the distal most edge 455 of the catheter (visible in FIG. 14) and a proximal edge of the confirmation opening 743 is greater than the thickness of a patient's tissue between an external layer of skin and the blood vessel to be pierced. This can ensure that when the catheter and piercing member are inserted in the blood vessel, at least a portion of the confirmation opening 743 will be visible. In some embodiments, the distance between the distal most edge 455 of the catheter (visible in FIG. 14) and a distal edge of the confirmation opening 743 is greater than the thickness of a patient's tissue between an external layer of skin and a blood vessel. This can ensure that the entire confirmation opening 743 will be visible when the catheter and piercing member are inserted into the blood vessel.

Figure 28:
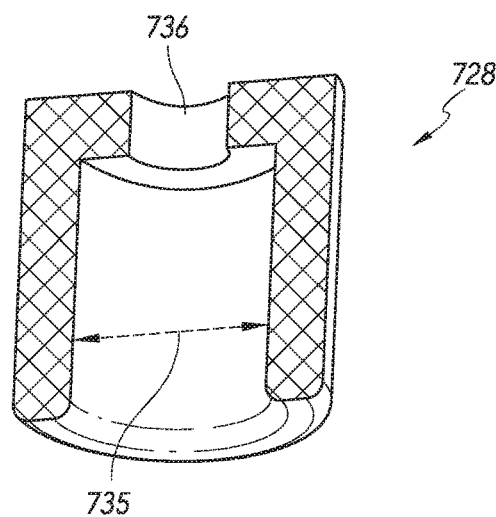
FIG. 28 illustrates a perspective, cross-sectional view of a spring retainer, according to some embodiments.

FIG. 28 illustrates a perspective, cross-sectional view of the spring retainer 728 from FIGS. 21 and 22. The spring retainer 728 can be fixedly attached to an interior of the extraction assembly 464 (e.g., to the first barrel 470). The spring retainer 728 can be configured to secure the spring 724 in place. In several embodiments, the spring retainer 728 is configured to limit the proximal movement of the proximal end of the spring 724. The spring retainer 728 can be at least partially cylindrical with an inner diameter 732 that is preferably greater than the outer diameter of the spring 724 and/or less than about 40% larger than the outer diameter of the spring 724. In some embodiments, the inner diameter 732 of the spring retainer 728 is less than about 20% larger than the outer diameter of the spring 724. A proximal end of the spring retainer 728 can include a hole 736 configured to allow fluid to pass through the spring retainer 728. The spring retainer 728 can be molded from rubber or plastic.

Figure 29:
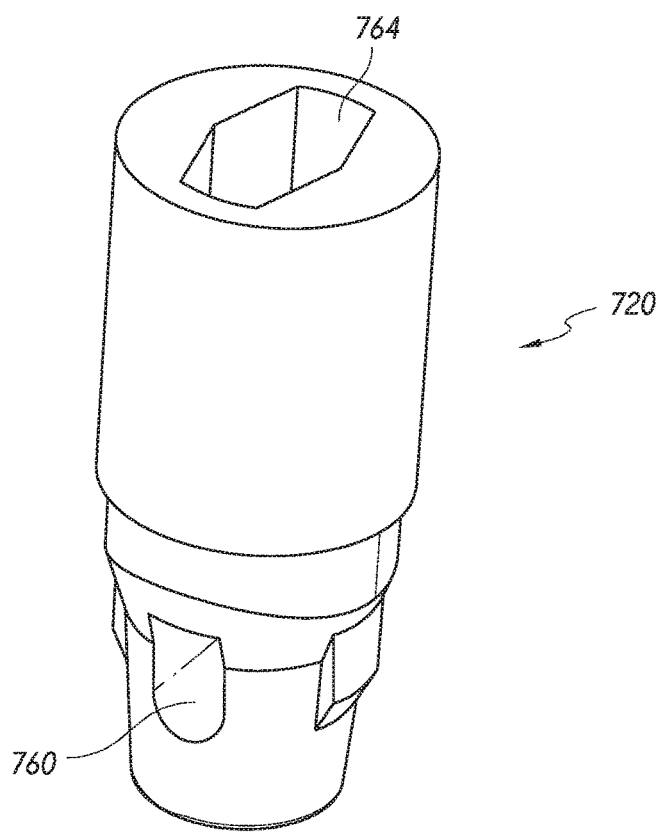
FIG. 29 illustrates a perspective view of a third seal, according to some embodiments.
Figure 30:
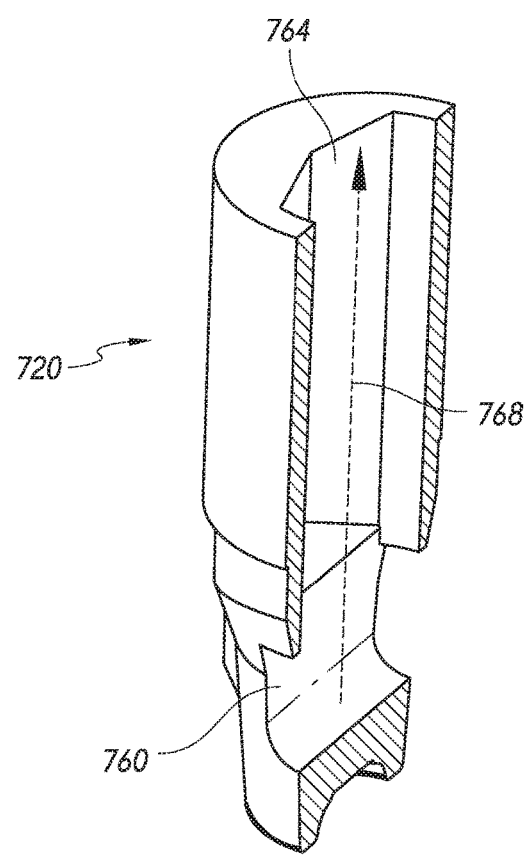
FIG. 30 illustrates a perspective, cross-sectional view of the third seal, according to some embodiments.

FIG. 29 illustrates a perspective view of the third seal 720, which in some embodiments can be a poppet. FIG. 30 illustrates a perspective, cross-sectional view of the third seal 720. Referring now to FIGS. 29 and 30, the third seal 720 can include a first hole 760 located in a distal half of the third seal 720. A second hole 764 can be located in the proximal half of the third seal 720. A passage 768 (depicted by a dashed line) can fluidly couple the first hole 760 to the second hole 764.

Figure 31:
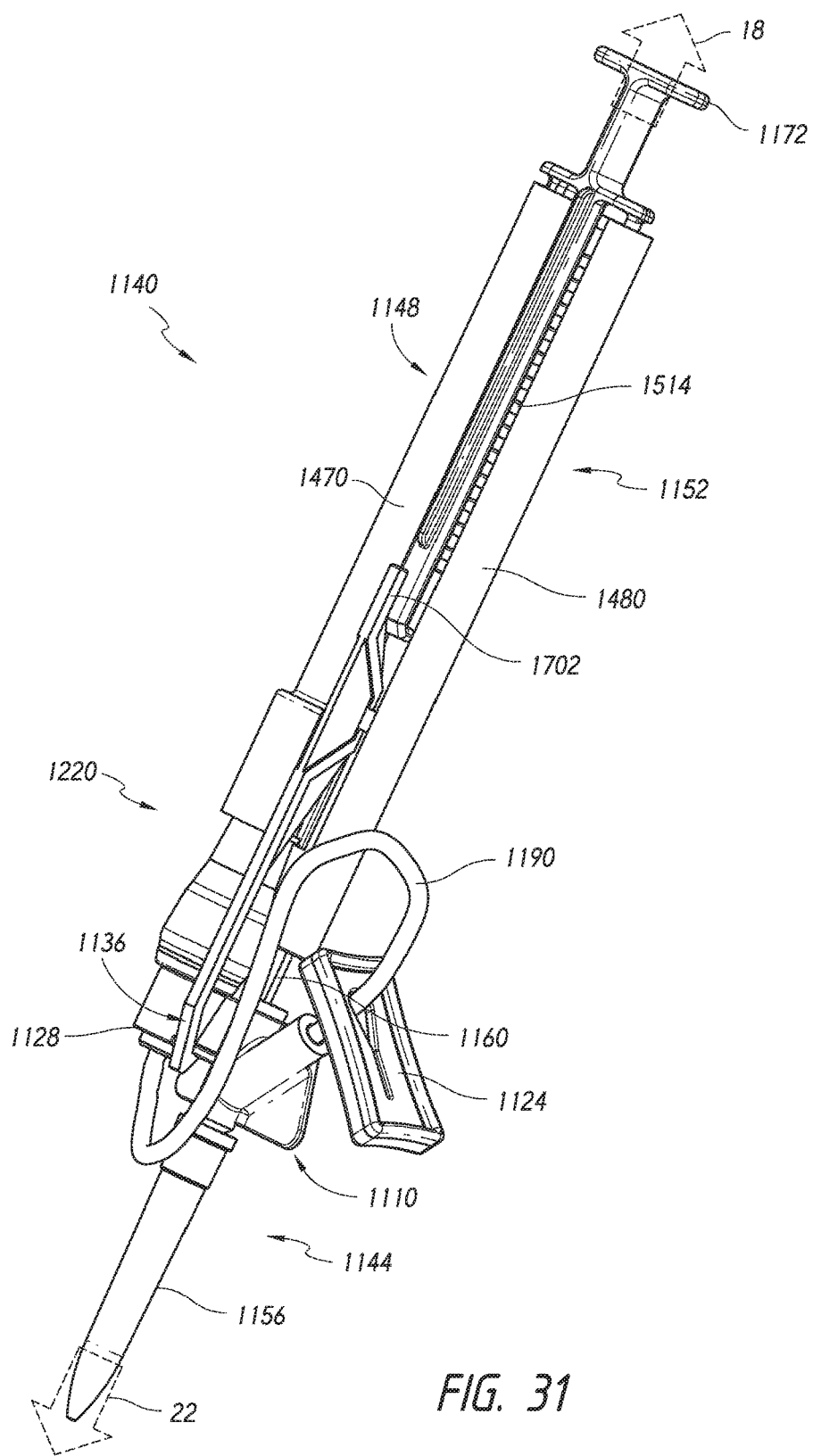
FIG. 31 illustrates a perspective view of a vascular access system that includes a tube that couples a connector to a catheter, according to some embodiments.

FIG. 31 illustrates a perspective view of a vascular access system 1140 that includes a tube 1190 that couples a connector 1220 to a catheter 1164. The system 1140 can be the same or identical to any of the other systems described herein and can include any of the features of those other systems.

In FIG. 31, the catheter 1164 is covered by a cap 1156, which can be a protective cover configured to inhibit or prevent inadvertent needle sticks and/or bending of the catheter 1164. The tube 1190 can be a flexible tube that is coupled (e.g., clipped, attached) to a housing 1110. The tube 1190 can enter a distal end of the connector 1220 and can be configured to enable fluid communication between the catheter 1164 and at least a portion of the connector 1220.

In some embodiments, once the fluid extraction assembly 1148 and the access extraction assembly 1152 are decoupled from the vascular access assembly 1144, the connector 1220 can be decoupled from a second clamp 1128 that secures the connector 1220 to the housing 1110 such that only the tube 1190 couples the connector 1220 to the housing 1110. In this configuration, the connector 1220 can move relative to the catheter 1164 to the extent permitted by the tube 1190. In several embodiments, the tube 1190 is flexible and at least two inches long, which allows the connector 1220 to be placed in many diverse orientations and locations relative to the catheter 1164. The fluid extraction assembly 1148 can include a syringe.

In several embodiments, the catheter 1164 and/or the housing 1110 are secured to a patient in a first orientation before the connector 1220 is secured to the patient in a second orientation, where the second orientation differs from the first orientation. The positional customization enabled by the tube 1190 can be helpful in some situations.

Figure 32:
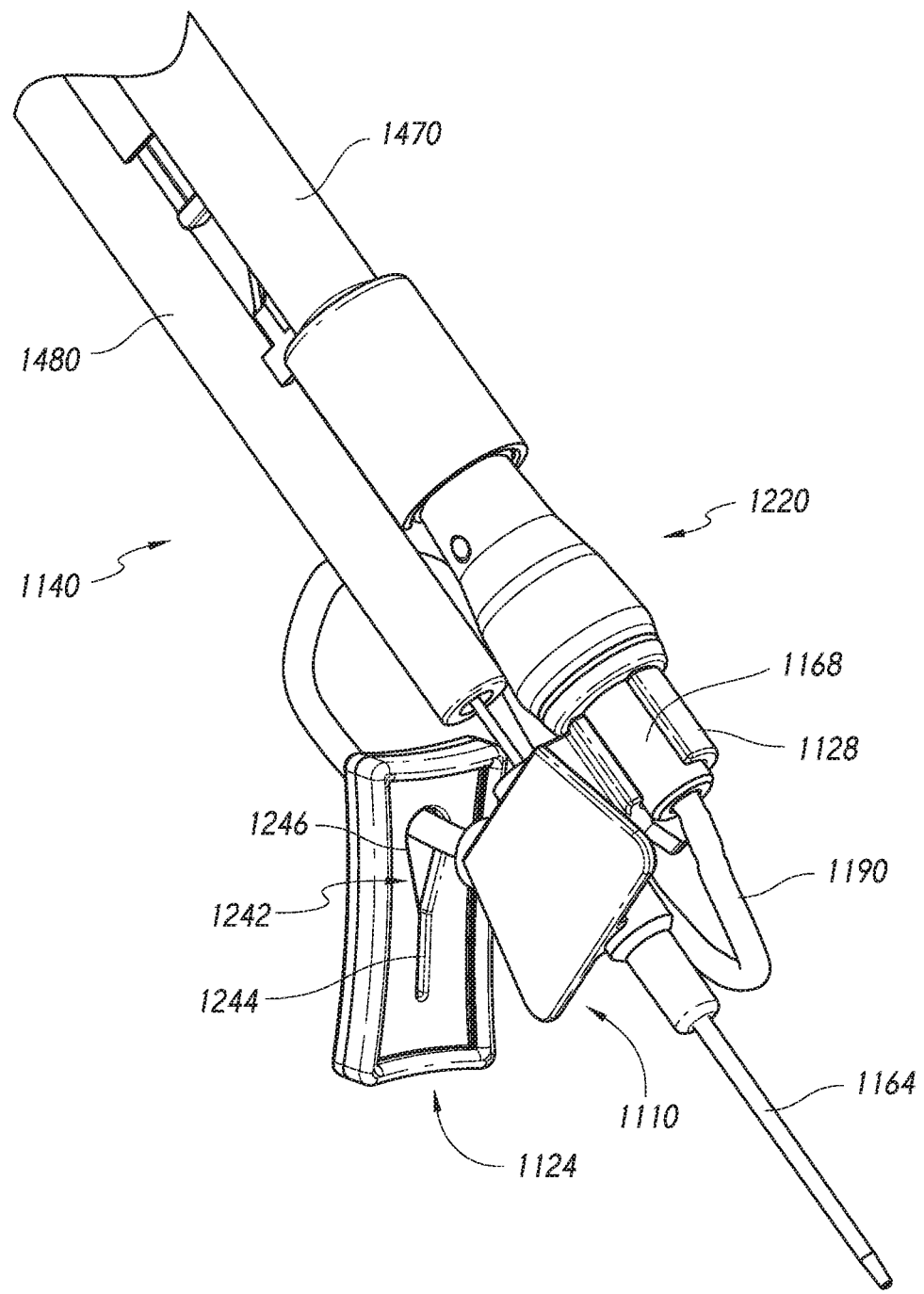
FIG. 32 illustrates a perspective view of a distal portion of the vascular access system, according to some embodiments.
Figure 35:
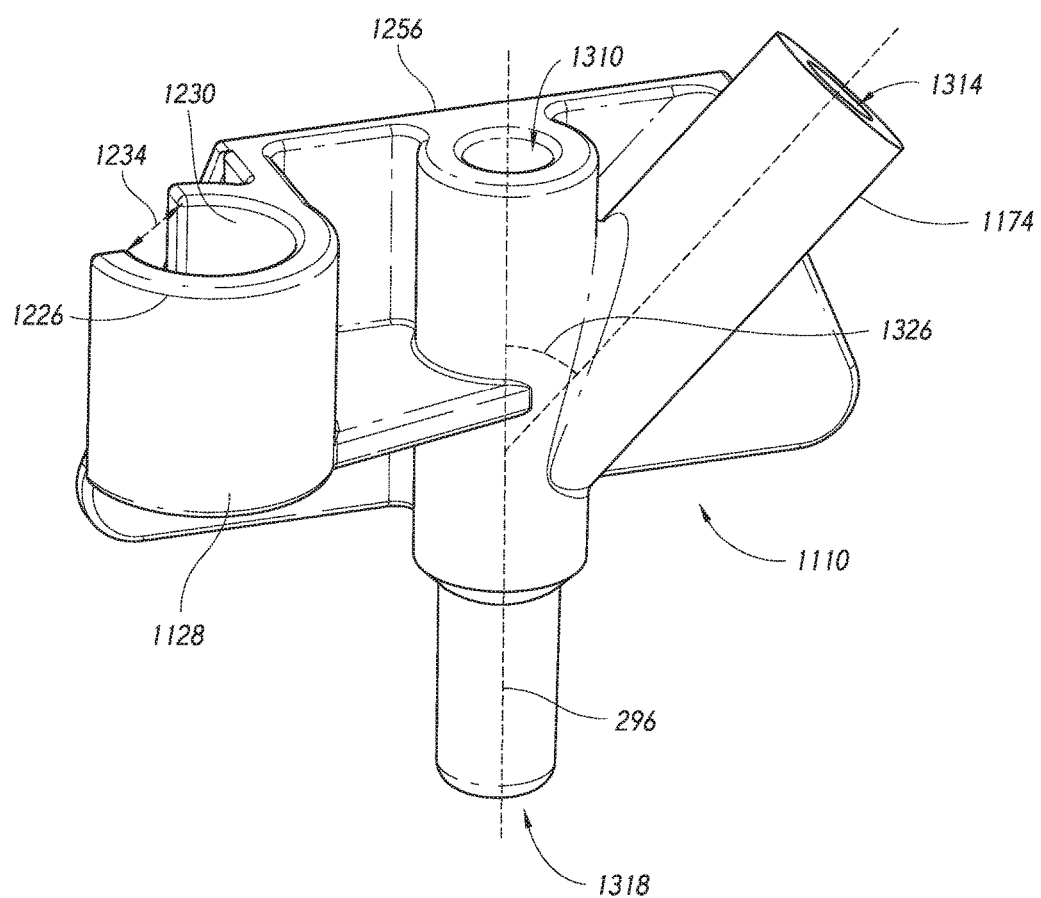
FIG. 35 illustrates a perspective view of a housing, according to some embodiments.

FIG. 32 illustrates a perspective view of a distal portion of the vascular access system 1140. Referring now to FIGS. 32 and 35, in some embodiments, the second clamp 1128 can include a cylindrical outer surface 1226 and/or a cylindrical inner surface 1230. The diameter of the cylindrical inner surface 1230 can be smaller than the outer diameter of a distal portion 1168 of the connector 1220. The second clamp 1128 can be configured to couple to the distal portion 1168 of the connector 1220, which can be cylindrical. In some configurations, the diameter of the cylindrical inner surface 1230 is at least about 3% smaller and/or less than or equal to about 50% smaller than the outer diameter of the distal portion 1168 of the connector 1220; at least about 5% smaller and/or less than or equal to about 35% smaller than the outer diameter of the distal portion 1168 of the connector 1220; or at least about 10% smaller and/or less than or equal to about 25% smaller than the outer diameter of the distal portion 1168 of the connector 1220.

The second clamp 1128 can be a C-clamp due to its "C" shape. The second clamp 1128 can include a gap 1234, which can be a slot. The gap 1234 can enable a portion of the connector 1220 to slide into and/or out of the second clamp 1128. The second clamp 1128 can hold the connector 1220 approximately parallel to the catheter 1164 (e.g., such that a central axis of the connector 1220 is within about +/−5 degrees, about +/−10 degrees, or about +/−15 degrees of being parallel to a central axis of the catheter 1164).

Referring now to FIG. 32, in some embodiments a first clamp 1124 can be placed around at least a portion of the tube 1190 to block and/or impede fluid flow through the tube 1190. Many different types of tube clamps can be used. Some embodiments use the first clamp 1124 illustrated in FIG. 32. The first clamp 1124 can include a keyhole 1242 with a first portion 1244 and a second portion 1246. The first portion 1244 can be narrower than the second portion 1246 (e.g., at least about 30% narrower, at least about 50% narrower, at least about 65% narrower). The first portion 1244 can be narrower than the outer diameter of the tube 1190 and/or the second portion can be wider than the outer diameter of the tube 1190. The first portion 1244 can be on a first end of the keyhole 1242 and the second portion 1246 can be on a second end (e.g., an opposite end) of the keyhole 1242.

The first clamp 1124 can be configured such that it cannot fit over the connector 1220 to inhibit or prevent the first clamp 1124 from falling off of the vascular access assembly 1144. The first clamp 1124 can include a hole (e.g., the keyhole 1242) through which the tube 1190 passes. The hole can be sized such that it is too small to enable the connector 1220 to pass through the hole.

The housing 1110 can include a flat surface 1256. A central axis of the connector 1220 and/or the first barrel 1470 (shown in FIG. 32) can be located farther away from the flat surface 1256 than the catheter 1164 and/or the second barrel 1480 (shown in FIG. 32) are located from the flat surface 1256.

In a first locked position (see FIG. 33), the first securing tooth 1690*a* can couple with a mating surface 1142 (e.g., a distally facing surface). In the second locked position, the second securing tooth 1690*b* can couple with the surface 1142. The first securing tooth 1690*a* can be located distally relative to the second securing tooth 1690*b*. Placing the components in the second locking position can cause the piercing member 1160 to protrude from the catheter 1164. In the first locking position, the distal end of the piercing member 160 can be located inside of the catheter 1164 (e.g., to help protect medical professionals from the piercing member 160). The first securing tooth 1690*a* or the second securing tooth 1690*b* can couple with a surface 1142 to form a lock that couples the syringe 1476 to the catheter 1164.

The surface 1142 can be any surface, indentation, and/or protrusion configured to "catch" and/or couple with a securing feature of the locking assembly 1136. The surface 1142 can be oriented perpendicularly relative to a central axis of the catheter 1164 and/or piercing member 1160. In several embodiments, the surface 1142 faces a distal direction.

Figure 34:
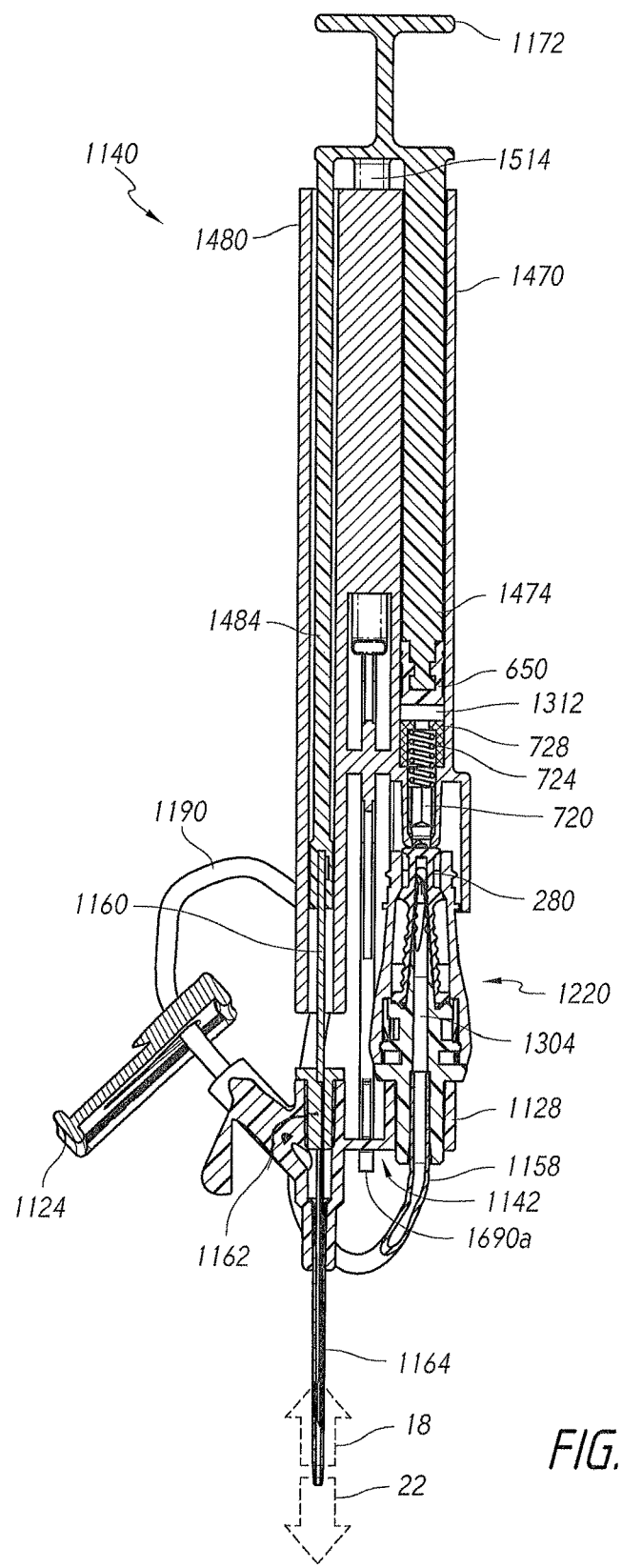
FIG. 34 illustrates a cross-sectional view of the vascular access system of FIG. 31, according to some embodiments.

FIG. 34 illustrates a cross-sectional view of the vascular access system 1140. Moving the plunger (e.g., the plunger handle 1172) proximally can simultaneously increase the volume of the first reservoir 1312 and retract the piercing member 1160 (e.g., move the piercing member 1160 proximally). A locking device 1514 similar to or the same as the locking device 514 can allow proximal movement of the plunger while preventing and/or inhibiting distal movement of the plunger (relative to the first barrel 1470 and/or second barrel 1480). At least a portion of the first plunger 1474 can slide within the first barrel 1470. A plunger seal 650 can be coupled to the first plunger 1474 to fluidly seal a portion of the first reservoir 1312 (e.g., fluidly seal a proximal end of the first reservoir 1312). At least a portion of the shaft 1484 can slide within the second barrel 1480.

The first reservoir 1312 can be placed in fluid communication with the third passage 1304 when the third seal 720 and the second seal 280 are in open positions to allow fluid to pass by the seals. The third passage 1304 can be in fluid communication with a tube passage 1158 (e.g., a lumen in the tube 1190). The tube passage 1158 can be in fluid communication with the second passage 296, which can be in fluid communication with a first passage 1300 (e.g., an internal channel of a catheter 1164). Fluid communication through portions of the vascular access assembly 1144 can enable the connector 1220, the first reservoir 1312 and/or portions of the first barrel 1470 (e.g., a syringe) to be in fluid communication with the catheter 1164 and/or a distal tip of the catheter 1164.

A fourth seal 1162 can be a plug through which a piercing member 1160 can pass (e.g., move distally and proximally). The fourth seal 1162 can be configured to seal around a solid area 748 of a piercing member 160 (shown in FIG. 25). In some embodiments, when the piercing member 1160, 160 is in a most distal position (e.g., when the piercing member extends from a catheter), the solid area 748 can be located at least partially inside of the fourth seal 1162. Thus, bodily fluid (e.g., blood) can move through the catheter and into the second passage 296, but can be blocked by the fourth seal 1162.

Figure 33:
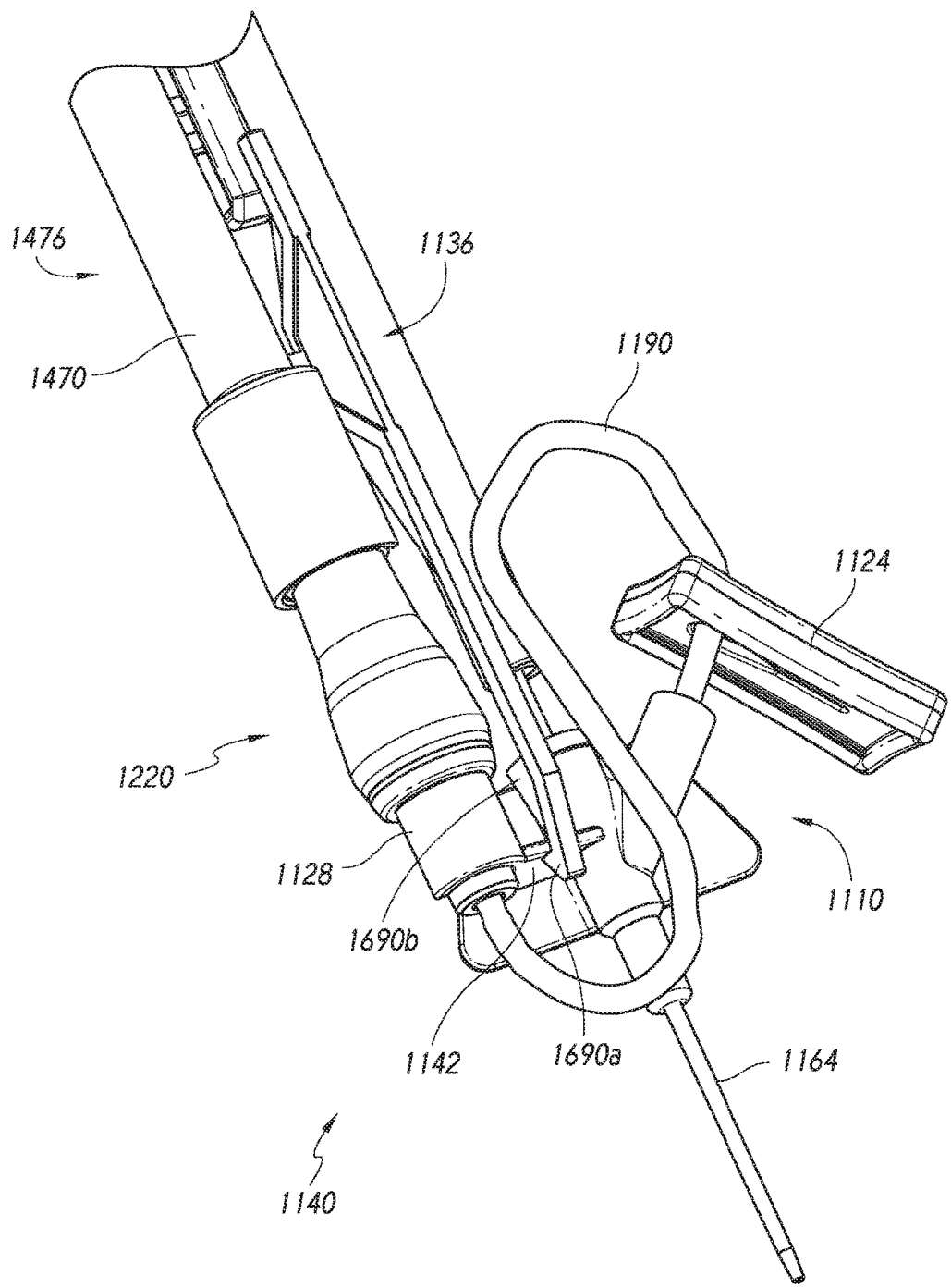
FIG. 33 illustrates a perspective view of a distal portion of the vascular access system in a first locked position, according to some embodiments.

The tube 1190 can extend proximally away from the catheter 1164, can extend distally towards the catheter 1164, and then can extend proximally into the connector 1220. The tube 1190 can form an "S" shape (e.g., as shown in FIG. 33).

The connector 1220 can be oriented in a proximal direction such that the end of the connector 1220 that is configured to couple to another device (e.g., a syringe) faces proximally. In some embodiments, the connector 1220 can be oriented in a distal direction or in a direction perpendicular to the central axis of the catheter 1164 (i.e., the first central axis 1260). In some embodiments, the second central axis 1264 is oriented within greater than or equal to about zero degrees and/or less than or equal to about 15 degrees relative to the first central axis 1260. In some embodiments, the second central axis 1264 is oriented within greater than or equal to about 15 degrees and/or less than or equal to about 75 degrees relative to the first central axis 1260. In some embodiments, the second central axis 1264 is oriented within greater than or equal to about 30 degrees and/or less than or equal to about 60 degrees relative to the first central axis 1260.

In several embodiments, the tube 1190 enters a support 1174 of the housing 1110. The tube can enter the housing 1110 and/or the support 1174 at an angle of greater than or equal to about 20 degrees and/or less than or equal to about 70 degrees relative to the first central axis 1260; or greater than or equal to about 40 degrees and/or less than or equal to about 50 degrees relative to the first central axis 1260.

FIG. 35 illustrates a perspective view of the housing 1110. In some embodiments, a vascular access assembly 1144 can include a piercing member extraction passage 1310 and a fluid extraction passage 1314. The piercing member extraction passage 1310 and the fluid extraction passage 1314 can include portions of the second passage 296.

The piercing member extraction passage 1310 can be coaxial with the catheter coupling passage 1318 and/or the first central axis 1260 of the catheter 1164 (see, e.g. FIG. 26). The second clamp 1128 can be located on one side of the piercing member extraction passage 1310 and the fluid extraction passage 1314 can be located on an opposite side of the piercing member extraction passage 1310. The vascular access assembly 1144 can include a catheter coupling passage 1318. A proximal portion of the catheter 1164 can be coupled to the catheter coupling passage 1318. The piercing member extraction passage 1310 and the fluid extraction passage 1314 can be fluidly coupled to the catheter coupling passage 1318 in a "Y" shape. The fluid extraction passage 1314 can be oriented at an angle 1326 relative to the piercing member extraction passage 1310. The angle 1326 can be greater than or equal to about 10 degrees and/or less than or equal to about 80 degrees; greater than or equal to about 25 degrees and/or less than or equal to about 70 degrees; or greater than or equal to about 40 degrees and/or less than or equal to about 50 degrees.

In some embodiments, a vascular access system can be configured such that creating a negative pressure to begin removing gas from the system and/or priming a connector can be decoupled or partially decoupled from the process of retracting a piercing member. Separating these processes can help, for example, when dealing with patients of varying blood pressure. Different blood pressures means that different amounts of negative pressure are needed to draw blood into the system before retracting the piercing member. In some embodiments, a vascular access system can also or alternatively include an auto-retract feature that automatically retracts the piercing member after the plunger has been partially withdrawn. This can help inhibit or prevent accidental punctures of the catheter by the piercing member when it is being retracted manually.

Figure 36:
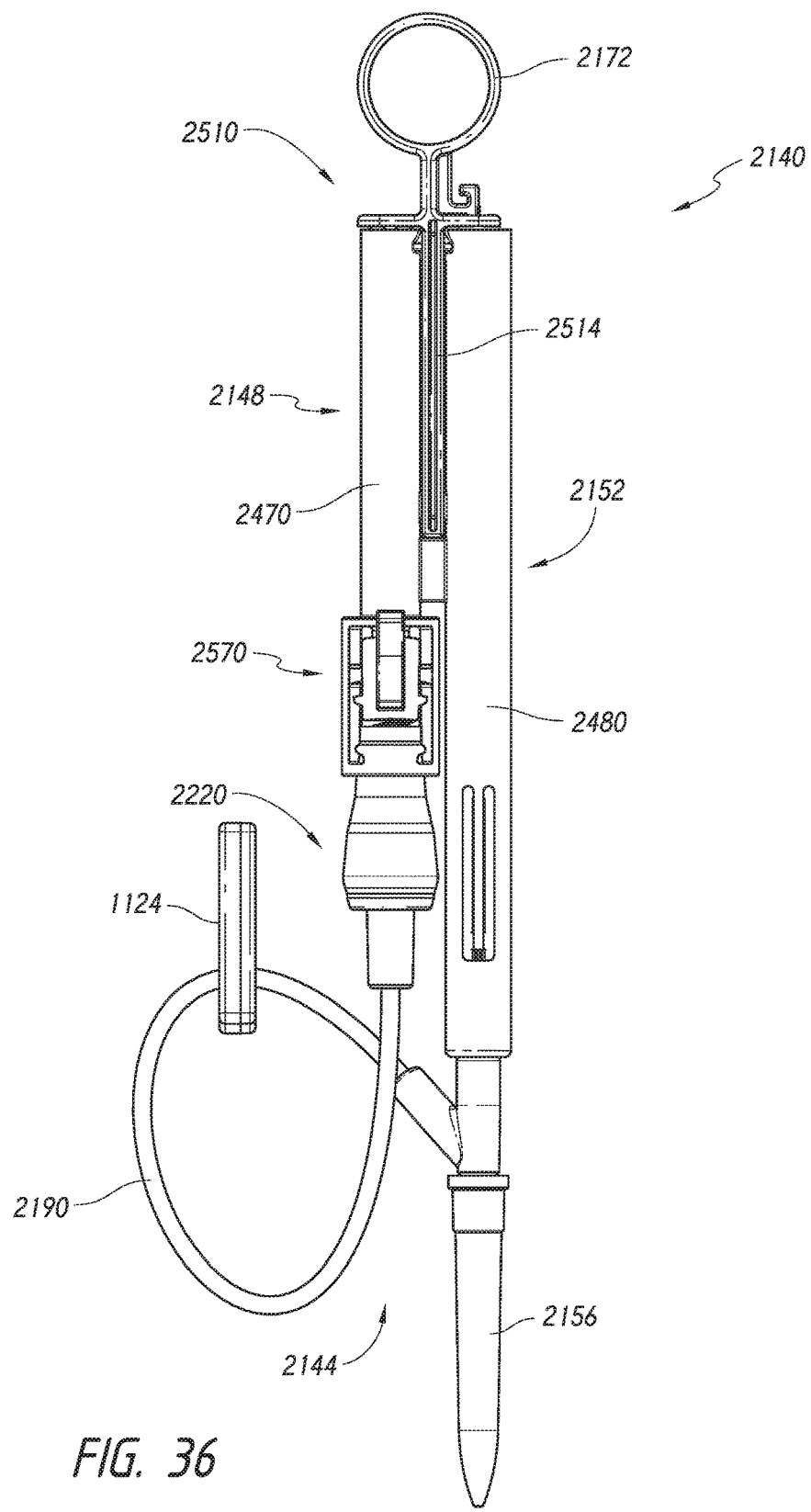
FIG. 36 illustrates a front view of a vascular access system, according to some embodiments.
Figure 37:
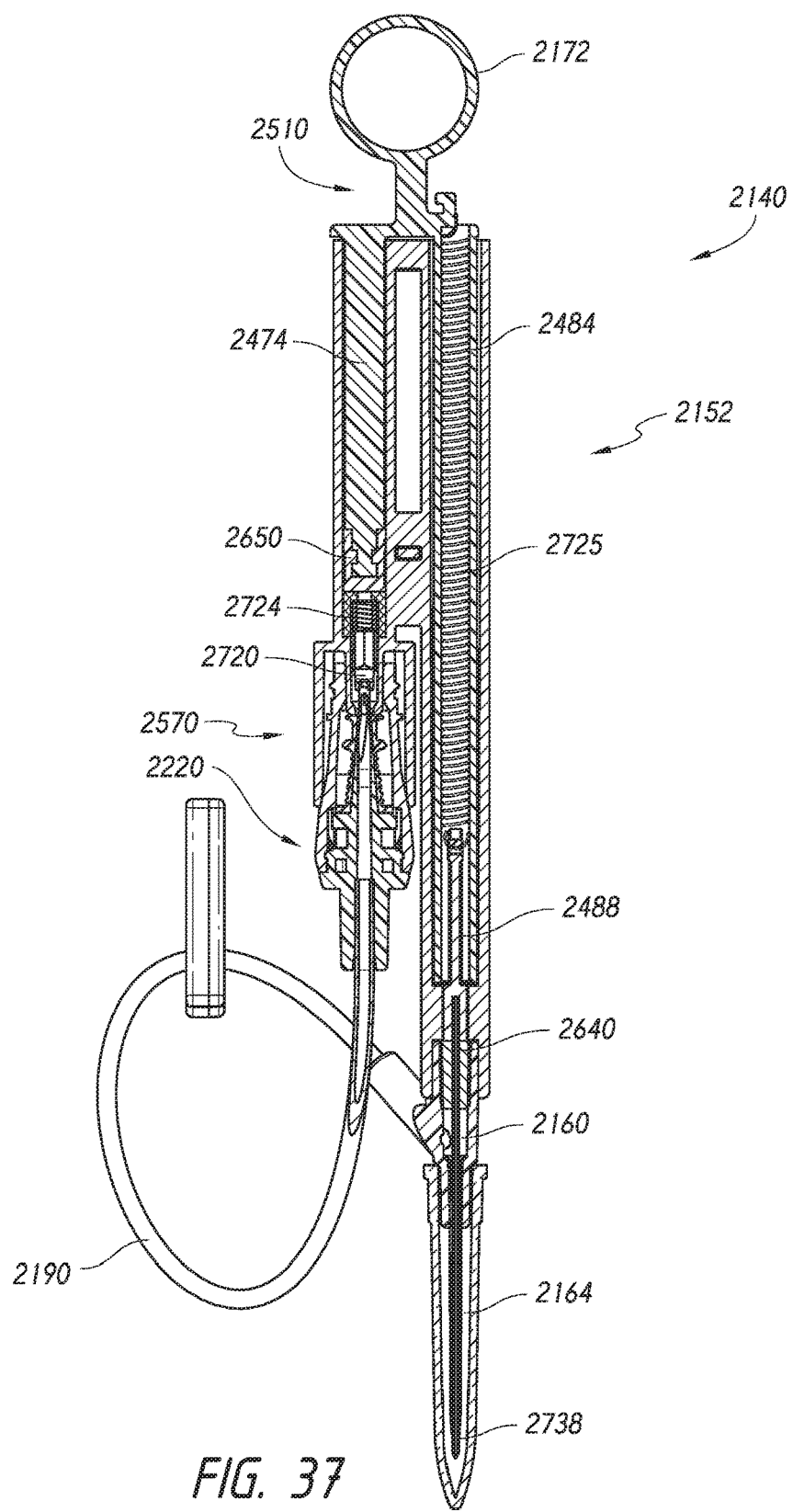
FIG. 37 illustrates a cross-sectional view of the vascular access system of FIG. 36.
Figure 38:
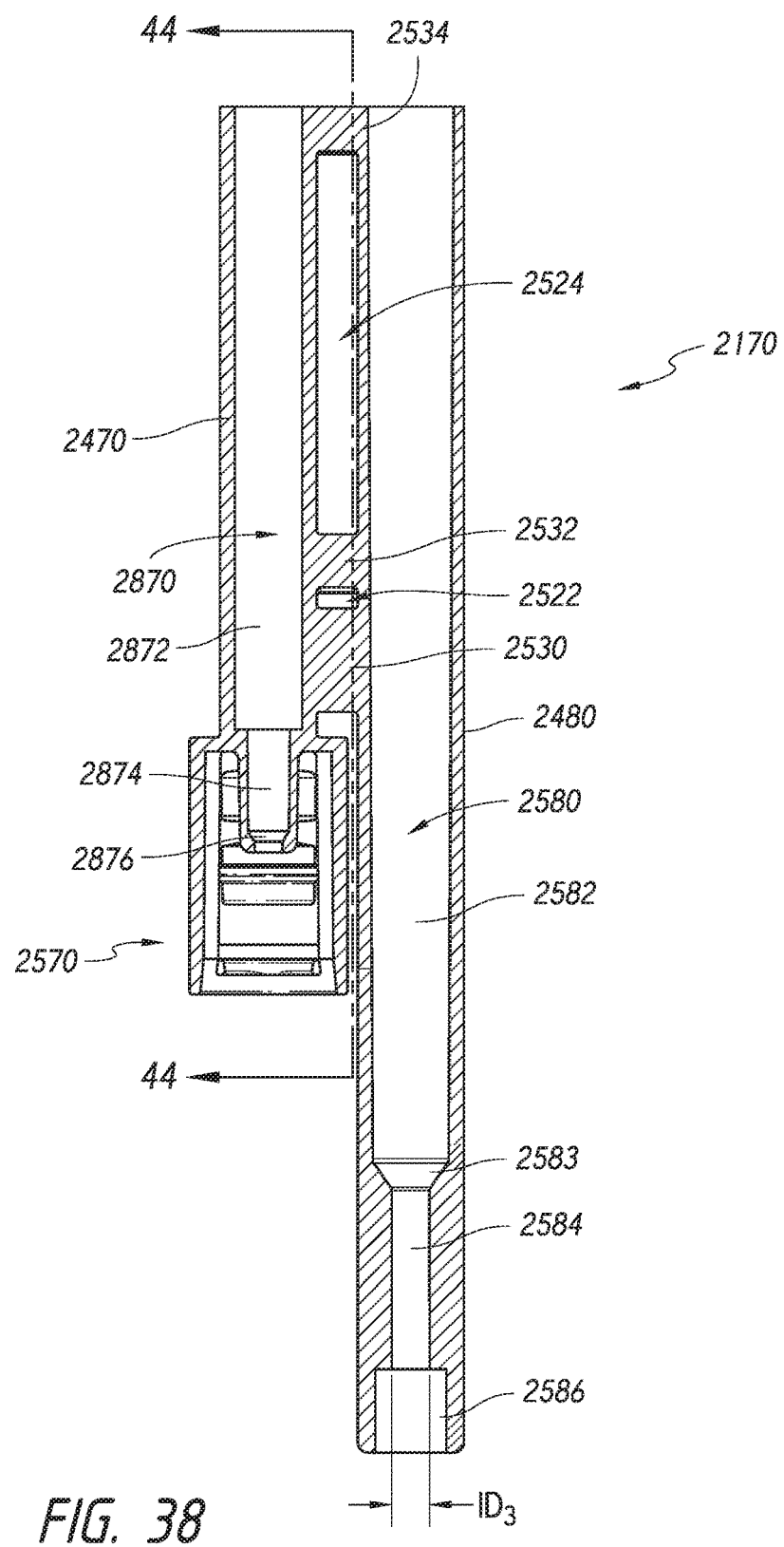
FIG. 38 illustrates a cross-sectional view of the extraction assembly housing of the vascular access system of FIG. 36.

FIGS. 36 and 37 illustrate one embodiment of a vascular access system 2140 that includes a mechanism to automatically retract a piercing member. FIG. 36 is a front view and FIG. 37 is a cross-sectional view taken in the same plane as FIG. 36. In FIGS. 37 and 38, and in subsequent figures, elements labeled with numbers similar to numbers from previous embodiments are understood to function as previously described, unless indicated otherwise. Thus, for example, the cap 2156 illustrated in FIG. 36 is understood to function the same as or similar to the cap 156 shown in FIG. 24 and the cap 1156 shown in FIG. 31. Further, although various components may be shown herein as opaque or translucent for purposes of illustration, it is understood that in various embodiments one or more components can be opaque or can be translucent, transparent, and/or clear such that fluid flow paths through the components are visible.

In some embodiments, as illustrated in FIGS. 37 and 38, an access extraction assembly 2152 of a vascular access system 2140 can include a second plunger 2484 that houses or partially houses a retraction spring 2725 or other biasing member. The retraction spring can be coupled to the piercing member 2160 and maintained in a tensioned state. When the plunger assembly 2510 has been withdrawn a defined distance, such as by pulling on the handle 2172, the retraction spring can be configured to release from its tensioned state, recoiling proximally into the second plunger 2484 toward an untensioned state and drawing the piercing member 2160 with it. In some embodiments, the length of the spring 2725 in the tensioned state can be at least about 1.5 times the length of the spring in the untensioned state. In some embodiments, the length of the spring 2725 in the tensioned state can be at least about 2 times the length of the spring in the untensioned state. In some embodiments, the length of the spring 2725 in the tensioned state can be at least about 3 times the length of the spring in the untensioned state.

In some embodiments, a locking device 2514 can be configured to allow the plunger assembly 2510 to move in a proximal direction while impeding motion in the distal direction, as described above. In some embodiments, the locking device can be configured to have one or more threshold positions. The vascular access system 2140 can be configured such that the locking device can be moved proximally past a threshold position but is blocked from moving distally past a threshold position. In some embodiments, threshold positions can be spaced such that the locking device can move distally and/or proximally between threshold positions.

In some embodiments, the vascular access system can be configured such that the piercing member 2160 automatically retracts when the plunger assembly moves proximally past a threshold position. Thus, once the piercing member has been automatically retracted, the plunger assembly is inhibited or prevented from moving further distally and thereby inhibited or prevented from re-exposing the piercing member. This can help inhibit or prevent accidental sticks.

In some embodiments, as illustrated, a piercing member holder 2640 can be used to couple the spring 2725 to the piercing member 2160. In some embodiments, a piercing member holder 2640 can also be used to help maintain the spring in the tensioned state. For example, in some embodiments the second plunger 2484 can have a second portion 2488 with walls that can be configured to flex radially inward. In a first, relaxed state the second portion can have an inner diameter sized to receive the entire piercing member holder. In some embodiments, the second barrel 2480 can include sections that interfere with the walls of the second portion, causing them to flex radially inward. This can shrink the inner diameter between the walls of the second portion and can block retraction of the piercing member holder 2640 and piercing member 2160. In some embodiments, drawing the plunger assembly 2510 distally can move the second portion 2488 of the second plunger 2484 to a position in which the walls of the second portion 2488 can return toward the first, relaxed state that can receive the piercing member holder, which can be retracted by the spring into the second plunger 2484. This is described in more detail below.

FIGS. 36 and 37 also illustrate an embodiment of a connector holder 2570 that can be used to attach a fluid extraction assembly 2148 to a connector, such as the needleless connector 2220. In some embodiments, the connector holder 2570 can couple to the connector 2220 in a first locked position without placing a seal of the connector in an open position and/or without opening a fluid passage or channel between an internal portion of the fluid extraction assembly and an internal portion of the vascular access assembly. Maintaining a connector and connector holder in the first locked position before use can help inhibit or prevent compression set, as described above.

In some embodiments, the connector 2220 can be moved relative to the connector holder 2570 and first barrel 2470 into a second locked position in which a seal of the connector 2220 is opened and a fluid passageway is established between an internal portion of the fluid extraction assembly 2148 and an internal portion of the vascular access assembly 2144. The seal in the connector can be opened and the fluid passageway established in the same manner as described above, such as with respect to FIGS. 21-22 and FIGS. 29-30. The first and second locked positions are also described in more detail below.

FIG. 38 illustrates a front cross-sectional view of one embodiment of an extraction assembly housing 2170 for use with a vascular access system 2140. In some embodiments, as illustrated in FIG. 38, the first barrel 2470 and the second barrel 2480 can each have an inner chamber 2870, 2580, respectively. In some embodiments, the inner chambers can have different sections of varying diameter. For example, in some embodiments the inner chamber 2870 of the first barrel can have a first section 2872 that can help define a first reservoir, such as the first reservoir 312 discussed with respect to FIG. 21. The first barrel can also have a second section 2874 with an inner diameter narrower than the inner diameter of the first section. In some embodiments, the second section can be configured to at least partially receive a third seal 2720 (illustrated in FIG. 37). In some embodiments, the first barrel can also have a third section 2876, which can preferably include a taper and can be configured to seat the third seal.

Similarly, in some embodiments the inner chamber 2580 of the second barrel can include at least a first section 2582 and a second section 2584. The second section preferably has an inner diameter $ID_3$ that is narrower than the inner diameter of the first section. In some embodiments, a tapered section 2583 can join the first and second sections. In some embodiments, the second section can have an inner diameter $ID_3$. In some embodiments, the inner diameter $ID_3$ can be generally constant. In some embodiments, the second section can have an inner diameter that narrows from the proximal end of the second section to the distal end of the second section, and the inner diameter $ID_3$ can refer to the maximum inner diameter of the second section.

In some embodiments, the second barrel can also include a third section 2586 positioned distal to the second section 2584. The third section can be configured to receive a portion of a housing, such as a housing similar to the housing 1110 described with respect to FIG. 35. In some embodiments, the inner diameter of the third section can be greater than the inner diameter $ID_3$ of the second section.

In some embodiments, the extraction assembly housing can include one or more connecting or locking sections, such as first section 2530, that join the first barrel 2470 with the second barrel 2480. In some embodiments, the connecting sections can define threshold locking positions for the locking device 2514, as discussed above. Locking channels, such as a second channel 2524 between the second section 2532 and the third section 2534, can receive a projection of the locking device 2514 and can define areas that allow for unimpeded movement of the locking device.

Figure 39:
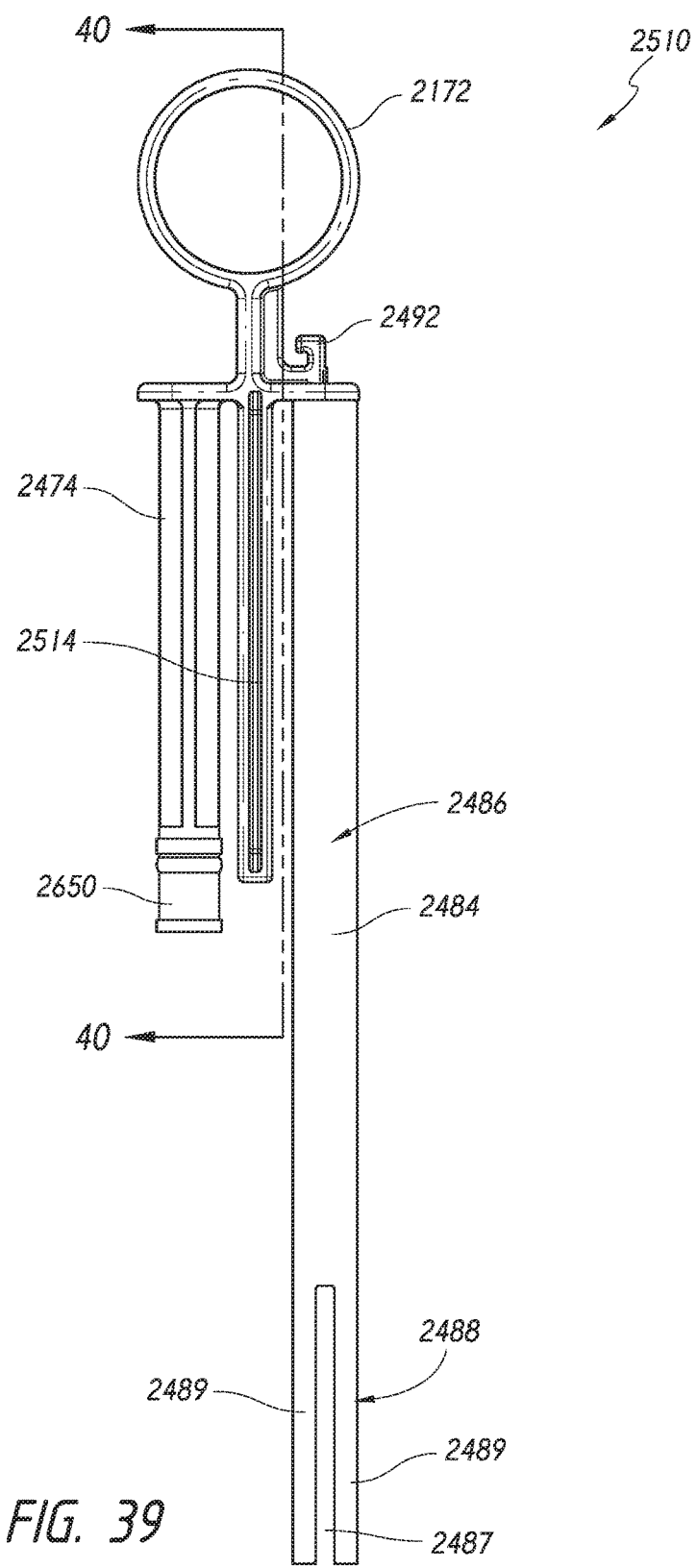
FIG. 39 illustrates a front view of a plunger assembly, according to some embodiments.
Figure 40:
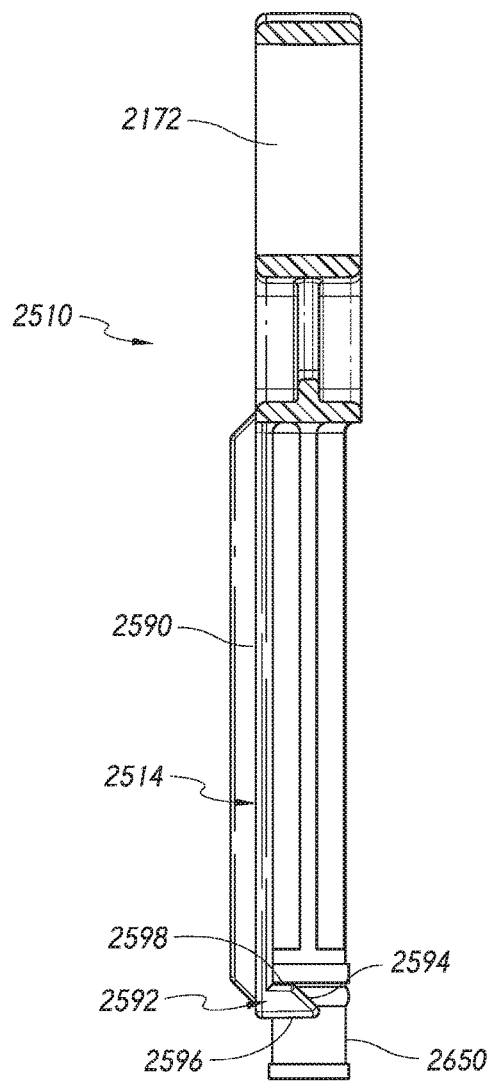
FIG. 40 illustrates a cross-sectional view of a plunger assembly, taken along the line 40-40 of FIG. 39.
Figure 41:
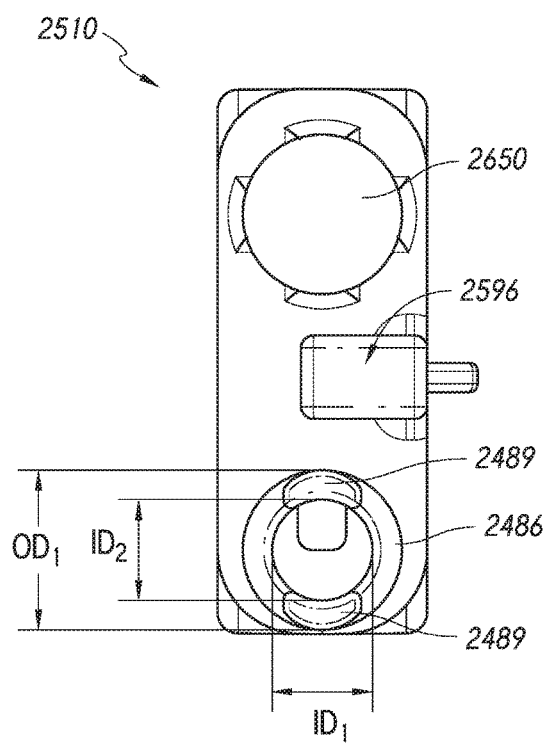
FIG. 41 illustrates a bottom view of the plunger assembly of FIG. 39.

FIGS. 39-41 illustrate one embodiment of a plunger assembly 2510 that can be used with a vascular access system 2140. FIG. 39 illustrates a front view, FIG. 40 illustrates a cross-sectional view taken along the line 40-40 of FIG. 39, and FIG. 41 illustrates a bottom view. The plunger assembly can include a first plunger 2474, a second plunger 2484, and a locking device 2514 preferably positioned between the plungers. The plunger assembly can include a handle 2172 configured to assist when moving the plunger. The handle 2172 can be formed according to any known handle design.

The first plunger 2474 can function similarly to other first plungers described herein. For example, in some embodiments it can include a plunger seal 2650 at its distal end configured to fluidly seal a portion of a reservoir expanded by withdrawal of the plunger.

Preferably, the second plunger 2484 includes at least a first portion 2486 that defines an interior chamber. The interior of the first portion 2486 can be configured to receive a biasing member, such as the retraction spring 2725 discussed above. In some embodiments, the plunger assembly 2510 can include a hook or other connecting portion 2492 that can be configured to receive one end of the spring 2725.

In some embodiments, the second plunger can include a second portion 2488 at a distal end thereof, which can be used to block passage of a piercing member holder as described above. The second portion can have at least two slots 2487 cut out of the plunger to define two or more prongs 2489. The prongs can have a first position as illustrated, in which the prongs define an inner diameter $ID_2$. In some embodiments, the inner diameter $ID_2$ is approximately equal to the inner diameter $ID_1$ of the first portion 2486. This can be seen in FIG. 41. In some embodiments, the inner diameter $ID_1$ can be greater than or less than to the inner diameter $ID_2$. In the first position, the prongs can also have an outer diameter $OD_1$.

Preferably, the prongs 2489 can be configured to flex radially inward. When the plunger assembly 2510 is in an initial position in which the piercing assembly is used to pierce a patient's skin, the second portion 2488 of the second plunger 2484 can be at least partially within the second section 2584 of the second barrel 2480. Preferably, the inner diameter $ID_3$ of the second section of the second barrel is less than the outer diameter $OD_1$ of the second portion 2488 of the second plunger. Thus, the walls of the second portion of the barrel will flex the prongs 2489 inward, shrinking the inner diameter of the prongs to a compressed inner diameter that is less than the inner diameter $ID_2$. The compressed inner diameter can also be less than an outer diameter $OD_2$ of a piercing member holder (e.g., as shown below in FIG. 42). This can block the piercing member holder from retracting, as described above.

In some embodiments, as illustrated in FIG. 40, the locking device 2514 can include a flexible lever arm 2590 that can have a proximal end that attaches to the plunger assembly 2510 and a movable distal end. The device can include a locking projection 2592 at the distal end. The locking projection can have a distal facing surface 2596 that can be configured to contact connecting sections, such as the second connecting section 2532, of the extraction assembly housing 2170. This can block distal motion of the locking device and therefore the plunger assembly 2510. Thus, the distal facing surface 2596 is preferably oriented such that when it contacts a connecting section the flexible lever arm remains generally in the position as illustrated, with its longitudinal axis generally parallel to a longitudinal axis of the first plunger 2474 and a longitudinal axis of the second plunger 2484. In some embodiments, the distal facing surface 2596 extends generally perpendicular to the longitudinal axis of the lever arm 2590.

In some embodiments, the locking projection 2592 can have a proximal facing surface 2594 that is angled relative to the longitudinal axis of the lever arm 2590. This surface can be used to cause the lever arm to flex upward to clear connecting sections of the extraction assembly housing 2170, allowing the plunger assembly 2510 to be withdrawn relative the extraction assembly housing. This is described in more detail below. The locking projection can also have a proximal facing surface 2598 that can extend generally perpendicular to the longitudinal axis of the lever arm 2590. This can be used to block withdrawal of the plunger assembly relative to the extraction assembly housing 2170, such as when the locking projection 2592 braces against connecting sections. This is also described in more detail below.

Figures 42, 43:
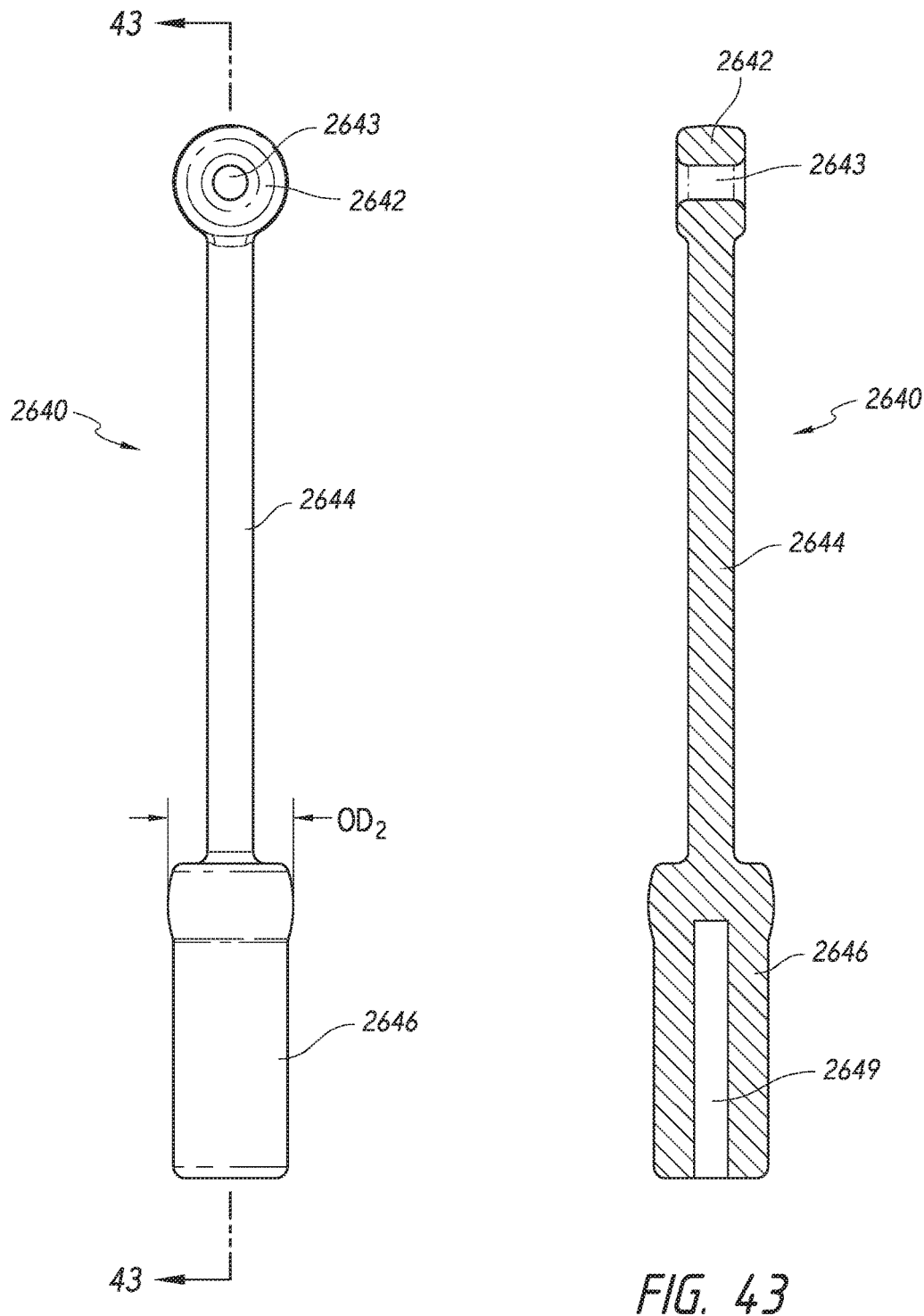
FIG. 42 illustrates a front view of a piercing member holder, according to some embodiments.
FIG. 43 illustrates a cross-sectional view of a piercing member holder, taken along the line 43-43 of FIG. 42.

FIGS. 42 and 43 illustrate one embodiment of a piercing member holder 2640 that can be used with a vascular access system 2140. FIG. 42 is a front view and FIG. 43 is a cross-sectional view taken along the line 43-43 of FIG. 42. Preferably, the piercing member holder includes a first section 2642 adapted to attach to a biasing member and a second section 2646 adapted to receive a piercing member. The first section can attach to the biasing member through any standard connection. For example, where the biasing member is a spring, the first section 2642 can include an aperture 2643 adapted to receive a hook member from the spring. Similarly, the second section can receive a piercing member through standard methods and/or apparatuses, such as by seating an end of a piercing member within a bore 2649. In some embodiments, the piercing member holder can also include an intermediate section 2644 between the first and second sections.

Preferably, a portion of the second section 2646 can have an outer diameter $OD_2$ that can fit within the second plunger 2484 of the plunger assembly 2510 to thereby allow the piercing member holder to be retracted into the plunger assembly. Thus, the outer diameter $OD_2$ is preferably less than the inner diameter $ID_2$ of the second portion 2488 of the second plunger. In some embodiments, the outer diameter $OD_2$ is also less than the inner diameter $ID_1$ of the first portion 2486 of the second plunger.

Preferably, however, the outer diameter $OD_2$ is greater than an inner diameter of the second portion 2488 of the second plunger 2484 when the second portion is biased inward by the second barrel 2480. As described above, this will inhibit or prevent the piercing member holder 2640 from retracting while the second portion 2488 of the second plunger is within the second section 2584 of the second barrel. The piercing member holder will not retract until the second portion of the second plunger exits the second section of the barrel, allowing the prongs 2489 to expand back toward the position illustrated in FIG. 39 in which they have an inner diameter $ID_2$ greater than the outer diameter $OD_2$.

Figure 44:
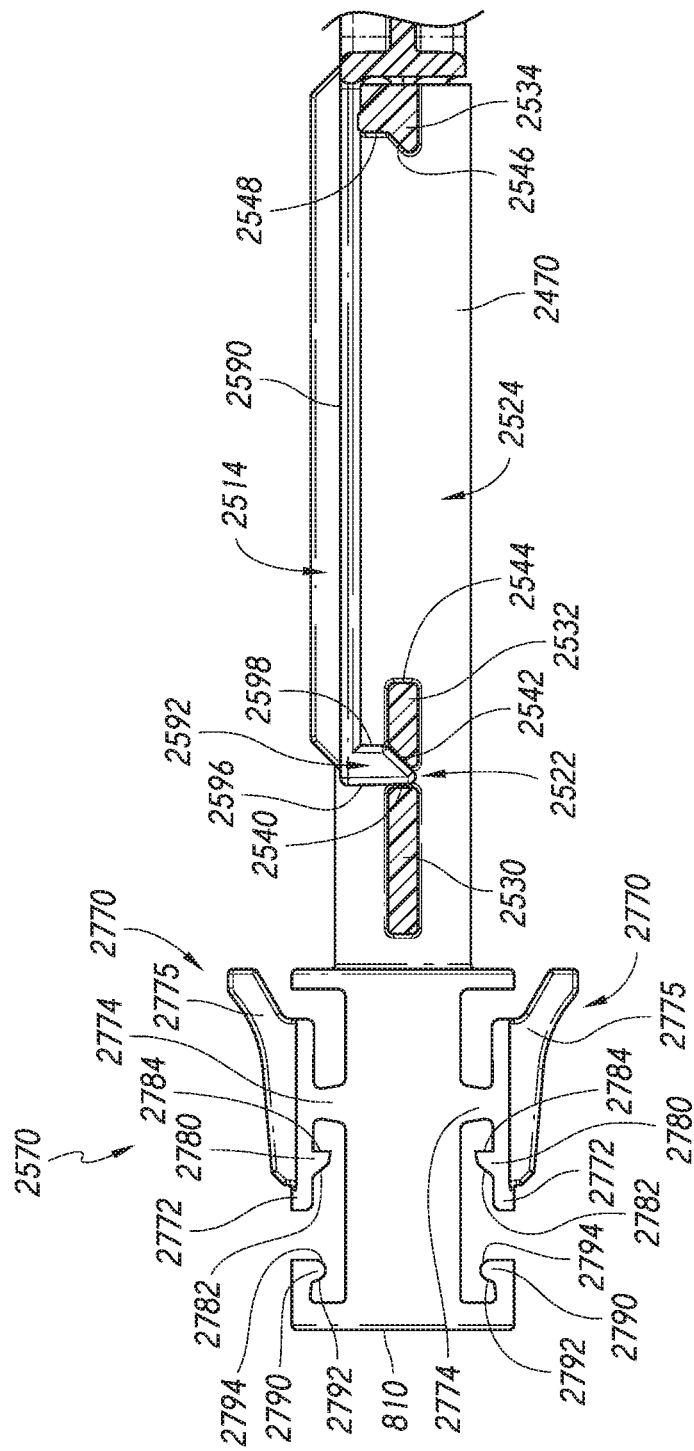
FIG. 44 illustrates a cross-sectional view of an extraction assembly housing, taken along the line 44-44 of FIG. 38, and including one embodiment of a locking device of a plunger assembly.

FIG. 44 illustrates a side cross-sectional view of the extraction assembly housing 2170 taken along the line 44-44 shown in FIG. 38. FIG. 44 also illustrates a cross-section view of a plunger assembly 2510 positioned in the housing. The plunger assembly preferably has an initial position in which the locking projection 2592 is positioned in a first locking channel 2522 between the first connecting section 2530 and the second connecting section 2532. In some embodiments, the first connecting section includes a proximal wall 2540 that aligns with the distal facing surface 2596 of the locking projection 2592 and inhibits or prevents further insertion or distal motion of the plunger assembly 2510. In some embodiments, the second connecting section 2532 can include an angled surface 2542 on its distal end that is configured to interact with the proximal facing surface 2594 of the projection 2592. The force of the angled surface 2542 on the surface 2594 can tend to push the projection upward, flexing the lever arm 2590. The projection can be moved far enough upward to clear the second connecting section 2532, allowing the plunger assembly 2510 to be drawn proximally past the second connecting section 2532.

When the locking projection 2592 passes a proximal wall 2544 of the second connecting section 2532, the lever arm 2590 will move back down and the locking projection will move into the second locking channel 2524 between the second connecting section 2532 and the third connecting section 2534. When the locking projection is within the second locking channel and the locking device 2514 is moved distally, the proximal wall 2544 can be configured to contact the distal facing surface 2596 of the locking projection 2592 to inhibit or prevent further distal motion of the plunger assembly 2510.

The locking projection and plunger assembly can preferably move freely within the second locking channel. When the plunger assembly is drawn proximally, the locking projection 2592 can reach the third connecting section 2534. The third connecting section can block the locking projection and inhibit or prevent the plunger assembly from being removed entirely from the extraction assembly housing 2170. In some embodiments, the third projection can have an angled portion 2546 and a portion 2548 that extends generally perpendicular to the longitudinal axis of the first barrel 2470. In some embodiments, the angled portion can be configured to align with the angled surface 2594 of the locking projection 2592. In some embodiments, the generally perpendicular portion 2548 can be configured to align with the surface 2598 of the locking projection.

In some embodiments, the positioning of the connecting sections of the extraction assembly housing 2170 can be configured to correspond to certain desired positions of the plunger assembly 2510 within the housing. For example, in some embodiments, when the locking projection 2592 is within the first locking channel 2522, the second plunger can be positioned as illustrated in FIG. 37, with a distal tip 2738 of the piercing member extending from the catheter 2164 and with the second portion 2488 of the second plunger blocking retraction of the piercing member holder 2640. In some embodiments, the second connecting section 2532 of the second plunger can be sized to reflect the distance that the plunger assembly can be withdrawn before the second portion 2488 of the second plunger 2484 exits the second section 2584 of the second barrel 2480, thereby allowing the retraction spring 2725 to retract the piercing member. In some embodiments, the second section 2532 can be sized such that the locking projection 2592 moves into the second channel 2524 at approximately the same time that the piercing member is retracted by the retracting spring.

Until the locking projection 2592 moves into the second channel 2524, however, the plunger assembly can be moved freely distally and proximally between the first channel 2522 and the second channel 2524. This can allow a clinician to withdraw the plunger assembly slightly to test for blood flow to ensure that the catheter is properly within a vein before the piercing member is retracted by the spring 2725. Once the locking projection moves into the second channel, the plunger assembly can move freely within the second channel. This can allow for withdrawal or insertion of the plunger as desired. Because the piercing member has already been retracted, the clinician does not need to be concerned about accidentally piercing the catheter.

FIG. 44 also illustrates a cross-sectional view of the connector holder 2570. The connector holder can include one or more first lock points 2790 and one or more second lock points 2780. As described above, the connector holder 2570 can be configured to connect to a medical connector, such as a needleless connector 2220. The medical connector can have a shoulder or circumferential projection, such as the projection 238 illustrated in FIG. 7 or the shoulder illustrated in FIGS. 10 and 11. When the medical connector is first inserted into an opening 810 in the connector holder 2570, the projection of the medical connector can contact a distal sloped or angled surface 2792 of the first lock points. The lock points can be flexed outward, allowing the shoulder to pass to a position between the first and second lock points. This position is the first locked position, in which the seal in the needless connector (e.g., the second seal 280 visible in FIG. 7) preferably remains in a closed position.

When a clinician is ready to use the vascular access system to insert a catheter, the medical connector 2220 can be inserted further into the connector holder 2570. The projection 238 of the connector can contact a distal, angled surface 2782 of the second lock points 2784. Pushing the medical connector further preferably causes the second lock points 2784 to flex away, allowing the projection to pass them and into a second locked position in which the second seal of the connector 2220 is opened. Once the projection on the medical connector has passed the second lock points, they can return to their initial positions. A proximal surface 2784 of the second lock points 2784 that is generally perpendicular to a longitudinal axis of the connector holder can inhibit or prevent withdrawal of the medical connector.

In some embodiments, the second lock points 2780 can each be part of a clip 2770. The lock points can extend from a base 2772 of the clip. The clip can include grips 2775 that can be attached to the base or formed integrally with the base. Pinching the grips 2775 can cause a flexible neck 2774 of the clip to bend, angling such that opposing second lock points 2780 move apart from each other. This can create space for the projection 238 on a medical connector to pass, allowing the connector to be returned to the first locked position. If the medical connector is pulled more distally, the projection 238 will contact a proximal sloped or angled surface 2794 of the first lock points 2790, thereby forcing the first lock points away from each other and allowing for complete withdrawal of the connector.

FIGS. 45-59 illustrate one embodiment of a method of using a vascular access system 2140. FIGS. 45-59 also illustrate one embodiment of a vascular access system where withdrawal of a piercing member is decoupled from initial movement of a plunger assembly 2510. Thus, in some embodiments, a plunger assembly 2510 can be partially withdrawn to draw blood to confirm proper placement of the catheter without affecting the position of the piercing member relative to the catheter. This can help inhibit or prevent accidental piercing of the catheter with the piercing member when confirming blood flow and before completely withdrawing the piercing member. In FIGS. 45-59, elements labeled with numbers similar to numbers from previous embodiments are understood to function as previously described unless indicated otherwise.

Figure 45:
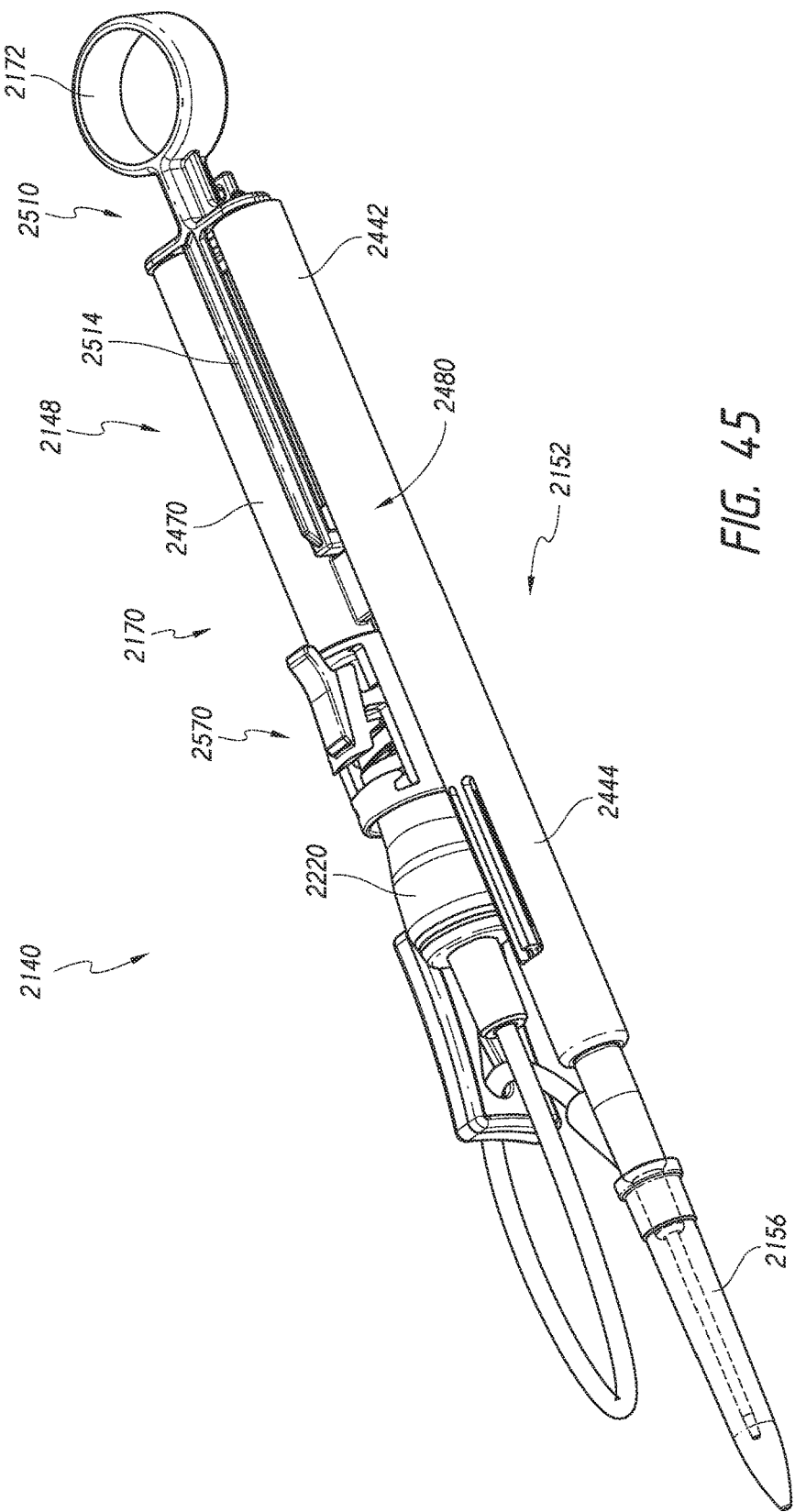
FIG. 45 illustrates a perspective view of a vascular access system, according to some embodiments.

FIG. 45 illustrates the vascular access system 2140 as preferably assembled for storage, such as when within any packaging. A cap 2156 preferably protects a piercing member. Preferably, when removed from a package or from storage the medical connector 2220 is in a first locked position within the connector holder 2570. In some embodiments, the medical connector can be separate from the connector holder when stored or when in packaging and it can be placed into the first locked position by a clinician or other individual after being removed for use.

FIG. 45 also illustrates an embodiment in which the second barrel 2480 includes a locking section 2444 that can be used to lock a piercing member holder and/or piercing member into an initial position while the plunger assembly 2510 is withdrawn from the extraction assembly housing 2170. This is described in more detail below.

Figure 46:
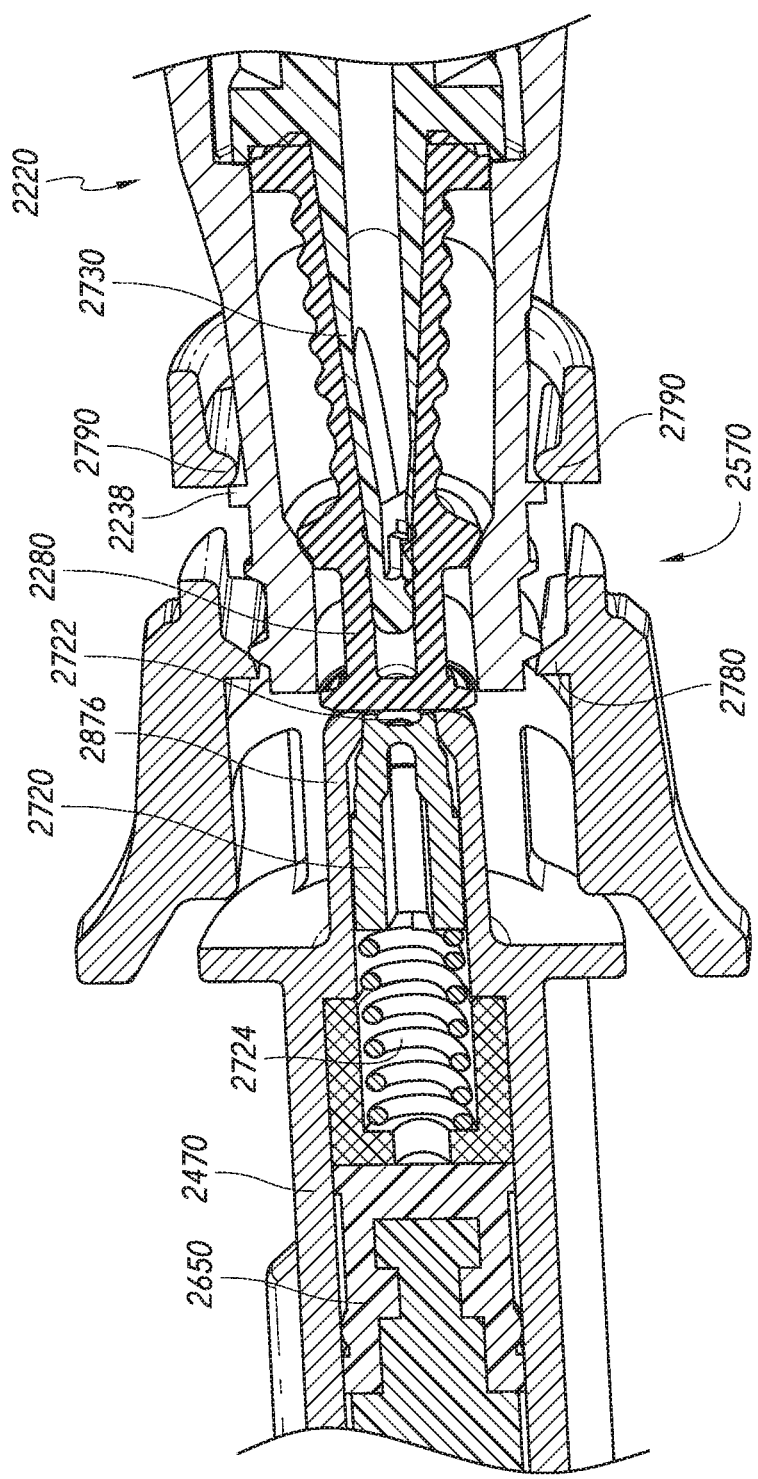
FIG. 46 illustrates a cross-sectional view of a portion of the vascular access system of FIG. 45.

FIG. 46 illustrates a cross section of the medical connector 2220 and connector holder 2570. In some embodiments, as described above, in the first locked position the medical connector has been inserted into the connector holder until a projection, such as the circumferential projection 2238, is between one or more first lock points 2790 and one or more second lock points 2780. Preferably, in the first locked position the second seal 2280 of the medical connector can be in a closed position, as illustrated.

When the medical connector 2220 is advanced further into the connector holder 2570 and toward a second locked position, a proximal protrusion 2730 of the connector can cause the third seal 2720 to move distally, as described above, thereby opening the third seal and fluid access to the barrel 2470. In some embodiments, the third seal 2720 can include a distal recess 2722 that can be configured to receive a tip of the proximal protrusion 2730. This can help ensure alignment between the third seal and the proximal protrusion. In some embodiments, while the medical connector is advanced a third section 2876 of the first barrel can be inserted into the connector and cause the second seal 2280 to move distally, also described above, thereby opening fluid communication through the medical connector 2220.

Figure 47:
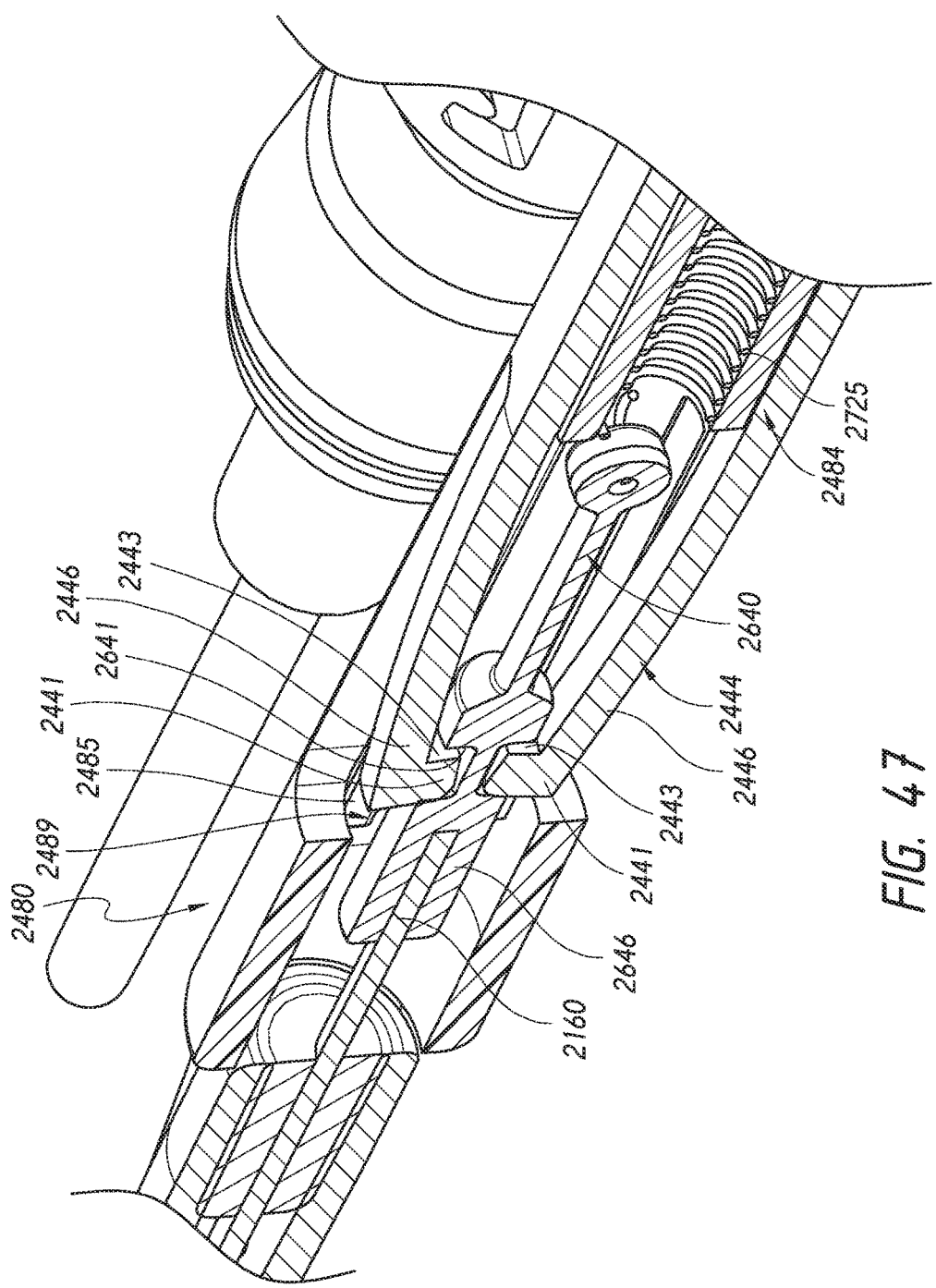
FIG. 47 illustrates a cross-sectional view of a portion of the vascular access system of FIG. 45.

FIG. 47 illustrates a cross section of a distal end of the second barrel 2480, including the locking section 2444. In some embodiments, the locking section can include one or more locking arms 2446 that are preferably biased toward an unlocked position in which they are generally parallel to a longitudinal axis of the second barrel. Preferably, the locking arms can be flexed radially inward into a locked position, as illustrated.

Figure 64:
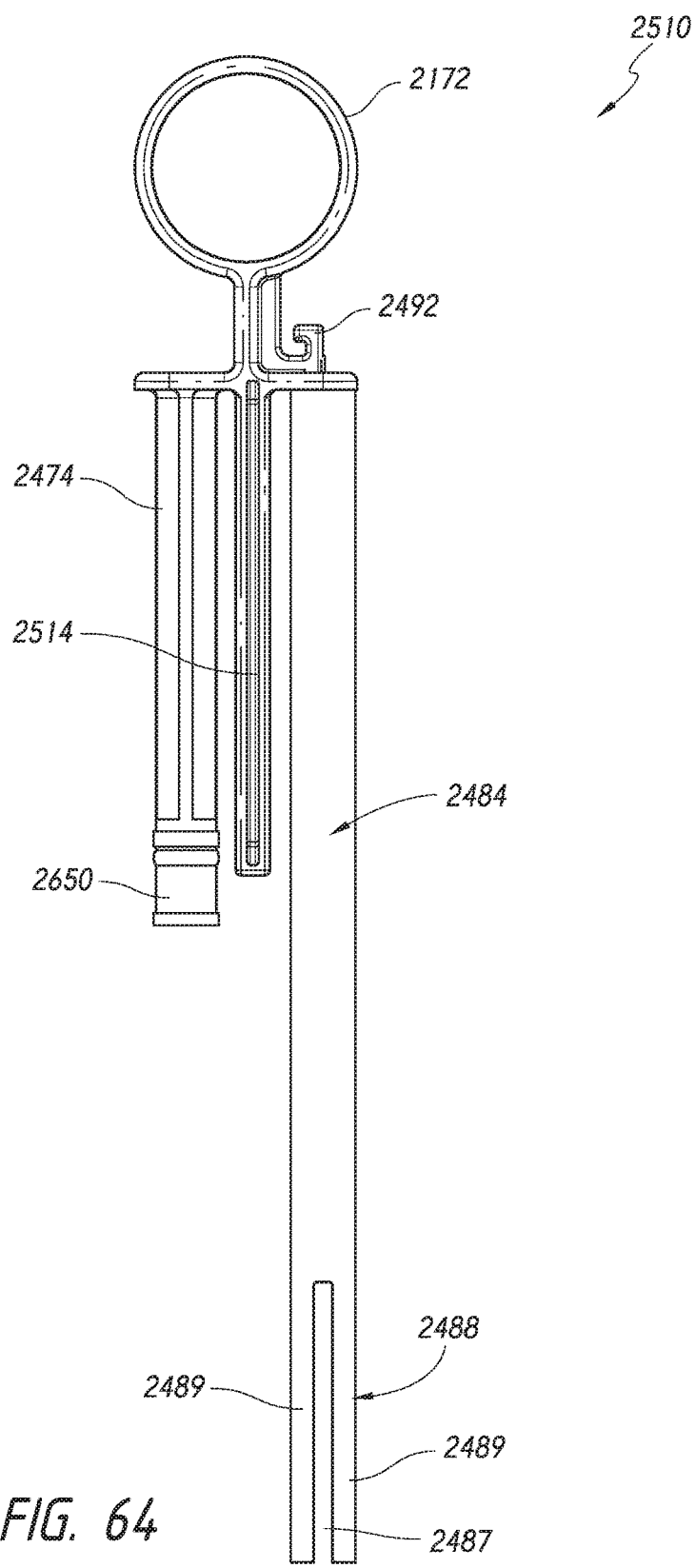
FIG. 64 illustrates a front view of a plunger assembly, according to some embodiments.
Figure 65:
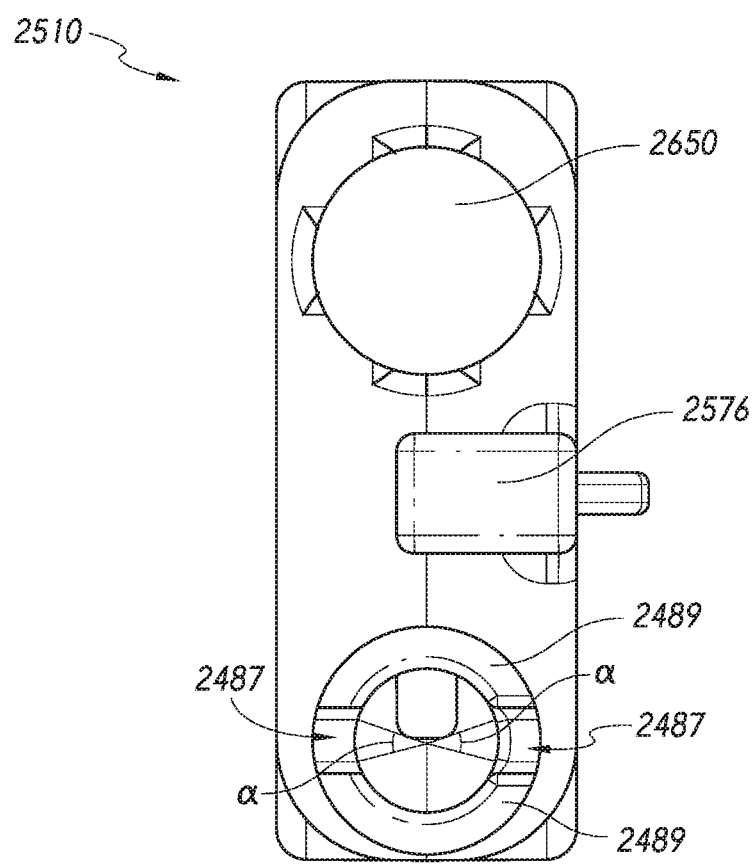
FIG. 65 illustrates a bottom view of the plunger assembly of FIG. 64.

In some embodiments, the locking arms 2446 can each include a radial projection 2441 and one or more circumferential projections 2443 extending from the radial projection. In the locked position, the radial projections and at least a portion of the locking arms 2446 can extend into or through a slot 2487 (for example, as shown in FIGS. 64 and 65) between prongs 2489 of the second plunger 2484. The circumferential projections 2443 can extend beneath a lip 2485 of a prong 2489 such that the prong inhibits or prevents the locking arms 2446 from returning to the unlocked position, while still allowing axial movement between the prongs 2489 and locking arms 2446. Preferably, the second plunger 2484 has two prongs 2489 and each radial projection 2441 has two circumferential projections 2443, one extending beneath a lip of each prong. This can be seen, for example, in FIGS. 60 and 61 described below. In some embodiments, one or more of the radial projections may have just one circumferential projection.

In some embodiments, the piercing member holder 2640 can include one or more cutouts 2641 configured to receive the radial projections 2441 and/or the circumferential projections 2443. In some embodiments, as illustrated for example in FIGS. 62 and 63 below, the piercing member holder 2640 can include a single circumferential cutout 2641 that can receive the radial projections 2441 and/or the circumferential projections 2443. Having cutouts that receive the radial projections 2441 and/or the circumferential projections 2443 can lock the position of the piercing member relative to the second barrel 2480 while the locking arms 2446 are in the locked position. Thus, in such embodiments the second plunger 2484 can be withdrawn without moving the piercing member holder 2640 or the piercing member 2160. In some embodiments, withdrawing the second plunger while the locking arms are in the locked position can increase the tension in the retraction spring 2725. When the second plunger is withdrawn completely past the circumferential projections 2443, the prongs 2489 will no longer retain the locking arms 2446 in a locked position and the locking arms can return to an unlocked position. When the locking arms return to the unlocked position, the radial projections and/or the circumferential projections can exit the cutouts 2641 of the piercing member holder. This will free the piercing member holder 2640, allowing the retraction spring 2725 to retract the piercing member holder and the piercing member.

Figure 48:
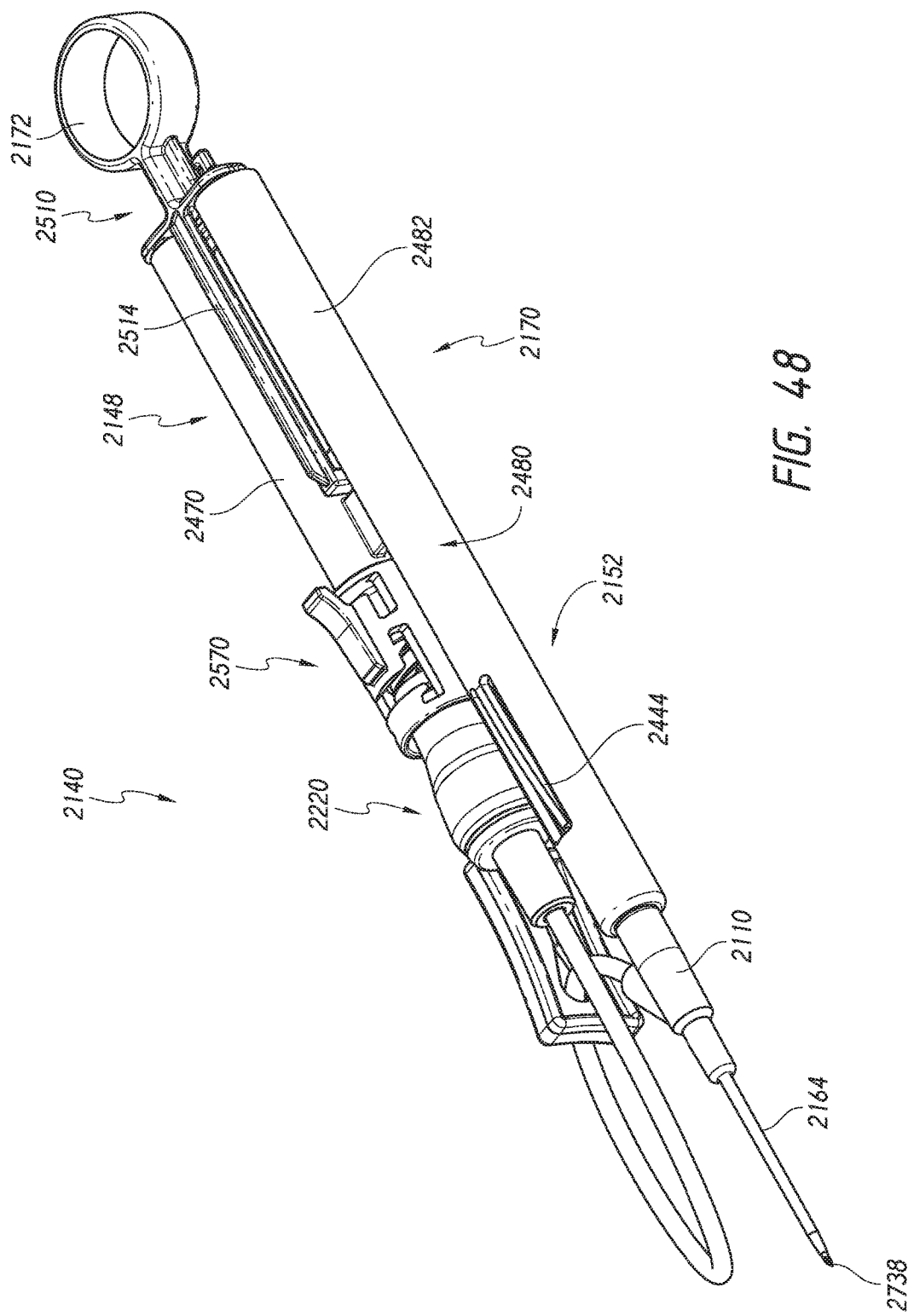
FIG. 48 illustrates the vascular access system of FIG. 45 with a cap removed.

With reference to FIG. 48, once the vascular access system 2140 has been removed from any packaging and/or storage, the cap 2156 can be removed. Preferably, the plunger assembly 2510 is completely inserted into the extraction assembly housing 2170 and a distal tip 2738 of a piercing member extends from the catheter 2164. In some embodiments, the plunger assembly may need to be inserted further into the extraction assembly housing 2170 for the distal tip to extend from the catheter. In some embodiments, the distal tip extends from the catheter when the plunger assembly has not been fully inserted.

Figure 49:
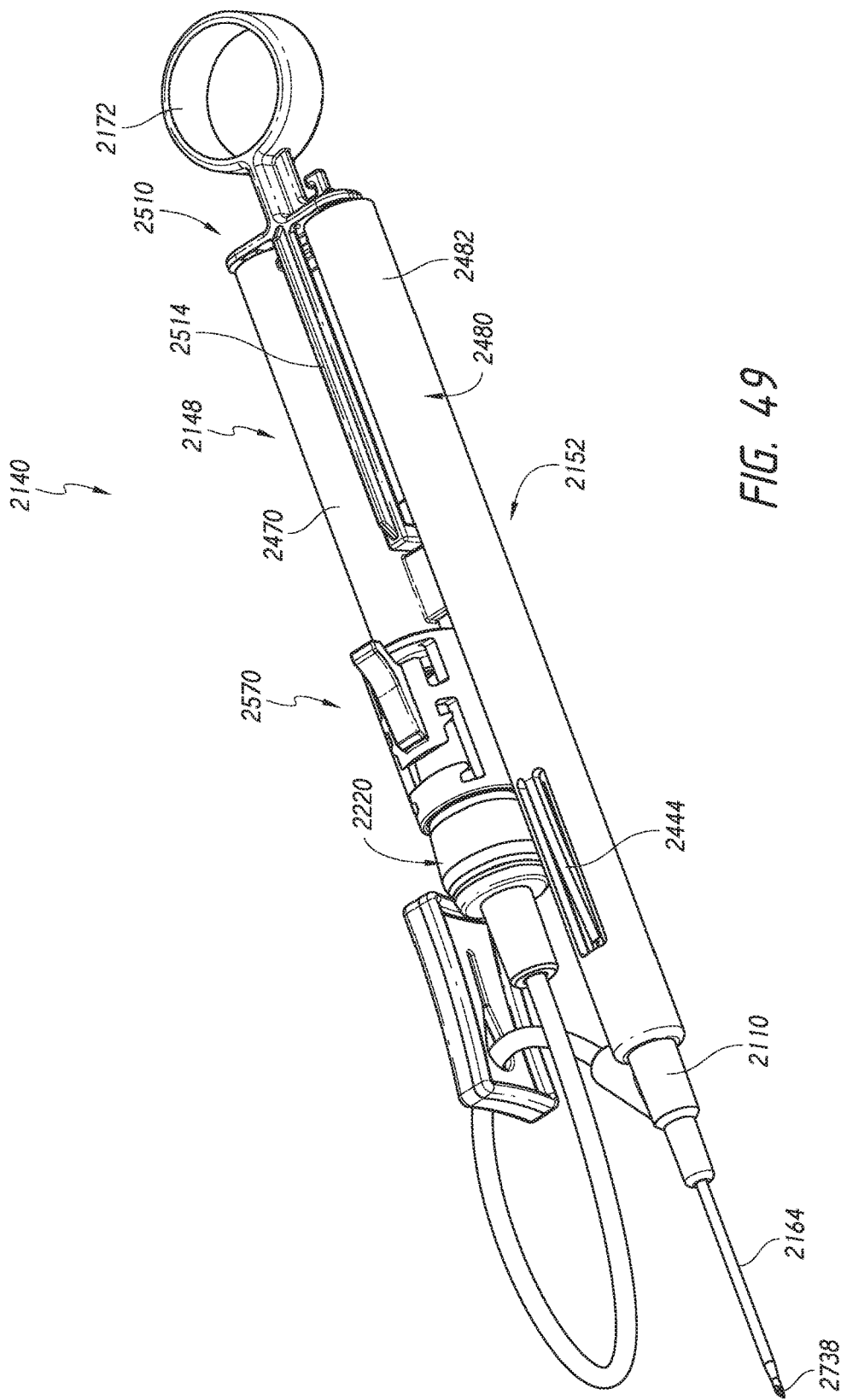
FIG. 49 illustrates the vascular access system of FIG. 48 with a medical connector moved to a second locked position.

In some embodiments, the medical connector 2220 can be moved into the second locked position within the medical connector holder 2570, as illustrated in FIG. 49, prior to inserting the piercing member and catheter into a patient. In some embodiments, the medical connector can be moved into the second position after inserting the piercing member and catheter into a patient.

Figure 50:
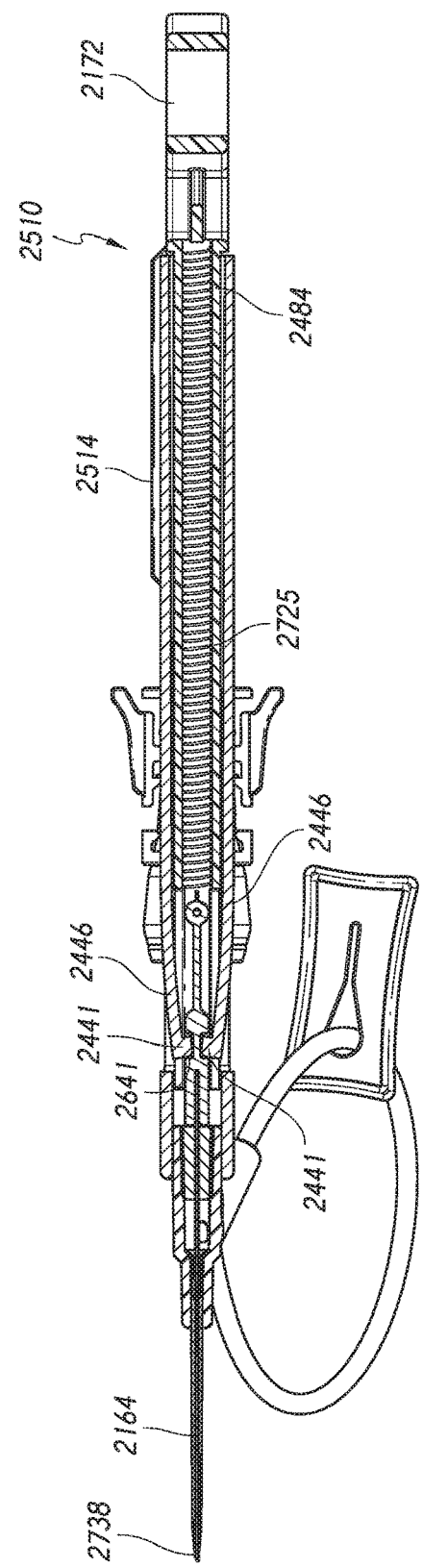
FIG. 50 illustrates a side cross-sectional view of the vascular access system of FIG. 49.

Once the piercing member and catheter have been inserted into a patient, it can be desirable to seek confirmation that the piercing member and catheter are properly positioned within a blood vessel of the patient. Thus, the plunger assembly 2510 can be partially withdrawn to create a negative pressure in the first barrel and to draw blood into the piercing member and catheter, as illustrated in FIG. 50. In some embodiments, a piercing member can be configured according to the embodiments discussed with reference to FIG. 27, and blood that reaches the opening 743 of the piercing member can be visible through the catheter. In some embodiments, other forms of confirmation can be used, such as seeing blood within the housing 2110.

Also, as described above, in some embodiments withdrawing the plunger assembly can cause a locking projection 2592 of a locking device 2514 to ride up onto a second connecting section 2532 of the extraction assembly housing 2170. Preferably, the second connecting section 2532 can be sized such that the locking arms 2446 remain in the locked position while the locking projection remains on the second connecting section. Preferably, when the plunger assembly 2510 is withdrawn far enough for the locking projection to move into the second channel 2524 of the extraction assembly housing, the second plunger 2484 will be withdrawn far enough for the locking arms 2446 to return to an unlocked position. In some embodiments, the locking arms can return to an unlocked position while the locking projection is on the second connecting section. In some embodiments, the lock arms can return to an unlocked position after the locking projection has moved into the second channel.

In some embodiments, the vascular access system 2140 can be configured such that the locking arms 2446 return to an unlocked position after the plunger assembly 2510 has been withdrawn far enough to draw a defined volume of blood into the system through the piercing member. In some embodiments, the piercing member 2160 may not retract until the defined volume of blood has been drawn into the system. In some embodiments, the defined volume of blood can be an amount required to provide confirmation that the piercing member has been properly positioned within a blood vessel of the patient. In some embodiments, the defined volume of blood can be an amount required to pass through the catheter and into the needleless connector 2220. In some embodiments, the defined volume of blood can be an amount required to prime the connector. In some embodiments, the defined volume of blood can be greater than or equal to about 1 cubic centimeter. In some embodiments, the defined volume of blood can be greater than or equal to about 3 cubic centimeters. In some embodiments, the defined volume of blood can be greater than or equal to about 7 cubic centimeters. In some embodiments, the defined volume of blood can be greater than or equal to about 15 cubic centimeters.

Figure 51:
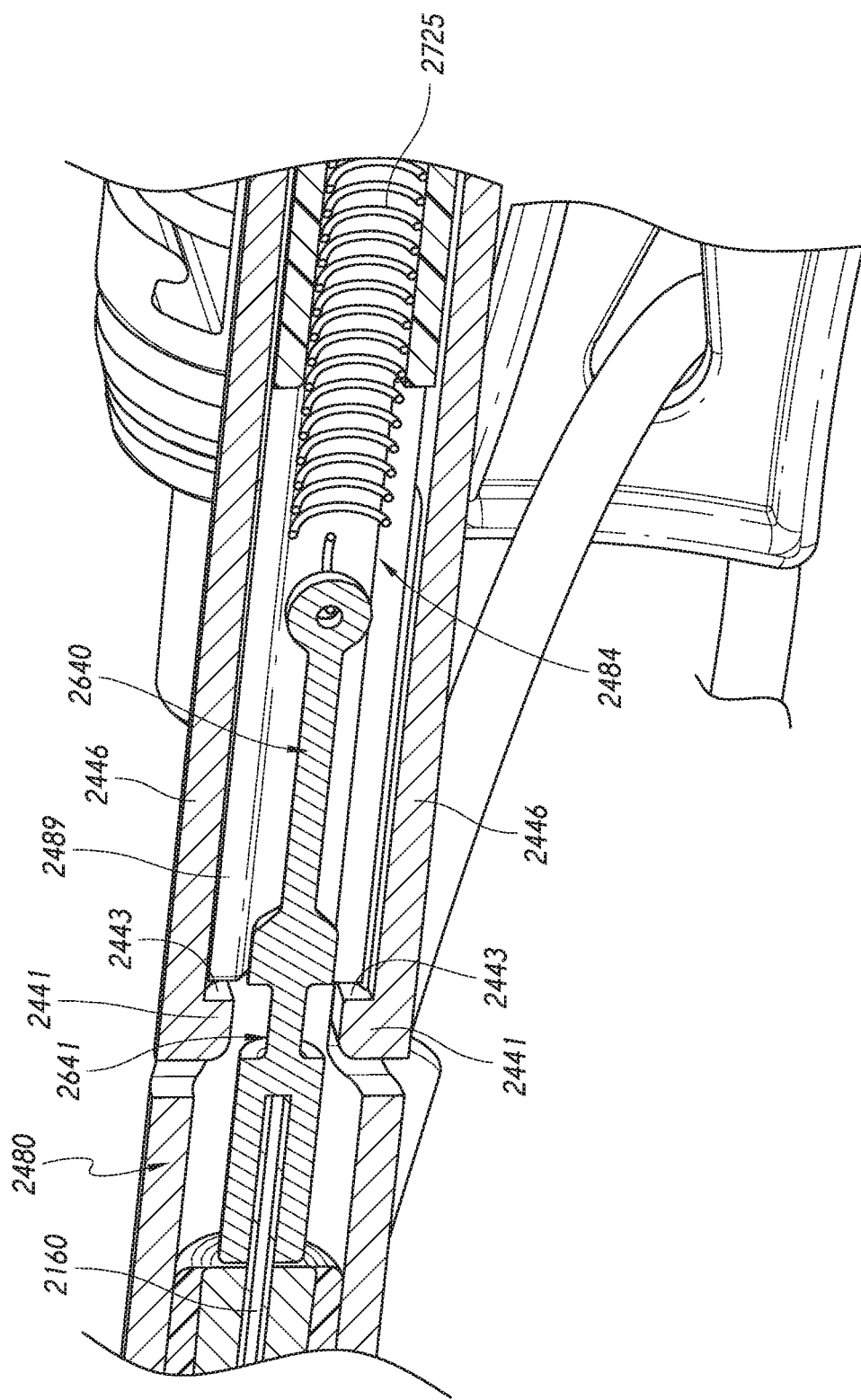
FIG. 51 illustrates a cross-sectional view of the vascular access system of FIG. 50 with locking arms in an unlocked position.
Figure 52:
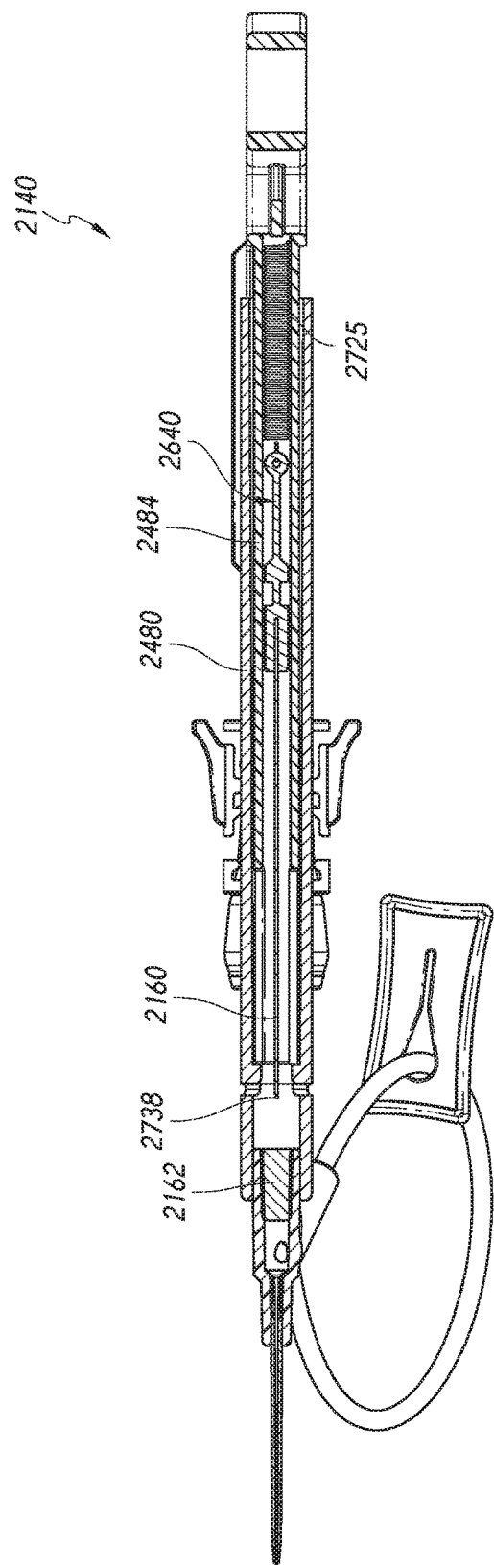
FIG. 52 illustrates a cross-sectional view of the vascular access system of FIG. 51 with a piercing member holder retracted.

FIG. 51 illustrates second barrel 2480 and second plunger 2484 when the second plunger has been withdrawn far enough for the locking arms 2446 to move to the unlocked position. As illustrated, the radial projections 2441 can move away from the cutouts 2641 (or from a single, circumferential cutout), allowing the piercing member holder 2640 to move relative to the second barrel and allowing the retraction spring 2725 to withdraw the piercing member holder. FIG. 52 illustrates the vascular access system 2140 once the piercing member holder and piercing member 2160 have been withdrawn. As illustrated, once withdrawn, the piercing member is preferably entirely within the second barrel 2480 such that accidental sticks of the distal tip 2738 can be inhibited or prevented.

With further reference to FIG. 51, in some embodiments the circumferential projections 2443 of the locking arms 2446 can block distal movement of the second plunger 2484 when the locking arms are in the unlocked position. This can help inhibit or prevent further insertion of the second plunger, which could re-expose the piercing member and risk accidental sticks. When a vascular access system 2140 is first assembled, the locking arms can be manually moved into the locked position in order to insert the second plunger past the circumferential projections 2443. The second plunger would then retain the locking arms in the locked position, as described above. Preferably, when first assembling the access system, the locking arms are moved into the locked position before the spring 2725 is tensioned, such as by pulling it and attaching it to the connecting portion 2492 (illustrated in FIG. 39).

Figure 53:
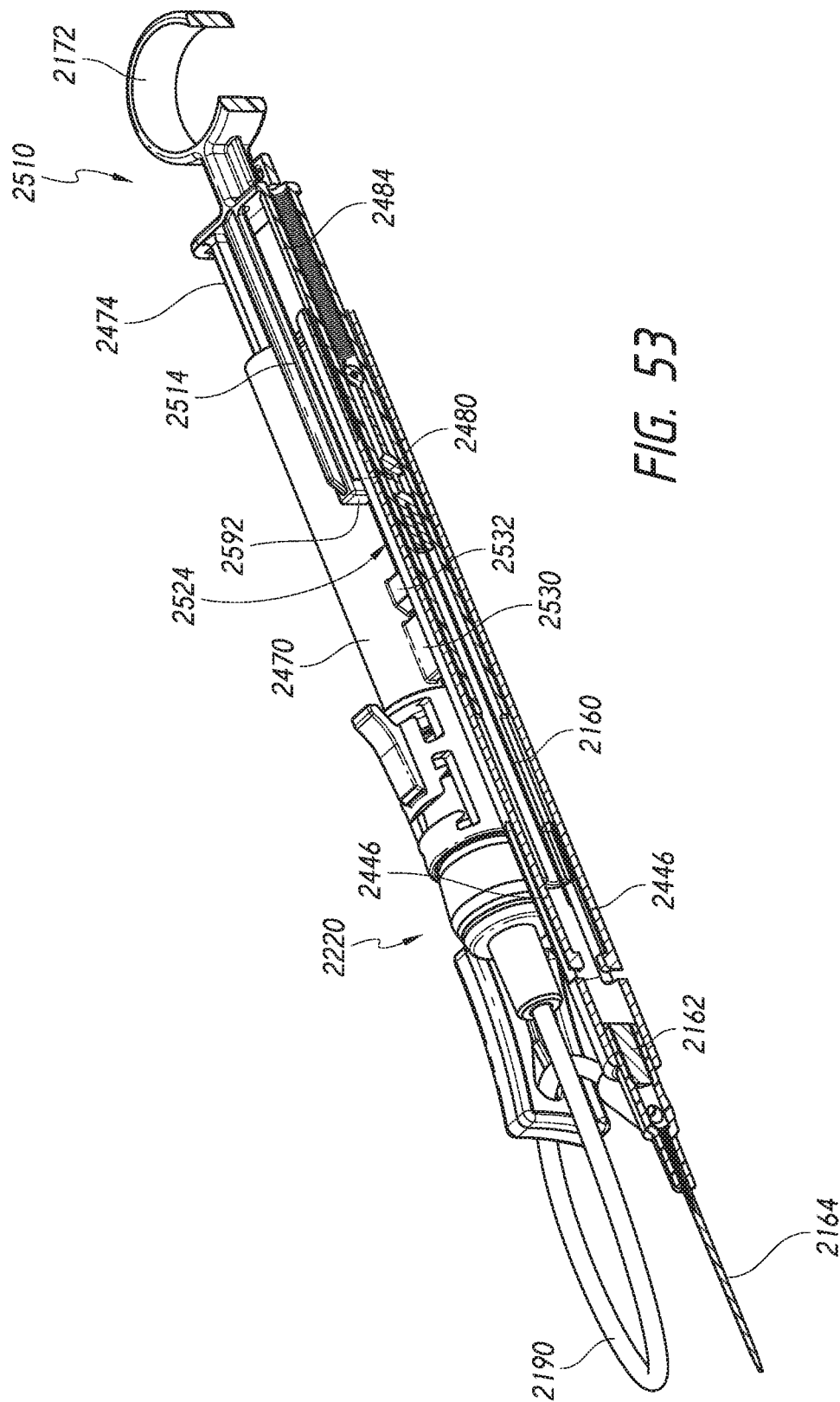
FIG. 53 illustrates a perspective cross-sectional view of the vascular access system of FIG. 52 with a plunger assembly partially withdrawn.

Once the plunger assembly 2510 has been withdrawn far enough to allow the piercing member 2160 to retract, the plunger assembly can be withdrawn further to create more negative pressure in the first barrel 2470. This can draw blood through the catheter 2164 and into the connector 2220 to ensure that the connector is primed. FIG. 53 illustrates a vascular access system as the plunger assembly is withdrawn to prime the connector. As illustrated, the locking projection 2592 is preferably within the second channel 2524. When the locking projection is within the second channel the plunger assembly can be freely withdrawn without needing the locking projection to pass over any section connecting the first barrel 2470 and second barrel 2480. This free motion requires less force than would be required to pull the locking projection over connecting sections and can also inhibit or prevent vibrations. This can make it less likely that a clinician will accidentally slip or move the catheter when priming the connector.

Figure 54:
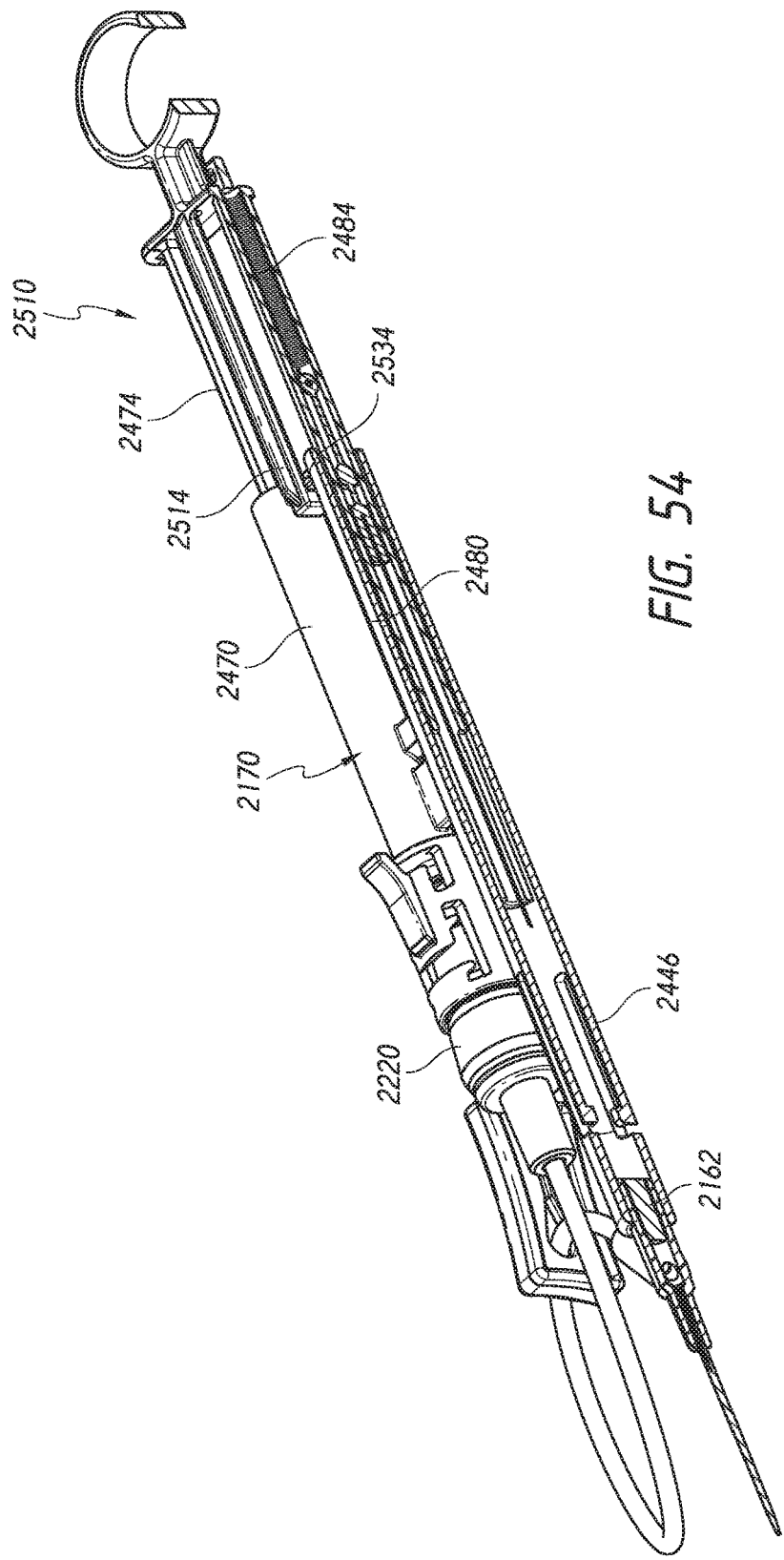
FIG. 54 illustrates a perspective cross-sectional view of the vascular access system of FIG. 53 with the plunger assembly further withdrawn.
Figure 55:
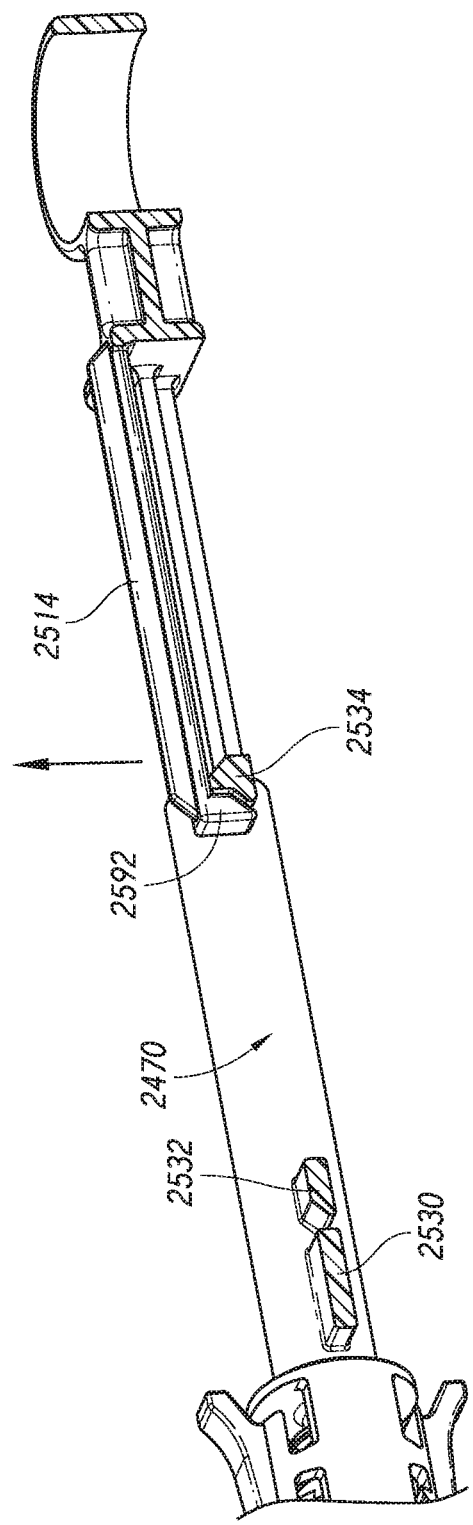
FIG. 55 illustrates a detailed view of a locking device of the vascular access system of FIG. 54.
Figure 56:
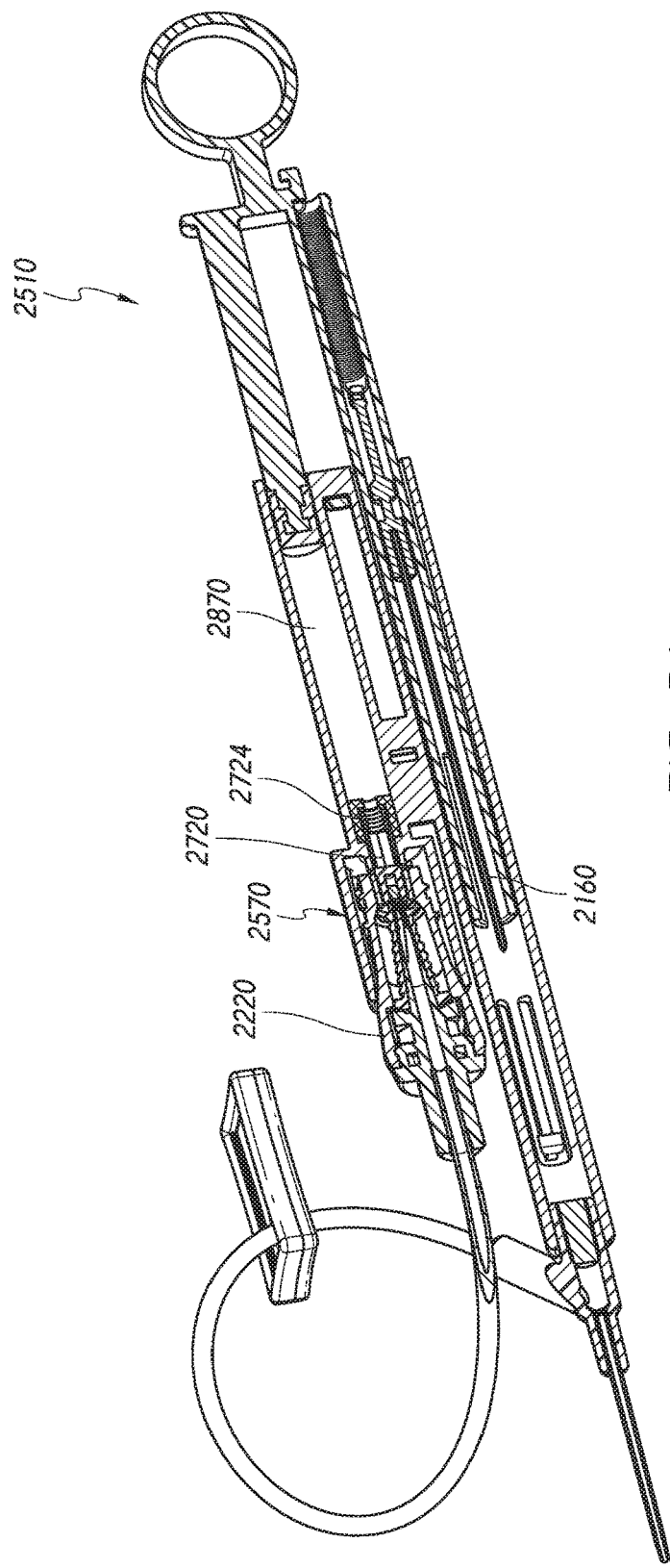
FIG. 56 illustrates a perspective cross-sectional view of the vascular access system of FIG. 55.

FIGS. 54-56 illustrate the plunger assembly 2510 when it has been withdrawn to a maximum position. In some embodiments, withdrawing the plunger assembly to the maximum position draws enough blood such that blood passes through the connector 220 and into an inner chamber 2870 of the first barrel 2470. Preferably, the first barrel 2470 is translucent or clear such that a clinician can see blood within the inner chamber 2870 to confirm that the medical connector has been fully primed.

Preferably, the plunger assembly 2510 in the maximum position is still at least partially within the extraction assembly housing 2170. This can ensure that any blood drawn into the first barrel 2470 is not able to spill out the proximal end of the barrel. It can also ensure that the piercing member remains protected by the second barrel 2480. In some embodiments, as described above and as illustrated in FIG. 55, a third connecting section 2534 can interact with the locking projection 2592 to inhibit or prevent withdrawal of the plunger assembly beyond the maximum withdrawal position.

Figure 57:
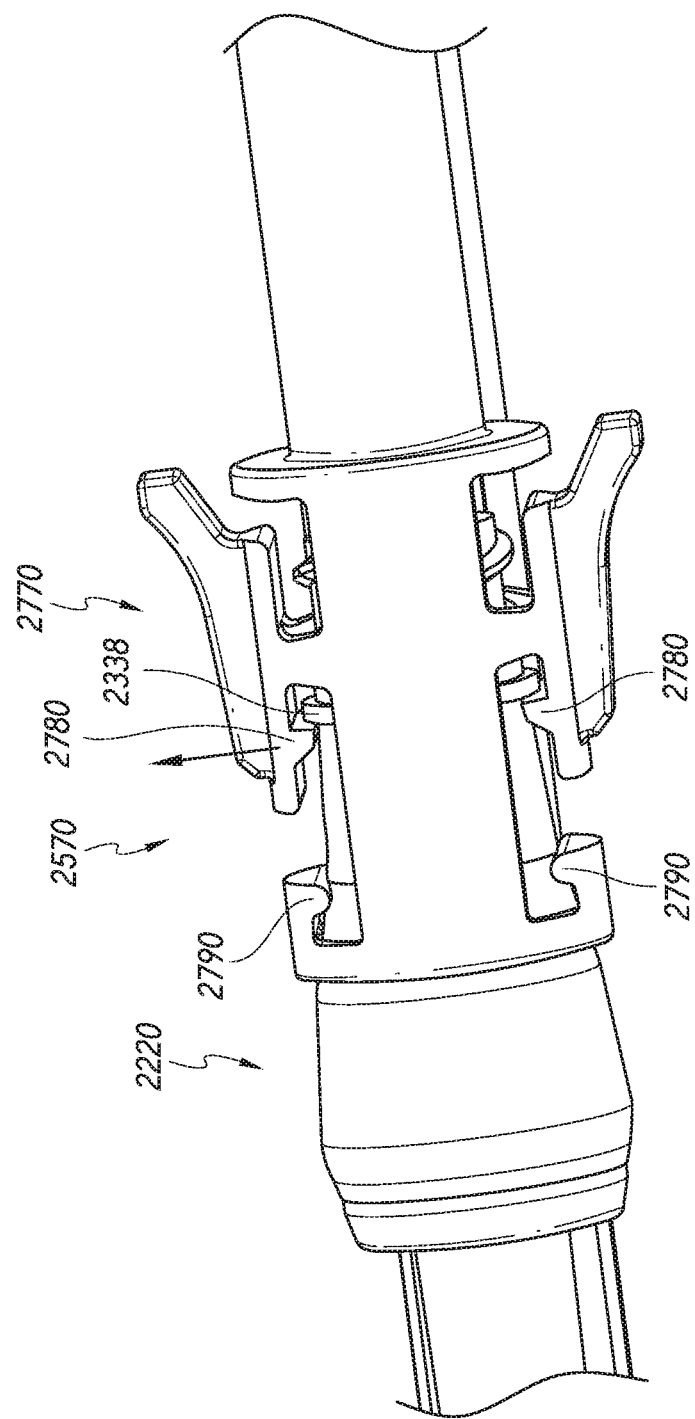
FIG. 57 illustrates a view a medical connector in a second locked position.
Figure 58:
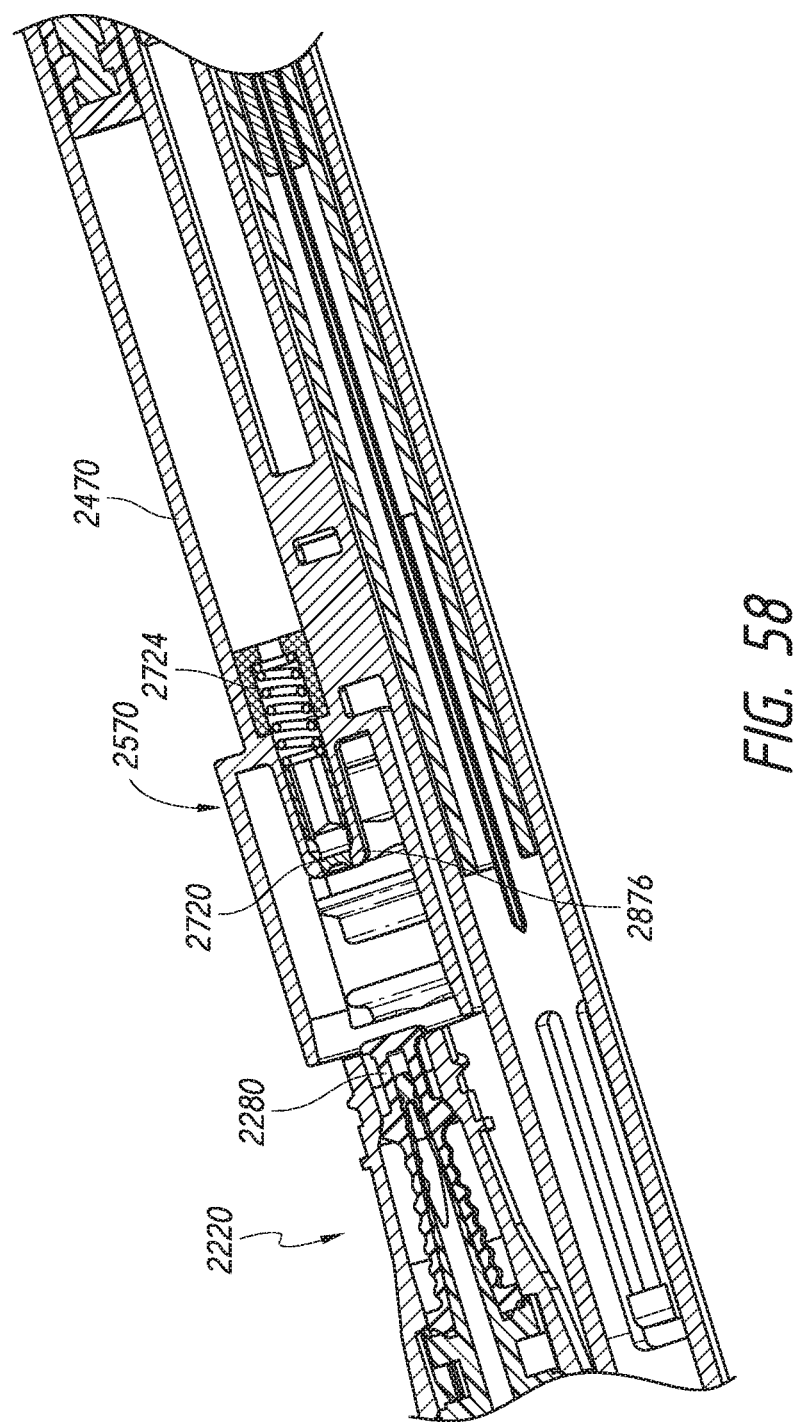
FIG. 58 illustrates a view of the medical connector of FIG. 57 removed from a connector holder.

With reference to FIGS. 57 and 58, once the plunger assembly 2510 has been withdrawn to retract the piercing member 2160 and the medical connector 2220 has been confirmed to be primed, the medical connector 2220 can be removed from the connector holder 2570. FIG. 57 illustrates the medical connector in the second locked position. The clips 2770 can be pinched, squeezed, or otherwise acted upon to separate opposing lock points 2780 from each other, allowing the circumferential projection 2238 to clear the second lock points and the medical connector to move to the first locked position. From the first locked position, the medical connector can be further withdrawn, the circumferential projection acting on the first lock points 2790 to separate them and allowing the medical connector to pass through, as described above.

When the medical connector is withdrawn from the connector holder, as shown in FIG. 58, the spring 2724 can bias the third seal 2720 back into the third section 2876 of the first barrel 2470. The third seal can seat in the third section to create a seal that prevents or substantially prevents fluid within the first barrel from moving past the third seal. Also, the second seal 2280 within the medical connector 2220 can return to a closed position, inhibiting or preventing fluid from passing through the medical connector.

Figure 59:
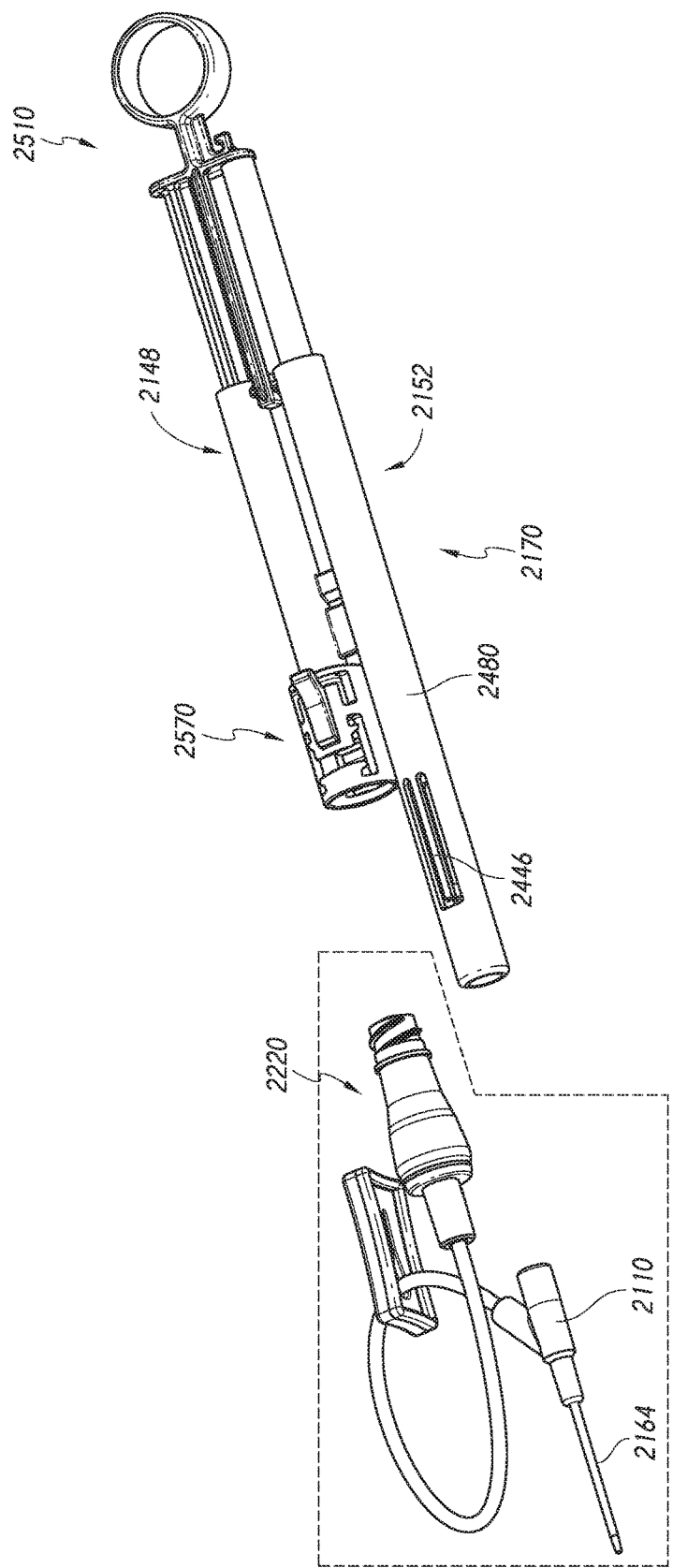
FIG. 59 illustrates a perspective view of an extraction assembly housing removed from a medical connector and housing.

As illustrated in FIG. 59, in addition to removing the medical connector 2220 from the connector holder 2570, the second barrel 2480 can be removed from the housing 2110. The extraction assembly housing 2170 and plunger assembly 2510 can be discarded and the medical connector 2220 and housing 2110 can be used to access the patient as desired.

Figure 60:
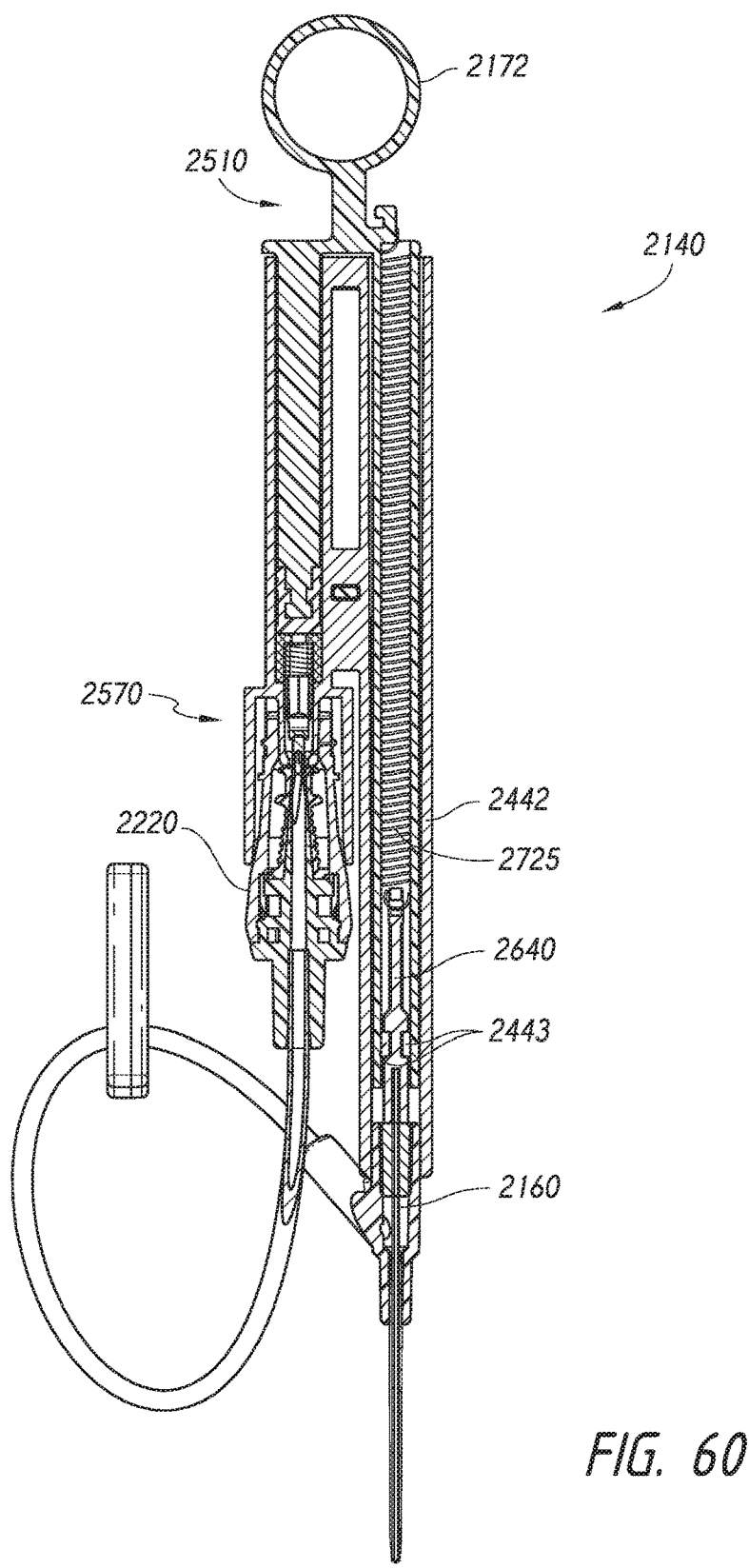
FIG. 60 illustrates a cross-sectional view of a vascular access system, according to some embodiments.
Figure 61:
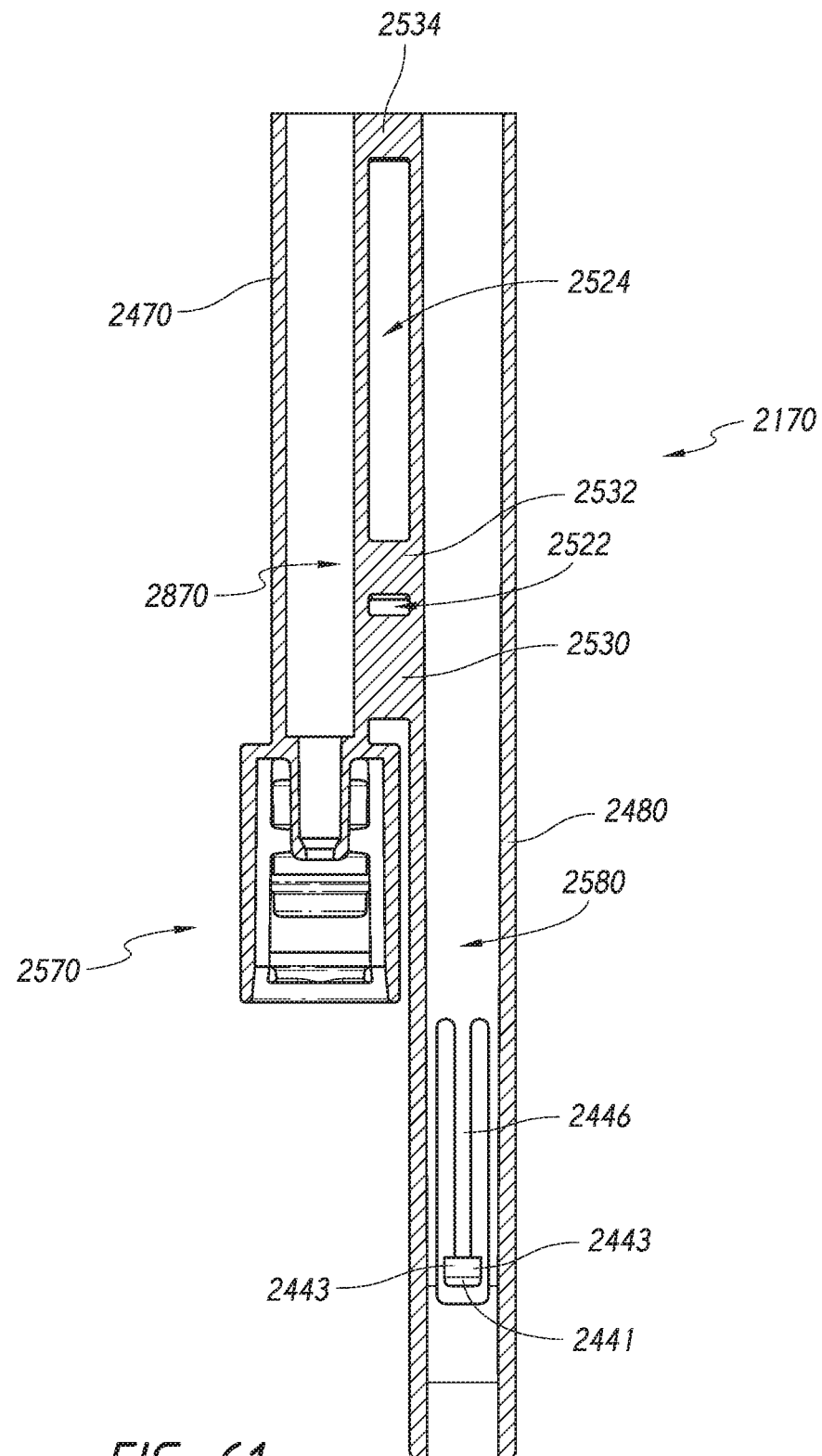
FIG. 61 illustrates a cross-sectional view of an extraction assembly housing, according to some embodiments.

FIGS. 60 through 65 illustrate various aspects of the vascular access system 2140 used in the method described with respect to FIGS. 45-59. FIG. 60 is a cross-sectional view of the access system 2140 when a medical connector 2220 has been advanced into a second locked position within a connector holder 2570. FIG. 61 is a cross-sectional view of an extraction assembly housing 2170. FIGS. 60 and 61 illustrate an example of an embodiment in which the locking arms 2446 of the housing 2170 include multiple radial projections 2443. In some embodiments, as further illustrated by example in FIGS. 60 and 61, the inner chamber 2580 of the second barrel 2480 can have a generally constant inner diameter, excluding the radial projections 2441.

Figures 62, 63:
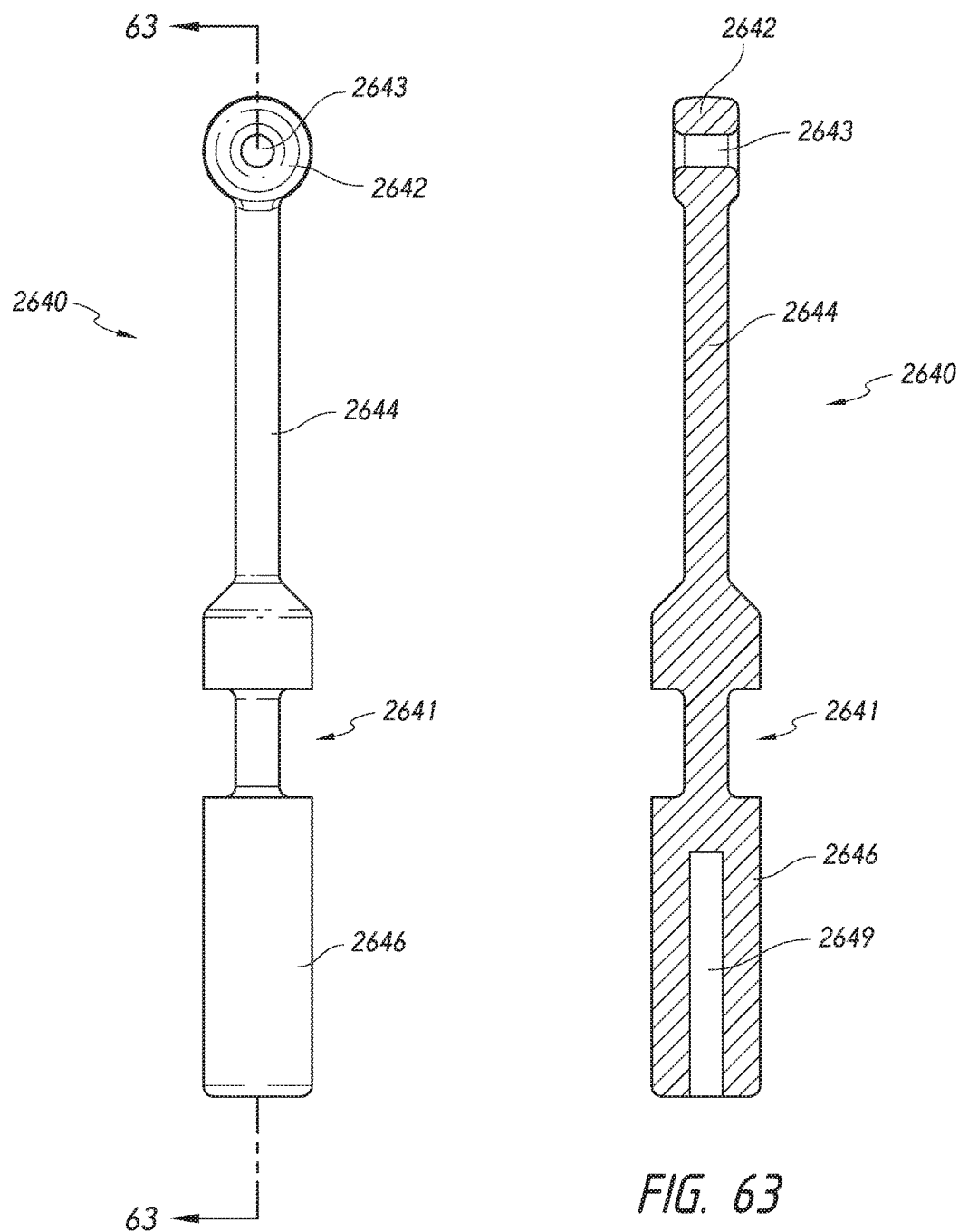
FIG. 62 illustrates a front view of a piercing member holder, according to some embodiments.
FIG. 63 illustrates a cross-sectional view of a piercing member holder, taken along the line 63-63 of FIG. 62.

FIGS. 62 and 63 illustrates an embodiment of a piercing member holder 2640 that includes a single circumferential cutout 2641 that can receive the radial projections 2441 and/or the circumferential projections 2443 of the locking arms 2446. FIG. 62 is a front view and FIG. 63 is a cross-sectional view taken along the line 63-63 of FIG. 62. As described above, when the radial projections 2441 and/or the circumferential projections 2443 of the locking arms are positioned within the cutout 2641, they can block movement of the holder 2640.

FIG. 64 illustrates a front view of a plunger assembly 2510 that can be used with a vascular access system 2140 where withdrawal of a piercing member is decoupled from initial movement of a plunger assembly 2510. FIG. 65 illustrates a bottom view of the plunger assembly. In some embodiments, the slots 2487 between prongs 2489 can be narrower than in the embodiments discussed with respect to FIG. 39. This can help provide additional strength to the prongs, which do not need to bend inward to block movement of a piercing member holder. In some embodiments, the slots can be the same size. Preferably, the slots are at least as wide as the locking arms 2446 on the second plunger 2484. This can allow the locking arms to pass through the slots when the locking arms are in a locked position.

In some embodiments, the size of the slots can be defined with respect to their radial width a along an inner circumference of the second plunger 2484. In some embodiments, for example, the slots can have a radial width a that is greater than or equal to about 5 degrees and/or less than or equal to about 60 degrees. In some embodiments, the slots can have a radial width a that is greater than or equal to about 10 degrees and/or less than or equal to about 50 degrees. In some embodiments, the slots can have a radial width a that is greater than or equal to about 15 degrees and/or less than or equal to about 40 degrees. In some embodiments, the slots can have a radial width a that is greater than or equal to about 25 degrees and/or less than or equal to about 35 degrees.

Figure 66:
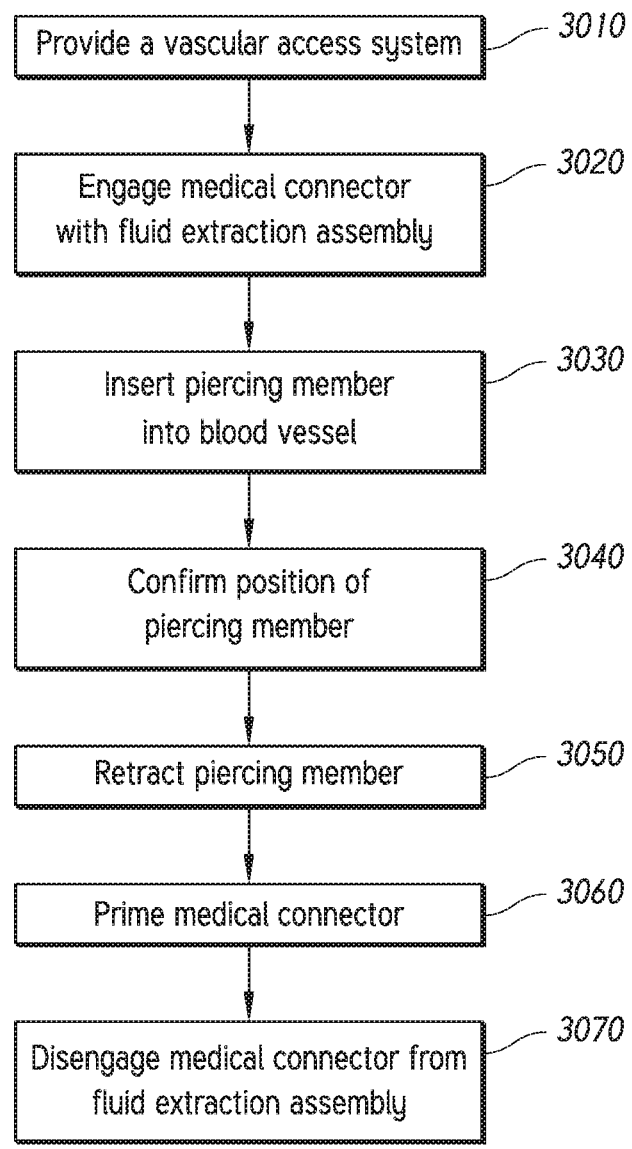
FIG. 66 is a flow chart of one embodiment of a method for using a vascular access system.

FIG. 66 illustrates a flow chart of one embodiment of a method of using a vascular access system. The method can include the step 3010 of providing a vascular access system. The vascular access system can be configured according to any of the various embodiments described herein. The method can further include the step 3020 of engaging a medical connector with a fluid extraction assembly. In some embodiments, this can include attaching the medical connector to a medical connector holder, although in some embodiments the medical connector may already be attached. In some embodiments, this step can include moving the medical connector into a second locked position within the fluid extraction assembly, such as within the medical connector holder.

In various embodiments, the method can further include the step 3030 of inserting a piercing member into a patient's blood vessel. In some embodiments, this also includes inserting a catheter into the blood vessel with the piercing member. Once the piercing member has been inserted into the blood vessel, its position can be confirmed at step 3040. This can include, for example, looking for blood in the catheter or an outer housing of the catheter. Blood can enter the catheter or outer housing as described above, such as through a slot 742 or opening 743 of the piercing member (e.g., FIG. 27). In some embodiments, a plunger can be partially withdrawn from the access system to facilitate blood flow through the piercing member to confirm its position. In some embodiments, the patient's blood pressure can be sufficient to confirm the piercing member position and a plunger does not need to be withdrawn.

Once the piercing member is properly positioned, and with it a catheter, the piercing member can be retracted at step 3050. In some embodiments, this can be done by at least partially withdrawing a plunger from the access system. Once the piercing member is properly positioned, the medical connector can also be primed at step 3060. In some embodiments where a plunger is at least partially withdrawn to retract the piercing member, withdrawing the plunger can also create a negative pressure to draw blood into the medical connector to prime the medical connector. In some embodiments, the medical connector can be primed or partially primed before the piercing member is retracted. In some embodiments, the piercing member can be retracted before the medical connector is primed or partially primed. In some embodiments, the piercing member can be automatically retracted as described above.

Once the medical connector has been primed, it can be disengaged from the fluid extraction assembly at step 3070. This preferably includes disconnecting the medical connector entirely from the fluid extraction assembly. The medical connector can then be used to connect other medical devices to the patient's blood stream.

Figure 67:
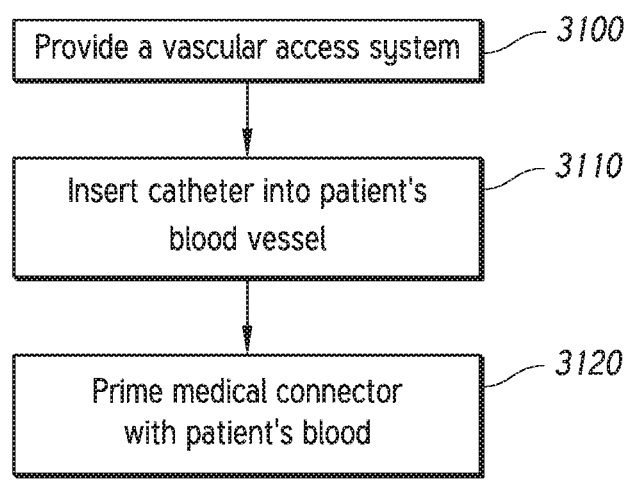
FIG. 67 is a flow chart of one embodiment of a method for using a vascular access system.

FIG. 67 illustrates a flow chart of one embodiment of a method of using a vascular access system. The method can include the step 3100 of providing a vascular access system. The vascular access system can be configured according to any of the various embodiments described herein. The method can further include the step 3110 of inserting a catheter into a patient's blood vessel. Once the catheter has been inserted into the blood vessel, a medical connector of the vascular access system can be primed with the patient's blood. This can be done according to any of the various embodiments described above, such as by withdrawing or partially withdrawing a plunger.

Although systems and methods have been disclosed in the context of certain embodiments and examples, it will be understood by those skilled in the art that the systems and methods extend beyond the specifically disclosed embodiments to other alternative embodiments and/or uses of the embodiments and certain modifications and equivalents thereof. In certain embodiments various components are integrated and/or replaced by a single component. It should be understood that various features and aspects of the disclosed embodiments can be combined with or substituted for one another in order to form varying modes of priming systems. Accordingly, it is intended that the scope of the systems and methods herein-disclosed should not be limited by the particular disclosed embodiments described above, but should be determined only by a fair reading of current and/or future claims.

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately," "about," "generally," and "substantially" may refer to a value, amount, or characteristic that is within less than 10% of, within less than 5% of, within less than 1% of, within less than 0.1% of, and within less than 0.01% of the stated value, amount, or characteristic. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise. The term "about," when used before a number, discloses both the exact number and numbers that are approximately equal to the number.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A; some embodiments can include B; some embodiments can include C; some embodiments can include A and B; some embodiments can include A and C; some embodiments can include B and C; and some embodiments include A, B, and C. The term "and/or" is used to avoid unnecessary redundancy.

The various features and processes described above may be used independently of one another, or may be combined in various ways. All possible combinations and subcombinations are intended to fall within the scope of this disclosure. In addition, certain method, event, state, or process blocks may be omitted in some implementations. The methods and processes described herein are also not limited to any particular sequence, and the blocks or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

As used herein, the term "clinician" means any individual who might be using, operating, or otherwise controlling the various devices, systems, and embodiments described herein.

The following is claimed:

1. A vascular access system for placement of a catheter within a patient's blood vessel, the vascular access system comprising:
   a catheter hub;
   a fluid passage positioned at least partially within the catheter hub;
   a catheter coupled to the catheter hub;
   a retractable needle coupled to the catheter hub;
   a connector coupled to the catheter hub; and
   a tube extending from the catheter hub to the connector, wherein the tube allows the connector to be positioned in different locations relative to the catheter hub,
   wherein the connector includes a first position in which a path through the connector is open and a second position in which a path through the connector is closed, and
   wherein a flow controller is coupled to the connector and is configured to transition the connector from the first position to the second position.

2. The vascular access system of claim 1, wherein a portion of the flow controller extends into the connector.

3. The vascular access system of claim 1, wherein a portion of the flow controller overlaps at least a portion of the connector on an outside of the connector.

4. The vascular access system of claim 1, wherein at least a portion of the tube is configured to extend toward the patient.

5. The vascular access system of claim 1, wherein the connector is configured to connect the catheter hub to a fluid extraction assembly to place the catheter hub in fluid communication with the fluid extraction assembly.

6. The vascular access system of claim 5, wherein the fluid extraction assembly comprises a fluid reservoir and a plunger.

7. The vascular access system of claim 6, wherein the fluid extraction assembly is configured such that sliding the plunger proximally expands the fluid reservoir and wherein the plunger is coupled to the retractable needle such that sliding the plunger proximally causes the retractable needle to retract proximally with respect to the catheter.

8. The vascular system of claim 6, wherein the catheter comprises a first passage and wherein the retractable needle is oriented coaxially with the first passage and configured to slide out of the first passage of the catheter.

9. The vascular system of claim 8, further comprising a second passage that fluidically couples the first passage to the fluid extraction assembly, wherein the second passage is configured such that fluid can flow from the first passage to the fluid extraction assembly.

10. The vascular access system of claim 1, further comprising an auto-retract feature that is configured to automatically retract the retractable needle.

11. The vascular access system of claim 1, wherein the tube is coupled to a proximal side of the catheter hub.

12. The vascular access system of claim 1, wherein the tube is configured to extend from a proximal side of the catheter hub at an angle relative to a central axis of the catheter hub.

13. The vascular access system of claim 1, wherein the connector is a needleless connector.

14. The vascular access system of claim 1, wherein the retractable needle is configured to extend through the catheter.

15. The vascular access system of claim 1, wherein the connector includes a plurality of threads to mechanically couple the connector to a device.

16. The vascular access system of claim 1, wherein the flow controller is removable.

17. The vascular access system of claim 1, wherein the flow controller is a cap.

18. The vascular access system of claim 1, wherein the flow controller is a seal.

* * * * *